(12) United States Patent  
Poulin et al.

(10) Patent No.: US 6,949,679 B1
(45) Date of Patent: Sep. 27, 2005

(54) POLYAMINE TRANSPORT INHIBITORS

(75) Inventors: Richard Poulin, Sainte-Foy (CA);
Marie Audette, Cap-Rouge (CA); Rene Charest-Gaudrealt, St. Nicolas (CA)

(73) Assignee: Universite Laval, Québec (CA)

( * ) Notice: Subject to any disclaimer, the term of this patent is extended or adjusted under 35 U.S.C. 154(b) by 0 days.

(21) Appl. No.: 09/529,319

(22) PCT Filed: Apr. 21, 1998

(86) PCT No.: PCT/US98/07806

§ 371 (c)(1),
(2), (4) Date: Feb. 9, 2001

(87) PCT Pub. No.: WO99/54283

PCT Pub. Date: Oct. 28, 1999

(51) Int. Cl.[7] .................. C07C 211/13; C07C 211/22
(52) U.S. Cl. ................................................ 564/512
(58) Field of Search .................... 564/512, 154; 514/625; 424/78.27, 78.37, 78.35

(56) References Cited

U.S. PATENT DOCUMENTS

| | | | | |
|---|---|---|---|---|
| 3,200,106 A | * | 8/1965 | Dickson et al. ............. | 530/231 |
| 3,201,472 A | * | 8/1965 | Spivack ..................... | 564/512 |
| 4,631,337 A | * | 12/1986 | Tomalia et al. ............ | 528/391 |
| 4,990,672 A | | 2/1991 | Johnson et al. | |
| 5,456,908 A | | 10/1995 | Aziz et al. ................ | 424/78.08 |
| 6,083,496 A | * | 7/2000 | Poulin et al. ............ | 424/78.27 |
| 6,673,192 B1 | * | 1/2004 | Woods et al. ............... | 156/314 |

FOREIGN PATENT DOCUMENTS

| | | |
|---|---|---|
| WO | WO93/04373 | 3/1993 |
| WO | WO 93/12777 | 7/1993 |
| WO | WO 98/17623 | 4/1998 |

OTHER PUBLICATIONS

Hubert et al, Journal of Biological Chemistry, vol. 271, No. 44, pp 27556–27563, 1996.*

Patricia Hubsch–Weber et al., Synthesis and Characterization of a New Series of [12]aneN, Type Macrocycles. Structures of two Protonated Metal–Free Ligands. Tetrahedron Letters, Vo. 38, No. 11, pp. 1911–1914, 1997.

Maria Huber et al., 2,2'–Dithiobis (N–ethyl–spermine–5–carboxamide) Is a High Affinity, Membrane–impermeant Antagonist of the Mammalian Polyamine Transport System. The Journal of Biological Chemistry, vol. 271, No. 44, 1996, pp. 27556–27563.

Egon Buhleier et al., "Cascade"—and "Nonskid–Chain–like" Synthesis of Molecular Cavity Topologies. Georg Thieme Publishers, pp. 155–158, 1978.

Ask et al., "Antileukemic effects of non–metabolizable derivatives of spermidine and spermine," Cancer Lett., 66:33–38, 1993.

Ask et al., "Increased survival of L1210 leukemic mice by prevention of the utilization of extracellular polyamines. Studies using a polyamine–uptake mutant, antibiotics and a polamine–deficient diet," Cancer Lett., 66:29–34, 1992.

Aziz et al., "A novel polymeric spermine conjugate inhibits polyamine transport in pulmonary artery smooth muscles cells," J. Pharmacol. Exper. Ther., 274:181–186, 1992.

Aziz et al., "The potential of a novel polyamine transport inhibitor in cancer chemotherapy," Pharmacol. Exper. Ther., 278:185–192, 1996.

Bergeron et al., "Development of a hypusine reagent for peptide synthesis," Org. Chem., 62:3285–3290, 1997.

Chaney et al., "Tumor selective enhancement of radioactivity uptake in mice treated with β–difluoromethylornithine prior to administration of $^{14}$C–putrescine," Life Sci., 32:1237–1241, 1983.

Chang et al., "Modulation of polyarnine biosynthesis and transport by oncogene transfection," Biochem. Biophys. Res. Comm., 157:264–270, 1988.

Cohen et al., "Targeting of cytotoxic agents by polyamines:synthesis of a chlorambucil–spermidine conjugate," J. Chem. Soc. Chem. Commun., pp. 298–300, 1992.

Duranton et al., "Suppression of preneoplastic changes in the intestine of rats fed low levels of polyamines," Cancer Res., 57:573–575, 1997.

Felschow et al., "Photoattinity labeling of a cell surface polyamine binding protein," 270:28705–28711, 1995.

Frebort and Adachi, "Copper/quinone–containing amine oxidases, an exciting class of ubiquitous enzymes," J. Ferment. Bioeng., 80:625–632, 1995.

Hayashi et al., Ornithine decarboxylase antizyme—A novel type of regulatory protein, Trends Biochem. Sci., 21:27–30, 1996.

He et al., "Antizyme delays the restoration by spermine of growth of polyamine–deficient cells through its negative regulation of polyamine transport," Biochem. Biophys. Res Commun., 203:608–614, 1994.

(Continued)

Primary Examiner—Shailendra Kumar
(74) Attorney, Agent, or Firm—Ogilvy Renault

(57) ABSTRACT

The present invention describes the design, synthesis and therapeutic use of a variety of novel inhibitors of polyamine transport. The main feature of this class of transport inhibitors is to incorporate a linker or side chain that prevents the uptake of polyamines and helps to conjugate polyamine analogs to form dimers with high inhibitory potency against polyamine uptake. These new compounds incorporate features that are designed to maximize their chemical and metabolic stability and their ability to bind to the polyamine transporter, and to minimize their toxicity by preventing their absorption by the cells. The purpose of such inhibitors is to prevent the uptake or salvaging of circulating polyamines by rapidly proliferating cells such as tumor cells, in order to potentiate the effect of therapeutic inhibitors of polyamine biosynthesis such as alpha-difluoromethylornithene.

4 Claims, 35 Drawing Sheets

OTHER PUBLICATIONS

Hessels et al., "Microbial flora in the gastrointestinal tract abolishes cytostatic effects of α–difluoromethylornithine in vivo," *Int. J. Cancer*, 43:1155–1164, 1989.

Holley et al., "Targeting of tumor cells and DNA by a chlorambucil–spermidine conjugate," *Cancer Res.*, 52:4190–4195, 1992.

Horn, et al., "Phase I–II clinical trial with α–difluoromethylornithine– an inhibitor of polyamine biosyntheses," *Eur. J. Cancer Clin. Oncol.*, 23:1103–1107, 1987.

Huber and Poulin, "Antiproliferative effect of spermine depletion by –cyclohexyl–1,3–diaminopropane in human breast cancer cell growth," *Cancer Res.*, 55:924–943, 1995.

Huber and Poulin, "Permissive role of polyamines in the cooperative action of estrogens and insulin or insulin–like growth ractor I on human breast cancer cell growth," *J. Clin. Endorcinol. Metab.*, 81:113–123, 1996.

Huber et al., "2,2'–Dithiobis(N–ethyl–spermine–5–carboximide) is a high affinity, membrane–impermeant antagonist of the mammalian polyamine transport system," *J. Biol Chem.*, 271:27556–27563, 1996.

Janne et al., "Polyamines from molecular biology to clinical applications," *Ann. Med.*, 23:241–259, 1991.

Kanter et al., "Preclinical toxicologic evaluation of DENSPM ($N^1$, $N^{11}$–diethylnorspermine) in rats and dogs," *Anti–Cancer Drugs*, 5:448–456, 1994.

Lakanen et al., "α–Methyl polyamines: metabolically stable spermidine and spermine mimics cabable of supporting growth in cells depleted of polyamines," *J. Med. Chem.*, 35:724–734, 1992.

Lessard et al., "Hormonal and feedback regulation of putrescine and spermidine transport in human breast cancer cells," *J. Biol. Chem.* 270:1685–1694, 1995.

Li et al., "Comparative molecular field analysis–based predictive model of structure–function relationships of polyamine transport inhibitors in L1210 cells," *Cancer Res.*, 57:234–239, 1997.

Love et al., "Randomized phase I chemoprevention dose–seeking study of α–difluoromethylornithine," *J:Natl. Cancer Inst.*, 85:732–737, 1993.

Marton and Pegg, "Polyamines as targets for therapeutic intervention," *Ann. Rev. Pharmacol. Toxicol.*, 35:55–91, 1995.

Mausumoto and Suzuki, "Polyamines as markers of malignancy," In:*The Physiology of Polyamines*, edited by U. Bachrach and Y.M. Heimer. Boca Raton, FL:CRC Press, 219–234, 1989.

McCann and Bitoni, "An overview of inhibition of polyamine metabolism and the consequent effects on cell proliferation in mammalian cells and parasitic protozoa," *Polyamines in the Gastrointestinal Tract*, edited by R.H. Dowling, U.R, Folsch and C. Loser, Dordrecht:Klawer Academic Publ., 143–153, 1992.

McCann and Pegg, "Ornithine decarboxylase as an enzyme target for therapy," *Pharmac. Ther.*, 54:195–215, 1992.

McCormack and Johnson, "Putrescine uptake and release by colon cancer cells," *Am. J. Physiol.*, 256:G868–G877, 1989.

Meyskens and Gerner, "Development of difluoromethyl–ornithine as chemoprevention agent for the management of colon cancer," *J. Cell Biochem.*, 22:126–131, 1995.

Minchin et al., "Inhibition of putrescine uptake by polypyridinium quaternary salts in B16 melanoma cells treated with difluoromethylornithine," *Biochem. J.*, 262:391–395, 1989.

Mitchell et al., "Feedback repression of polyamine transport is mediated by antizyme in mammalian tissue culture cells," *Biochem. J.*, 299:19–22, 1994.

Mitchell et al., "Feedback repression of polyamine uptake into mammalian cells require active protein synthesis," *Biochem Biophys. Res. Commun.*, 186:81–88, 1992.

Morgan, "Polyamine oxidases and oxidized polyamines," In:*The Physiology of Polyamines*, edited by U. Bachrach and U.M. Heimer. Boca Raton, FL:CRC Press, p. 203–229, 1989.

Moulinoux et al., "Biological significance of circulating polyamines in oncology," *Cell. Mol. Biol.*, 37:773–783, 1991.

Moulinoux et al., "The growth of MAT–LyLu rat prostatic adeno–carcinoma can be prevented in vivo by polyamine deprivation," *J. Urol.*, 146:1408–1412, 1991.

Nicolet et al., "Putrescine and spermidine uptake is regulated by proliferation and dexamethasone treatment inAR4–2J cells," *Int. J. Cancer*, 49:577–581, 1991.

O'Sullivan et al., "Inhibiting effects of spermidine derivatives on *Trypanosoma cruzi* trypanothione reductase," *J. Enzym Inhib.*, 11:97–114, 1996.

Osborne and Seidel, "Gastrointestinal luminal polyamines: cellular accumulation and enterohepatic circulation," *Am. J. Physiol.*, 258:G576–G584, 1990.

Parchment et al., "Serum amine oxidase activity contributes to crisis in mouse embryo cell lines," *Proc. Natl. Acad. Sci.*, USA 87:4340–4344, 1990.

Pegg et al., "Effect of S–adenosyl–1, 12–diamino–3–thio–9–azadodecane,a multisubstrate adduct inhibitor of spermine synthase, on polyamine metabolism in mammalian cells," *Biochemistry*, 28:8446–8453, 1989.

Pegg et al., "Inhibition of polyamine biosynthesis and function as an approach to drug design," *Enzymes as Targets for Drug Design*, edited by M.G. Palfreyman, P.P. McCann, P.P. Lovenberg, W. Temple, J.G. Temple and A. Sjoerdsma. Orlando:Academic Press, 157–183, 1989.

Pegg et al., "Use of aminopropyltransferase inhibitors and of non–metabolizable analogs to study polyamine regulation and function," *Int. J. Biochem. Cell. Biol.*, 27:425–442, 1995.

Perrson et al., "Curative effect of DL–2 difluoromethylomithine on mice bearing mutant L1210 leukemia cells deficient in polyamine uptake," *Cancer Res.*, 48:4807–4811, 1988.

Porter and Bergeron, "Spermidine requirement for cell proliferation in eukaryotic cells: structural specificity and quantitation," *Science*, 219:1083–1085, 1983.

Porter et al., "Antitumor activity of $N^1$, $N^{11}$–bis(ethyl)norspermine against human melanoma xenografts and possible biochemical correlates of drug action," *Cancer Res.*, 53:581–586, 1993.

Porter et al., "Biological properties of $N^4$ spermidine derivatives and their potential in anticancer chemotherapy," *Cancer Res.*, 42:4072–4078, 1982.

Porter et al., "Biological properties of $N^4$–and $N^1$, $N^8$–spermidine derivativies in cultured L1210 leukemia cells," *Cancer Res.*, 45:2050–2057, 1985.

Porter et al., "Collateral sensitivity of human melanoma multidrug–resistant variants to the polyamine analogue, $N^1$, $N^{11}$ diethylnorspermine," *Cancer Res.*, 54:5917–5924, 1994.

Porter et al., "Polyamine inhibitors and analogues as potential anticancer agents," *Polyamines in the Gastrointestinal Tract*, edited by R.H. Dowling, U.R. Folsch and C. Loser. Dordrecht:Kluwer Academic Publ., 301–322, 1992.

Poulin et al., "Dependence of mammalian putrescine and spermidine transport on membrane potential: identification of an amiloride binding site on the putrescine carrier," *Biochem. J.*, 330:1283–1291, 1998.

Pusztai et al., "Stimulation of growth and polyamine accretion in the small intestine and pancreas by lectins and trypsin in inhibitors," *Polymines in the Gastrointestinal Tract*, edited by R.H. Dowling, U.R. Folsch and C. Loser. Dordrecht:Kluwer Academic Publ., 473–483, 1992.

Quemener et al., "Polyamine deprivation:a new tool in cancer treatment," *Anticancer. Res.*, 14:443–448, 1994.

Quemener et al., "Tumour growth inhibition by polyamine deprivation," *Polyamines in the Gastrointestinal Tract*, edited by R.H. Dowling, U.R. Folsch and C. Loser. Dordrecht:Kluwer Academic Publ., 375–385, 1992.

Rinehart and Chen, "Characterization of the polyamine transport system in mouse neuroblastoma cells," *J. Biol. Chem.*, 259:4750–4756, 1984.

Sarhan et al., "The gastrointestinal tract as polyamine source for tumor growth," *Anticancer Res.*, 9:215–224, 1989.

Schechter et al., "Clinical aspects of inhibition of ornithine decarboxylase with emphasis on therapeutic trials of eflornithine (DFMIO) in cancer and protozoan diseases," *Inhibition of Polyamine Metabolism. Biological Significance and Basis for New Therapies*, edited by P.P. McCann, A.E. Pegg and A. Sjoerdsma. Orlando, FL:Academic Press, 345–364, 1987.

Seiler and Dezeure, "Polyamine transport in mammalian cells," *Int J. Biochem.*, 22:211–218, 1990.

Seiler et al., "Endogenous and exogenous polyamines in support of tumor growth," *Cancer Res.*, 50:5077–5083, 1990.

Seiler et al., "Polyamine transport in mammalian cells. An update," *Int. J. Biochem. Cell Biol.*, 28:843–861, 1996.

Seiler, "Polyamine catabolism and elimination by the vertebrate organism," *Polyamines in the Gastrointestinal Tract*, edited by R.H. Dowling, U.R. Folsch and C. Loser. Dordrecht:Kluwer Academic Publ., 65–85, 1992.

Sjoerdsma and Schechter, "Chemotherapeutic implication so polyamine biosynthesis inhibition," *Clin. Pharm. Thera.*, 35:287–300, 1984.

Sjoerdsma and Schechter, "Successful treatment of lethal protozoal infections with the ornithine decarboxylase inhibitor, α–difluoromethylornithine," *Trans. Ass. Am. Physic.*, 97:70–79, 1984.

Stark et al., "Synthesis and evaluation of novel spermidine derivatives as targeted cancer chemotherapeutic agents," *J. Med. Chem.*, 35, 4264–4269, 1992.

Steele et al., "Preclinical efficacy evaluation of potential chemo–preventive agents in animal carcinogenesis: methods and results from the NCI Chemoprevention Drug Development Program," *J. Cell. Biochem*, (*suppl.*) 20:32–54, 1994.

Sunkara, P.S. et al. "Inhibitors of polyamine biosynthesis: cellular and in vivo effects on tumor proliferation," *Inhibition of Polyamine Metabolism Biological Significance and Basis for New Therapies.*, edited by P.P. McCann, A.E. Pegg and A. Sjoerdsma. Orlando:Academic Press, 121–140, 1987.

Talpaz et al., "Clinical studies of α–difluoromethylornithine and α–interferon combination in cancer patients," *The Physiology of Polyamines*, edited by U. Bachrach and Y.M. Heimer, Boca Raton, FL:CRC Press, 287–292, 1989.

Tanaka et al., "Chemoprevention of oral carcinogenesis by DL–α–difluromethylornithine, an ornithine decarboxylase inhibitor: dose–dependent reduction in 4–nitroquinoline 1–oxide–induced tongue neoplasms in rats," *Cancer Res.*, 53:772–776, 1993.

Tempero et al., "Chemoprevention of mouse colon tumors with difluoremethylornithine during and after carcinogen treatment," *Cancer Res.*, 49:5793–5797, 1989.

Tjandrawinata and Byus, "Regulation of the efflux of putrescine and cadaverine from rapidly growing cultured RAW 264 cells by extracellular putrescine," *Biochem. J.*, 305:291–299, 1995.

Tjandrawinata et al., "Regulation of putrescine export in lipopolysaccharide or IFN–γ–activated murine monocytic–leukemic RAW 264 Cells," *J. Immunol.*, 152:3039–3052, 1994.

Zang and Sadler, "Synthesis of hexamine ligands by using trityl as an N–blocking agent," *Synthetic Communications*, 27:3145–3150, 1997.

* cited by examiner

| R | NAME | $K_i(\mu M)$ |
|---|------|--------------|
| H | MESC | 33.6 ± 7.2 |
| —$CH_2$—C(=O)—$NH_2$ | MESC-iodoacetamide | 48.9 ± 9.1 |
| —$CH_2$—C(=O)—NH— | MESC-LY | 44.1 ± 8.8 |
| —$CH_2$—C(=O)—NH— | MESC-ASIB[α] | 18.3 ± 8.2 |

FIG. 5

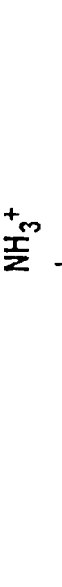
FIG. 11A PUTRESCINE
FIG. 11B SPERMIDINE
FIG. 11C SPERMINE
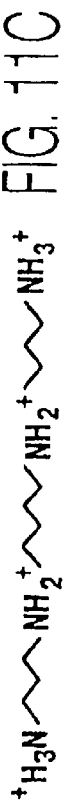
FIG. 11D DEASC
FIG. 11E DESC
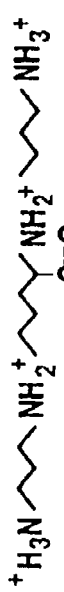
FIG. 11F MESC

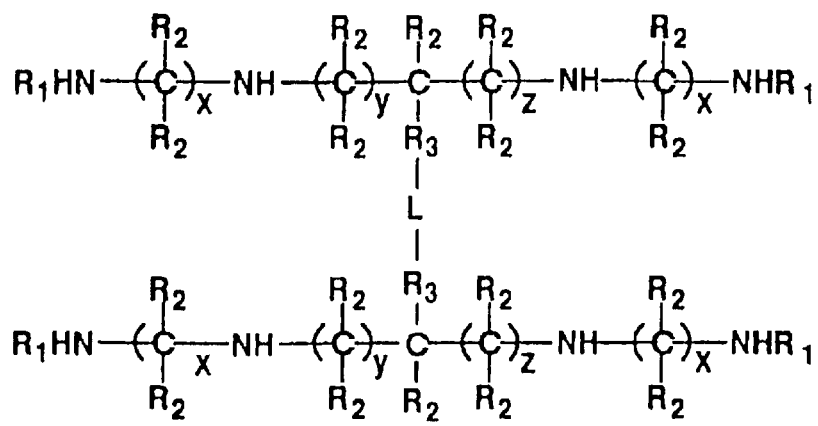
L = A CHEMICAL STRUCTURE (THE LINKER)  FIG. 17A
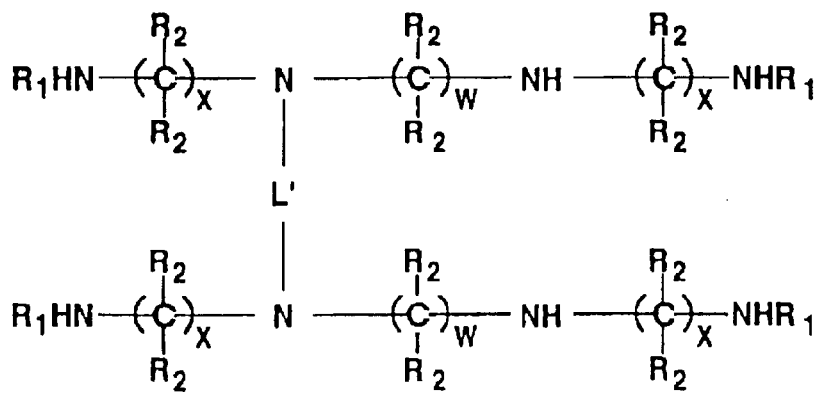
L' = A CHEMICAL STRUCTURE (THE LINKER)  FIG. 17B
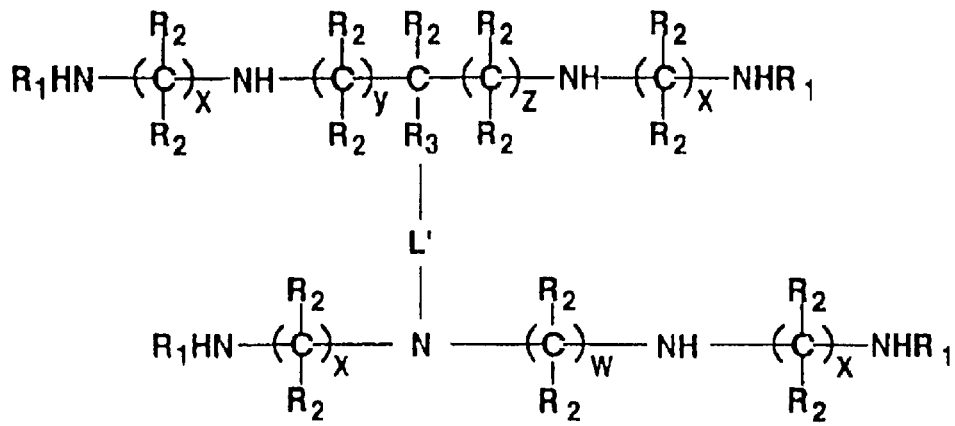
L' = A CHEMICAL STRUCTURE (THE LINKER)  FIG. 17C

I

BABAC

II

BNSpd-(n+2)

III

BSpd-(n+2)

IV

TADAX

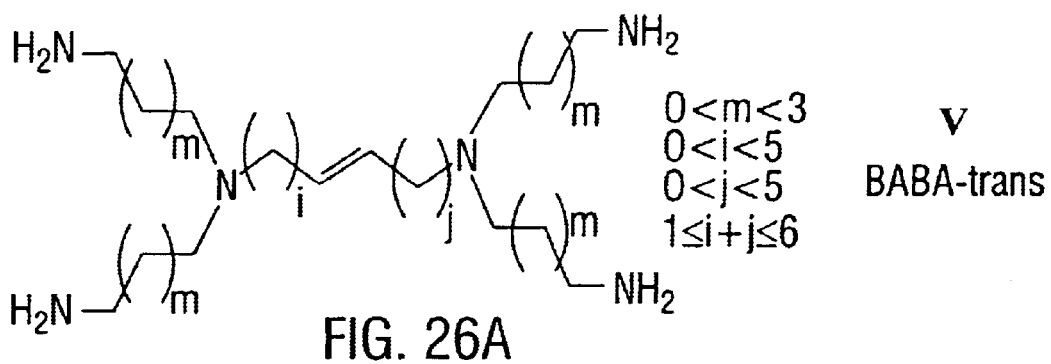
FIG. 26A    V   BABA-trans
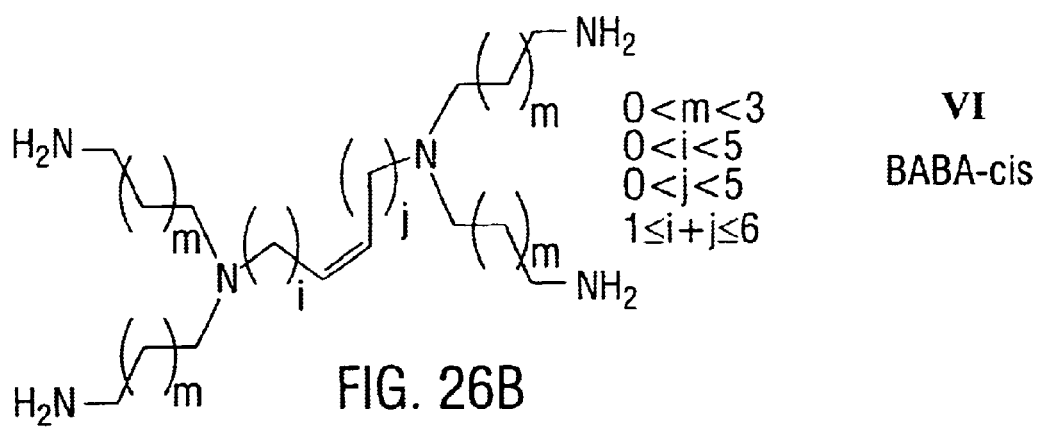
FIG. 26B    VI   BABA-cis
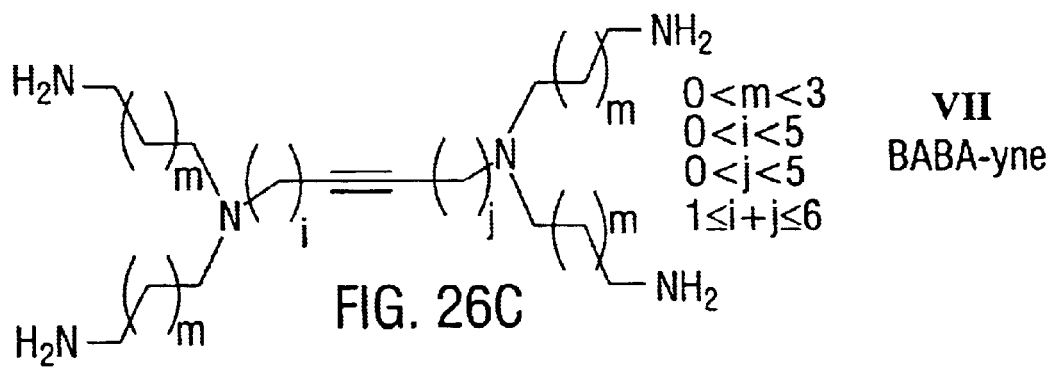
FIG. 26C    VII   BABA-yne

BABAC

AAC

DESC

POLYAMINE TRANSPORT INHIBITORS

This application is a 371 of PCT/US98/07806, filed Apr. 21, 1998.

FIELD OF THE INVENTION

The present invention relates to a novel class of competitive inhibitors of natural polyamine transport in mammalian cells. The present invention is more particularly directed to low molecular weight, high-affinity, specific, impermeant, pure antagonists of polyamine transport of a structure different to that of endogenous polyamines. The novel inhibitors of the present invention exhibit an effect on cultured tumor cells essentially cytostatic, with minor non-specific effects. The present invention is also directed to the use of such novel inhibitors of polyamine transport to evaluate the antitumor efficacy of polyamine depletion strategies with minimal systemic cytotoxic effects or to control and treat disorders involving unrestrained cell proliferation and/or cell differentiation wherein polyamine transport is required.

BACKGROUND OF THE INVENTION

Natural polyamines such as putrescine (1,4-butanediamine), spermidine (N-3[aminopropyl]-1,4-diaminobutane) and spermine (N,N'-bis-[3-aminopropyl]-1, 4-butanediamine) play essential roles in the control of macromolecular synthesis and growth processes in eukaryotic cells. Cells maintain appropriate polyamine concentrations principally by de novo synthesis from amino acids wherein ornithine decarboxylase catalyzes conversion of ornithine to putrescine, which is then converted to spermidine and spermine. Most tissues also possess a specific plasma membrane transport system allowing for utilization of plasma sources of polyamines.

Inhibitors of polyamine biosynthesis such as α-difluoromethylornithine (DFMO), which inhibits ornithine decarboxylase, cause an extensive depletion of polyamines followed by growth arrest in virtually all known mammalian cell types in vitro. Since tissues such as tumor cells and other transformed or rapidly proliferating cells exhibit a tissues such as tumor cells and other transformed or rapidly proliferating cells exhibit a high demand for polyamines, these properties have encouraged an extensive assessment of such inhibitors for the treatment of proliferative diseases, including several types of tumors, in experimental models and in clinical trials. Unfortunately, the antitumor efficacy of such inhibitors in vivo has been disappointing. The failure of DFMO to halt tumor growth in animal models has been clearly correlated with the elevated polyamine transport activity found in transformed cells. Indeed, decontamination of the gastrointestinal tract, which is the main vector of circulating polyamines through bacterial microflora activity, along with a polyamine-free diet, markedly potentiate the in vivo efficacy of DFMO against tumor progression. Moreover, mutant mouse leukemia cells deficient in polyamine transport are much more susceptible than the parental strain to growth inhibition by DFMO treatment in host animals. Besides, growth inhibition associated with DFMO-induced polyamine depletion in ZR-75-1 human breast cancer cells can be completely reversed by concentrations of spermidine as low as 300 nM, i.e., such as those found in human plasma (Moulinoux, J. -P., Quemener, V., and Khan, N. A. 1991. *Cell. Mol. Biol.* 37: 773–783; Scalabrino, G. and Ferioli, M. E. 1981. *Adv. Cancer Res.* 36: 1–102; Bachrach, U., 1989, in *The Physiology of Polyamines* (Bachrach, U. and Heimer, Y. M., eds.) Vol. II, pp. 235–249, 2 vols, CRC Press, Boca Raton, Fla.). The striking efficiency of the transport system to salvage exogenous polyamines in DFMO-treated cells owes to its upregulation consecutive to polyamine depletion (Seiler, N. and Dezeure, F. 1980, *Int. J. Biochem.* 22: 211–218; Byers, T. L. and Pegg, A. E. 1990, *J. Cell Physiol.* 143: 460–467; Lessard, M., Zhao, C., Singh, S. M. and Poulin, R. 1995, *J. Biol. Chem.* 270: 1685–1694; Kakinuma, Y., Hoshino, K., and Igarashi, K. 1988, *Eur. J. Biochem.* 176: 409–414). These data reinforce the view that cellular import of exogenous polyamines is the main factor limiting the efficacy of DFMO and other polyamine biosynthesis inhibitors as antitumor agents in vivo (Sarhan, S. Knödgen, B., and Seiler, N, 1989, *Anticancer Res.* 9: 215–224; Hessels, J., Kingma, A. W., Ferwerda, H., Keij, J., Van der Berg, G. A., and Muskiet, F. A. J. 1989, *Int. J. Cancer* 43: 115–1166; Ask, A., Persson, L. and Heby, O. 1992, *Cancer Lett.* 66: 29–34; Seiler, N., Sarhan, S., Grauffel, C., Jones, R., Knödgen, B. and Moulinoux, J. -P. 1990, *Cancer Res.* 50: 5077–5083; Persson, L., Holm, I., Ask, A. and Heby, O. 1988, *Cancer Res.* 48: 4807–4811).

Depletion of intracellular polyamines in tumor cells is thus a well-known strategy in anticancer therapies. However, it is now of common knowledge that depleting intracellular polyamines generally enhances polyamine uptake. To date, molecular information on the carrier molecules of the mammalian polyamine transport system is still unavailable. A few attempts have been made previously to design specific inhibitors of polyamine transport. Based on the finding that paraquat (4,4'-bipyridine) is a substrate of the putrescine transport system (Smith, L. L. and Wyatt, I. 1981, *Biochem. Pharmacol.* 20, 1053–10581; Rannels, D. E., Pegg, A. E., Clark, R. S. and Addison, J. L. 1985, *Am. J. Physiol.* 249, E506–E513), a series of polypyridinium salts, including compounds with a low $K_i$ against putrescine uptake and low acute toxicity for mammalian cells have been synthesized (Minchin, R. F., Martin, R. L., Summers, L. A. and Ilett, K. F. 1989, *Biochem. J.* 262, 391–395). However, it is unclear whether such compounds can efficiently inhibit polyamine transport or are accumulated intracellularly. A number of polyamine analogs are effective competitors of polyamine uptake while being themselves substrates for transport (Seiler, N. and Dezeure, F., 1990, *Int. J. Biochem. Cell. Biol.* 27: 425–442; Bergeron, R. J., and Seligsohn, H. W. (1986) *Bioinorg. Chem.* 14: 345–355; Porter, C. W., Bergeron, R. J. and Stolowich, N. J. 1982, *Cancer Res.* 42: 4072–4078; Porter, C. W., Basu, H. S., Feuerstein, B. G., Deen, D. F., Lubich, W. P., Bergeron, R. J., Samejima, K., and Marton, L. J. 1989, *Cancer Res.* 49: 5591–5597; Pegg, A. E., Wechter, R., Pakala, R., and Bergeron, R. J. 1989, *J. Biol. Chem.* 264: 11744–11749; Pegg, A. E., Nagarajan, S., Naficy, S. and Ganem, B. 1991, *Biochem. J.* 274: 176–171; Porter, C. W., Ganis, B., Libby, P. R. and Bergeron, R. J. 1991, *Cancer Res.* 51: 3715–3720).

More recently, a high-molecular weight (Mr=25 kD) spermine polymer has been described by Aziz et al. in U.S. Pat. No. 5,456,908, as a competitive inhibitor of polyamine transport, with a $K_i$ in the $10^{-6}$M range. In this patent document are disclosed two novel classes of polyamine transport inhibitors of high molecular weight, namely polymeric conjugates of normally transported substances (TS) of the structure $(TS)_m$ or conjugates of a polyamine and a protein or polypeptide (P) linked by known coupling agents and represented by (TS)-(P), wherein the repeating units of the polymer comprise the targeted polyamine. It is predictable that the inhibitors of Aziz et al. would be difficult to eliminate in vivo due to their high molecular weight and the high positive charge of the polymers, notwithstanding the risk of immunogenicity inherent to such high molecular weight inhibitors. The length of the polymers of Aziz et al. as well as their charge would cause their adsorption to the cellular surface, which bears negative charges due to the presence of glycoproteins, e.g. sialic acid. Poly-L-lysine, a commercially used compound analogous to high molecular weight polymers of polyamines by its positive charges, is known to promote a strong electrostatic interaction between the cell and its substrate, as in the induction of positive charges of gamma irradiation of synthetic polymers used to produce dishes for tissue culture. The polyamine transport inhibitors of Aziz et al. present the additional drawback of being highly cytotoxic. It is noteworthy that their spermine polymer is effective in decreasing contents of polyamines in cells even when not used in combination with DFMO and at concentrations much higher than those required to block polyamine uptake, which indicates inherent high toxicity of the compound toward the cell by a mechanism independent of polyamine transport per se. The cytotoxicity of the spermidine polymer of Aziz et al. is most probably explained by a non-specific effect on cellular physiology such as the cellular membrane. Although the authors pretend to demonstrate the specific action of the polymers with the fact that exogenous spermidine reverses the induced cytotoxicity, it is highly likely that competition between spermidine and the polymers modifies the electrostatic interaction with the negatively-charged sites on the cellular membrane is responsible for the effect. The results obtained by Aziz et al. indicate that at least part of the effect observed with high molecular weight polymers is non-specific (Aziz, S. M., Tofiq, S. F., Gosland, M. P., Olson, J. W. and Gillespie, M. N. 1995, *J. Pharmacol. Exp. Ther.* 274, 181–196). The usefulness of this spermine polymer for specificity blocking polyamine accumulation is therefore uncertain in view of its marked cytotoxicity.

Cysteamine and aliphatic monoamines of similar chain length such a n-butylamine and n-pentylamine have a low but significant ability to antagonize putrescine uptake (Gordonsmith, R. H., Brooke-Taylor, S., Smith, L. L. and Cohen, G. M. 1983, *Biochem. Pharmacol.* 32, 431–437), although the mode of inhibition of these compounds has not been reported. The only polyamine-like structure known to interact non-competitively with the polyamine transport system is pentamidine, an aromatic diamidine (Jones, H. E., Blundell, G. K., Wyatt, I., John, R. A., Farr, S. J. and Richards, R. J. 1992, *Biochem. Pharmacol.* 43, 431–437), but the structural basis of its inhibitory activity is not yet clear.

It follows that there still exists a need for effective polyamine transport inhibitors which, while inhibiting the transport of polyamines, will not be internalized by the transport system and will not be toxic to the cell. The availability of low molecular weight inhibitors of polyamine transport would provide for the possibility of better renal elimination, as well as lower risks of being immunogenic. The availability of high-affinity, specific, but impermeant antagonists of polyamine transport would also allow to evaluate the antitumor efficacy of polyamine depletion strategies in vivo with minimal systemic cytotoxic effects.

There is much preclinical evidence supporting the hypothesis that the efficacy of the suicide inhibitor of ornithine decarboxylase, D,L-α-difluoromethylornithine (DFMO= Eflornithine) as a chemotherapeutic agent is limited by the enhanced ability of tumor cells to transport polyamines from plasma sources. Plasma polyamines are partly derived from various plasma sources (7, 12, 18, 58–60, 62, 70) and from the activity of the gastrointestinal microflora, which produces and excretes very high amounts of putrescine and cadaverine (1, 17, 45, 50, 62, 70), which can enter the general circulation through the enterohepatic pathway (6, 45). Other systemic contributions can also be attributed to polyamine excretion by peripheral tissues, including dying tumor cells (32, 35, 41, 42, 63, 64, 67, 79, 80). The enhanced uptake of polyamines by tumor cells results both from the increased polyamine transport activity that accompanies the malignant phenotype (11, 43, 51, 68, 69), and from the effect of DFMO itself, which causes a compensatory upregulation of polyamine uptake across the plasma membrane (9, 10, 14–16, 22, 25, 29, 31, 38, 39, 43, 47, 48, 50, 57, 61). One possible strategy that could be used to overcome this phenomenon would be to administer a pure antagonist of polyamine transport, i.e. a drug which binds with high affinity to the polyamine transporter, but which cannot be transported by this membrane protein. While a need continues to exist for such compound, no such compound is yet available.

SUMMARY OF THE INVENTION

In accordance with the present invention, there is now provided polyamine transport inhibitors having a low molecular weight, less susceptible to immunogenicity and to non-specific interactions with the cellular membrane. These inhibitors have high affinity, are specific, impermeant, pure antagonists of polyamine transport in mammalian cells while exhibiting minimal cytotoxic effects.

There is thus provided in accordance with the present invention synthetic derivatives of original polyamines. In some aspects, the original polyamine is modified to comprise an amido group immediately linked to a carbon atom of said original polyamine, said synthetic derivatives inhibiting the cellular uptake of natural polyamines by specifically binding cellular transporters for said natural polyamines. Surprisingly, the immediate vicinity of the amido group to the backbone of the original polyamine preserves the specificity of the derivative towards the transporter while conferring thereto an impermeant character, providing a true antagonist. In some embodiments, the amido group is located between two internal nitrogen atoms of the original polyamine. In other embodiments, the synthetic derivative comprises a dimer wherein monomers of said dimer are linked together by a spacer side chain anchored to the amido group of each monomer.

Although natural polyamines, such as putrescine, spermine and spermidine, can be used as the original polyamine, other non-natural polyamines can be used as a starting material for the making of synthetic derivatives of the present invention.

Accordingly, a synthetic derivative comprising the following general formula:

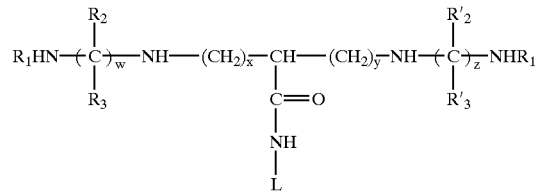

provides the structure of some embodiments of the invention, wherein $R_1$ and $R_1'$ independently represent a hydrogen atom or an alkyl group having 1 to 2 carbon atoms, $R_2$, $R_2'$, or $R_3$ and $R_3'$ independently represent a hydrogen atom or a methyl group, w and z independently represent an integer of 3 or 4, x represents an integer from 0 to n, y represents an integer from 0 to n, n represents an integer from 3 to 6, the sum of x and y equals n, and L represents a hydrogen atom or a molecule which cannot be captured by said natural polyamine transporter. The side chain or linker L may be labeled and be used as a marker for a polyamine transporter. Furthermore, the side chain L can be varied to increase the affinity of the derivative for the transporter. The side chain L may also become a spacer molecule useful in the formation of a dimer. This spacer side chain comprises a linear hydrocarbon-containing backbone of 3 to 8 atoms. The backbone may comprise sulfur, oxygen, or nitrogen atoms.

In yet other embodiments, the original polyamine is spermine. Three derivatives have been obtained therefrom: N-(2-mercaptoethyl)spermine-5-carboxamide (MESC), the disulfide from thereof, namely 2,2'-dithiobis(N-ethyl-spermine-5-carboxamide) (DESC), and N-[2,2'-dithio(ethyl, 1-aminoethyl)]spermine-5-carboxamide (DEASC).

It is an object of the invention to provide the use the above synthetic derivatives for inhibiting the activity of a natural polyamine transporter. In some embodiements, the method may be described as comprising the step of contacting said transporter with an inhibitory effective amount of said synthetic derivative. This inhibition results in the control of the treatment of disorders involving unrestrained cell proliferation and/or differentiation where control of polyamine transport is required, when used in combination with an inhibitor of polyamine synthesis such as DFMO.

It is further another object of the invention to provide a use of the non-dimeric derivatives as a marker for a polyamine transporter, which comprises the steps of labeling said synthetic derivative, binding to said transporter said labeled synthetic derivative and detecting said bound labeled marker as an indication of the presence of said polyamine transporter. The above sequence of steps results in the diagnosis of a disorder involving unrestrained cell proliferation and/or differentiation where control of polyamine transport is required.

It is also another object of the invention to provide a pharmaceutical composition for treating disorders wherein control of polyamine transport is required, comprising any-one of the above derivatives in adjunction with an acceptable pharmaceutical carrier. Preferably, this composition also comprises an inhibitor of polyamine synthesis, such as DFMO.

The applicants have unexpectedly discovered that the presence of a lateral amido group immediately linked to a carbon atom of the polyamine backbone of a synthetic derivative of an original polyamine confers impermeant properties to the so derived synthetic polyamine against the mammalian cell. It follows that the synthetic polyamine derivatives of the present invention, by exhibiting high affinity for diamine and polyamine transport systems, block the transport of natural polyamines by competing therewith, while in the same time acting as poor substrate for intracellular uptake. The affinity of the polyamine derivative for the transporter system is further enhanced by increasing the length of a side chain anchored to the amido group of the derivative. The best affinity is achieved by dimerizing the polyamine derivative with the aid of a spacer molecule anchored at both ends to the amido group of each monomer. The flexibility of the chemical structure of the inhibitors of the present invention permits better optimization of the activity and affinity than a simple polymeric structure such as $(TS)_n$. For example, modifications to the polyamine backbone as taught by the present invention, such as methylation of C1 and C12, lowers the possibility of oxidation of the primary amines by the serum amine oxidase, which is present in mammalian sera. Additional modifications including adjunction to the lateral chain of alkylating groups that irreversibly modify residues that are essential to the activity of the polyamine transporter, such as carboxylic moieties of the carrier protein, are also contemplated in the present invention (Torossian, K., Audette, M., and Poulin R., 1996, *Biochem. J.* 319: 21–28). The inhibitory action of the derivatives of the present invention is thus enhanced. By diminishing the amount of active transporters, additional modifications to the side chain that can be of potential therapeutic interest include the incorporation of reactive groups to the side chain that would allow the covalent modification of residues in the polyamine transporter by the principle of affinity labeling, and its subsequent irreversible inactivation.

This finding clearly demonstrates that modification of the chemical structure of the lateral chain optimizes the affinity of the polyamine derivative without augmenting to a great extent the molecular weight thereof. This markedly contrasts with the teachings of Aziz et al. who make use of high molecular weight polymers. Moreover, the mode of action of the inhibitors herein proposed, clearly different to that of Aziz et al. which relies upon their inherent cytotoxicity, is a competitive inhibition of the polyamine uptake.

Specific transport inhibition by polyamines dimerized via a side group on an integral atom of the polyamine chain is not limited to spermine or spermine-like dimers, but can also be obtained with dimers of triamines such as spermidine[N-(3-aminopropyl)-1,4-diaminobutane], sum-homospermidine [n-(4-aminobutyl)-1,4-diaminobutane] and sym-norspermidine[N-(3-aminopropyl)-1,3-diaminopropane]. We have synthesized novel spermidine, sym-homospermidine and sym-norspermidine dimers cross-linked through aliphatic or aromatic side chains on the central secondary amino group. We have found that such compounds act as inhibitors of polyamine transport with a potency similar or greater than that of dimeric polyamine transport inhibitors with a spermine-like backbone such as 2,2'-dithiobis[N-ethyl-spermine 5-carboxamide (or DESC).

In some embodiements, one spermidine or sym-norspermidine chain is cross-linked to a second spermidine or sym-norspermidine chain with an N-alkyl spacer side group anchored to the secondary amino group of said spermidine or sym-norspermidine chain. In particular embodiements, said spacer side group is an aliphatic carbon chain or an aromatic carbon chain.

Other objects, advantages and features of the present invention will become more apparent upon reading of the following non restrictive description of preferred embodiments thereof, given by way of example only and with reference to the accompanying drawings.

BRIEF DESCRIPTION OF THE DRAWINGS

In the appended drawings:

FIG. 5 illustrates graphically the structure of MESC thioether derivatives and their $K_i$ values with respect to spermidine uptake in CHO-K1 cells. The various conjugates were prepared from MESC as described supra, and structure and name of the substituents are given in the first two columns from the left, wherein R corresponds to the group attached to sulfur in MESC (structure VII, FIG. 1). The rate of spermidine uptake was determined in CHO-K1 cells in the presence of increasing concentrations of the various MESC derivatives, using 1 μM [³H]spermidine as substrate. $K_i$ values are given as the mean±SD of triplicate determinations from 2 to 3 experiments;

FIG. 11. Structures of putrescine, of the natural polyamines spermidine and spermine, and of three cell-impermeant inhibitors of polyamine transport (DESC, DEASC and MESC).

FIGS. 17A, 17B and 17C presents three classes of dimeric polyamine transport inhibitors according to the site of attachment of the linker (L) to the polyamine chain.

FIG. 17A—C-linked dimeric analogs. $R_1$ is H, methyl, ethyl or propyl; $R_2$ is H or methyl; $R_3$ is an alkyl, amide, keto, ether, thioether, phosphono or sulfonyl group; x is greater than 2 and less than 5 (2<x<5), and the sum of y+z is greater than or equal to 2 and less than or equal to 6 (2≦y+z≦6). The linker L is any chemical structure covalently linked to the $R_3$ groups and which prevents the uptake of the analog.

FIG. 17B—N-linked dimeric analogs. $R_1$ is H, methyl, ethyl or propyl; $R_2$ is H or methyl; x is greater than 2 and less than 8 (2<x<8), and w is greater than 2 and less than 7 (2<w<7). The linker L is any chemical structure covalently linked to one internal amino group of each polyamine chain and which prevents the uptake of the analog.

FIG. 17C—C-linked/N-linked mixed dimeric analogs. $R_1$ is H, methyl, ethyl or propyl; $R_2$ is H or methyl; x is greater than 2 and less than 5 (2<x<5), the sum of y+z is greater than or equal to 2 and less than or equal to 6 (2≦y+z≦6), and w is greater than 2 and less than 8 (2<w<8). The linker L is any chemical structure covalently linked to one internal amino group of one polyamine chain and to the $R_3$ of the other polyamine chain, and which prevents the uptake of the analog.

FIG. 26 illustrates the structure of other representative dimeric transport inhibitors with a triamine backbone that are included in the present invention. BABA-trans and BABA-cis stands for the trans and cis isomers of N,N'-N, N'-bis(3-aminopropyl),N,N'-bis(4-aminobutyl) derivatives of α,α'-diaminoalkenes, which are dimeric derivatives of either sym-homospermidine, sym-norspermidine or spermidine. BABA-yne stands for N,N'-N,N'-bis(3-aminopropyl), N,N'-bis(4-aminobutyl)derivatives of α,α'-diaminoalkynes, which are dimeric derivatives of either sym-homospermidine, sym-norspermidine or spermidine.

DETAILED DESCRIPTION OF THE PREFERRED EMBODIMENTS

Materials and Methods

Figure 1:
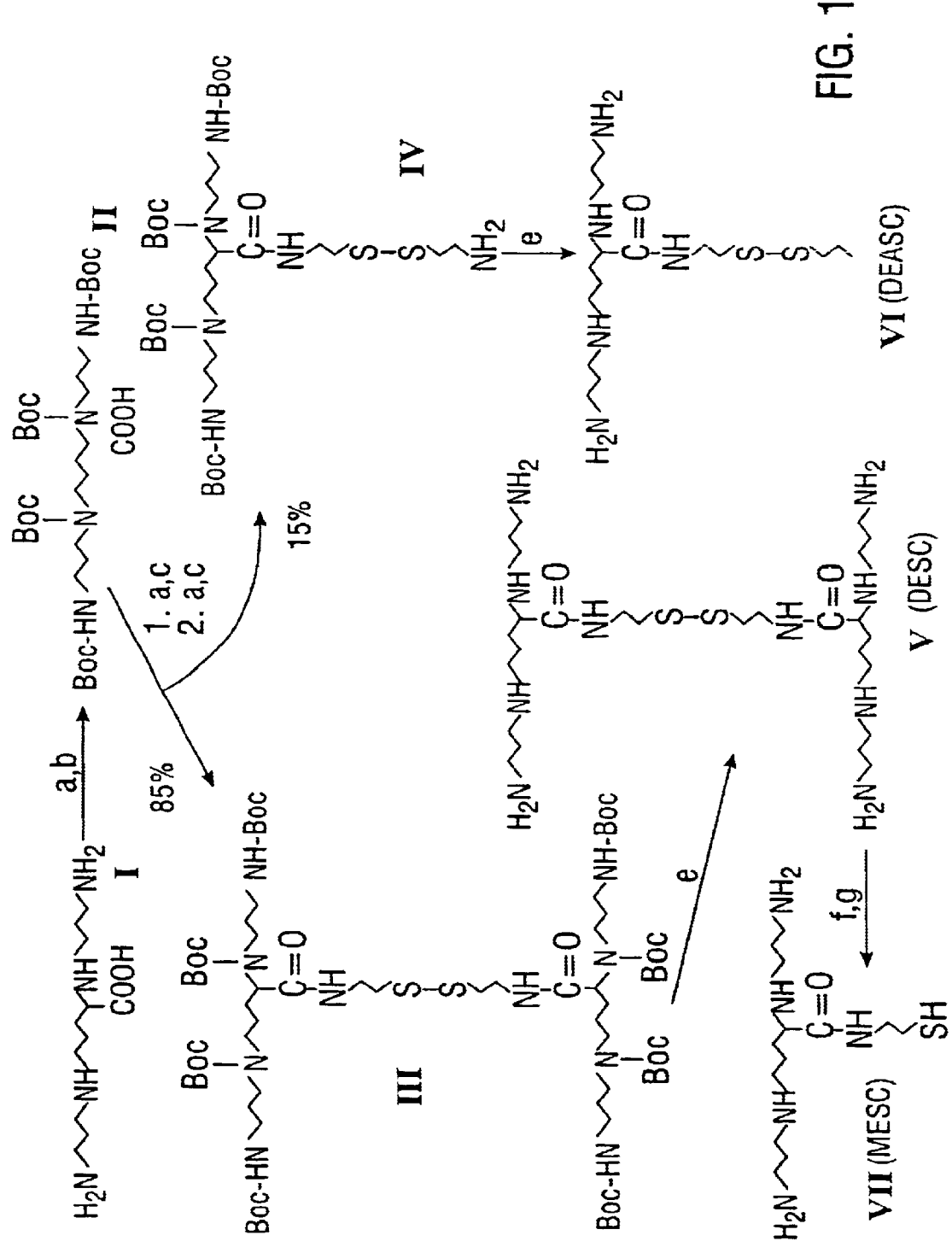
FIG. 1 illustrates details of the synthesis of the compounds of the present invention, wherein a=triethylamine, b=di-tert-butyl dicarbonate; c=cyanuric chloride; d=cystamine dihydrochloride; e=3 N HCl; f=dithiothreitol; g=50 mM sodium phosphate in aqueous solution (pH=8.0); and wherein compound I is 5-carboxyspermine; compound II is tetra-Boc-5-carboxyspermine; compound III is 2,2'-dithiobis[N-ethyl-($N^1$, $N^4$, $N^8$, $N^{12}$)-tetra-Boc-spermine-5-carboxamide; compound IV is N-[2,2'-dithio(ethyl, 1'-aminoethyl)]-$N^1$, $N^4$, $N^8$, $N^{12}$-tetra-Boc-spermine-5-carboxamide; compound V is 2,2'-dithiobis(N-ethyl-spermine-5-carboxamide) octahydrochloride (DESC); compound VI is N-[2,2'-dithio(ethyl,1'-aminoethyl)]-spermine-5-carboxamide pentahydrochloride (DEASC) and compound VII is N-(2-mercaptoethyl)spermine 5-carboxamide (MESC) tetrahydrochloride.

Sym-norspermidine, ornithine dihydrochloride and other reagents for organic syntheses were purchased from Aldrich (Milwaukee, Wis.) and Sigma (St. Louis, Mo.). Reversed phase silica gel liquid chromatography was performed with a Lichroprep™ RP-18 $C_{18}$ silica gel column (40–63 μM; BDH, St. Laurent, Qc., Canada) using a gradient of $CH_3CN:MeOH:H_2O$ (25:35:40 to 50:30:20) as eluent. Homogeneity of synthetic products was assessed by thin-layer chromatography performed on 0.20 mm $F_{254}$ silica gel 60 plates or 0.25 mm $F_{254}S$ RP-18 reversed phase silica gel plates (E. Merck, Darmstadt, Germany). FIR spectra were obtained on a Perkin-Elmer 1600 spectrophotometer (FTIR series) and were expressed in $cm^{-1}$. $^1$H and $^{13}$C NMR spectra were recorded with a Bruker AC/F 300 (300 MHz); $^{13}$C were recorded at 75.47 MHz. Chemical shifts (δ in ppm) were referenced to $CDCl_3$ (7.26 ppm for $^1$H and 77.00 ppm for $^{13}$C). Mass spectra (MS) were recorded at the Mass Spectrometry Region Center (University of Montreal, Montreal, Qc., Canada) by fast atomic bombardment mass spectrometry (FABMS) or liquid secondary ion mass spectrometry (LSMIS), using a VG AutoSpecQ™ and a Kratos MS50 TCTA, respectively.

[2,3-$^3$H(N]putrescine dihydrochloride (4.1×10$^4$ Cl/mol) and [1,8-$^3$H(N)]spermidine trihydrochloride (1.5×10$^4$ Cl/mol) were obtained from Dupont-New England Nuclear (Lachine, Qc., Canada). [5,8-$^{14}$C]spermine tetrahydrochloride (108 cl/mol)) was purchased from Amersham (Arlington Heights, Ill.). DFMO was provided by the Marion Merrell Dow Research Institute (Cincinnati, Ohio). Fetal bovine serum (FBS) and Cosmic™ calf serum were from Hyclone (Logan, Utah). The heterobifunctional reagent 1(-p-azidosalicylamido)-4-iodoacetamido)butane (ASIB) as obtained from Pierce (Rockford, Ill.). Lucifer Yellow (OY) iodoacetamide was purchased from Molecular Probes (Eugene, Oreg.). Putrescine dihydrochloride, spermidine trihydrochloride, spermine tetrahydrochloride, iodoacetamide, 5,5'-dithio(2-nitrobenzoic acid) and 3,4-diaminobenzoic acid as well as tissue culture reagents were purchased from Sigma. Ortho-phthaldialdehyde was purchased from Fluka (Ronkonkoma, N.Y.) and other reagents for high-performance liquid chromatography (HPLC) were from Fisher Scientific (Montreal, Qc., Canada) or Aldrich (Milwaukee, Wis.).

Synthesis of 5-Carboxyspermine (Compound I)

Unless otherwise indicated, reactions were performed at room temperature. Compound 1 of FIG. 1, namely 5-carboxyspermine, was synthesized using a known scheme (Behr, J. P. 1989. *J. Chem. Soc. Chem. Commun.* 101–103). Briefly to a stirred solution of 10.0 g (59.3 mmol) of ornithine hydrochloride dissolved in 250 ml MeOH were added 18.0 g (197 mmol) of tetramethylammonium hydroxide. After dissolution of ornithine salt, MeOH was evaporated, the mixture was then dissolved in 350 mL of dry dimethylformamide (HPLC grade; Aldrich, Milwaukee, Wis.) and the residual ammonium salt was filtrated, yielding ornithine as its free base. Following the addition of acrylonitrile (2.2 equivalents, 130.9 mmol), the mixture was stirred for 16 hours in the dark to give 10.6 g (yield=74%) of crude $N^a,N^b$-diethylcyanide ornithine, which was subsequently used without further purification. White solid: IR (film) v cm$^{-1}$ 3372 (OH, acid), 2247 (CN); $^1$H NMR δ (CDCl$_3$ 300 MHz) 1.48 (m, 4H, C$\underline{H}_2$CHCOOH), 2.63 (m, 6H, 3×C$\underline{H}_2$N), 2.86 (2xt, J$_1$=5.9 and J$_2$-2.7 Hz, 4H, 2×CH$_2$CN), 3.07 (t, J=7.2 Hz, 1H, C$\underline{H}$COOH). To obtain 5-carboxyspermine KOH (2.7 g, 48.0 mmol) was dissolved with vigorous stirring in 8 ml of 95% (v/v) EtOH and 10.5 g (44.1 mmol) of $N^a,N^b$-diethylcyanide ornithine were then added. The resulting mixture was placed under H$_2$ at 40 psi in a Burgess-Parr hydrogenator, using 2.09 g (24.4 mmol) or Raney nickel as catalyst (Behr, J. P. 1989. *J. Chem. Soc. Chem. Commun.* 101–103; Bergeron, R. J. and Garlich, J. R. 1984. *Synthesis:* 782–784). After 22 hours, Raney nickel was removed by filtration, and the solvent evaporated in vacuo, yielding 16.07 g of crude 5-carboxyspermine potassium salt. Yellow oil; IR (film) v cm$^{-1}$ 3363 (OH, acid), 2937 (NH$_2$) no cyanide band; $^1$H NMR δ (CDCl$_3$, 300 MHz) 1.53 (m, 2H, C$\underline{H}_2$NH$_2$), 2.65 (m, βH, C$\underline{H}_2$NH), 3.09 (t, J=5.7 Hz, 1H, C$\underline{H}$COOH).

Synthesis of 2,2'-Dithiobis(N-Ethyl-Spermine-5-Carboxamide) (DESC) and N-[2,2]-Dithio(Ethyl, 1'-Aminoethyl)/spermine-5-Carboxamide (DEASC)

Amine protection of 5-carboxyspermine by tert-butyl carbonyl (Boc) groups was performed as described (Ponnusamy, E., Fotadar, U., Spisni, A. and Fiat, D. 1986. *Syntheses:* 48–49). To 16.0 g (65.0 mmol) of crude 5-carboxyspermine potassium salt dissolved in 1.5 L MeOH were added 9.64 ml of 10% (v/v) triethylamine and 54.3 g (4.4 equivalents, 286 mmol) of di-tert-butyl dicarbonate. After stirring for 24 hours, solvent was evaporated, 100–150 ml H$_2$O were added and the resulting mixture was chilled at 0° C. After adjusting pH at 2.2 with 2 N HCl, the Boc-product was extracted with ethyl acetate, dried over anhydrous MgSO$_4$ and purified by C$_{18}$ reversed phase silica gel chromatography, yielding 3.3 g of pure tetra-Boc-5-carboxyspermine (Compound II, FIG. 1). Light yellow solid; IR (film) v cm$^{-1}$ 3356 (OH, acid), 1682 (C=O, amide); $^1$H NMR δ (CDCl$_3$, 300 MHz) 1.32 (2xs, 36 H, (C$\underline{H}_3$)$_3$C from Boc-N), 1.90–1.40 (m, 9H, C$\underline{H}_2$CH$_2$N), 3.20–2.90 (m, 10H, C$\underline{H}_2$N); M (for C$_{31}$H$_{58}$O$_{10}$N$_4$)–646.41; m/z (LSIMS)=647.42 [(M+1)*]. Coupling of tetra-Boc-5-carboxyspermine (compound II) to cystamine was then performed in two steps based on the method of Venkataraman (Venkataraman, K. 1979. *Tetrahedr. Lett.* 32, 3037). To a solution of 1.15 g (1.78 mmol) of compound II in 20 ml dry acetone was added 0.27 mL (1.1 eq, 1.96 mmol) of triethylamine (freshly distilled on KOH) and 361 mg (1.1 eq, 1.96 mmol) of cyanuric chloride and the reaction mixture stirred overnight under N$_2$ to form the corresponding acid chloride. Cystamine dihydrochloride (241 mg; 1.07 mmol) was then suspended in dry triethylamine and added to the acid chloride form of compound II, with the resulting triethylamine concentration being at ≧4-fold excess relative to the latter. After stirring for 12 hours, the residual triazine oxide was filtrated, acetone was evaporated and the product extracted with CHCl$_3$, dried over anhydrous MgSO$_4$ and evaporated in vacuo. The crude compound was then purified by reversed-phase C$_{18}$ column chromatography, yielding 0.682 g of 2,2'-dithiobis[N-ethyl-(N$^1$,N4,N$^c$,N$^{12}$-tetra-Boc-5-carboxamide (compound IV, FIG. 1). (m) Yellow oil; IR (film) v cm$^{-1}$ 1693 (C=O, amide); $^1$H NMR δ (CDCl$^3$, 300 MHz) 1.38 (s, 36H, (C$\underline{H}_3$)$_3$C), 1.59 (m, 8H, CH$_2$C$\underline{H}_2$CH$^2$), 2.53 (6, J=5.7 Hz, 1H, CONH$\underline{H}$CH$_2$), 2.73 (t, J=6.1 Hz, 2H, C$\underline{H}_2$S), 3.11 (m, 10H, C$\underline{H}_2$NH), 3.51 (m, 2H, NCH$_2$CH$_2$S):M (for C$_{xx}$H$_{123}$O$_{18}$N$_{10}$S$_2$)=1408.85; m/z (FABMS)=1409.9 [(M+1)*].

Compound III (215 mg in MeOH) was then deprotected by addition of 1 ml of 3 N HCl, bringing the pH from 6.0 to =0.5. After stirring vigorously for 15 hours, the solvent was dried out in vacuo and the resulting compound purified by cation exchange chromatography with a Dowex 50W-X4 column (dry mesh; 100–200; Sigma) pre-equilibrated with H$_2$O and successively washed with H$_2$O, 1 N HCl, 2 N HCl, 4 N HCl and 6N HCl. Ninhydrin-positive fractions eluted with 6 N HCl were pooled and evaporated in vacuo, yielding 96 mg of pure 2,2'-dithiobis(N-ethyl-spermine-5-carboxamide)-octahydrochloride (DESC, Compound V, FIG. 1. White solid; mp 75–78° C.; bp 118° C. $^1$H NMR δ (CDCl$_3$, 300 MHz) 1.62 (m, 2H, C$\underline{H}_2$CHCONH), 1.97–1.80 (m, 6H, C$\underline{H}_2$CH$_2$CH$_2$), 2.74 (t, J=6.2 Hz, 2H, C$\underline{H}_2$S), 2.92 (m, 10H, C$\underline{H}_2$HN), 3.46 (dt, J=7.1 Hz, 2H, C$\underline{H}_2$CH$_2$S), 3.84 (t, J=7.0 Hz, 1H, C$\underline{H}$CONH); M (for C$_{25}$H$_{60}$O$_2$N$_{10}$S$_2$)=608.96; m/z (FABMS)=609.4 (M*).

Compound IV was similarly deprotected to yield N-[2,2'-dithio(ethyl, 1'-aminoethyl)]spermine-5-carboxamide (DEASC, Compound VI, FIG. 1). Yellow solid; mp 50–54° C.; bp 109° C. 1H NMR δ (CDCl$_3$, 300 MHz) 1.89 (m, 2H, C$\underline{H}_2$CHCONH), 2.10–2.29 (m, 6H, C$\underline{H}_2$CH$_2$CH$_2$), 3.04 (t-J=6.0 Hz, 2H, CONHC$\underline{H}_2$CH$_2$S), 3.19 (t, J=7.4 Hz, 2H, SSCH$_2$C$\underline{H}_2$HN$_2$), 3.25 (m, 10H, C$\underline{H}_2$, NH), 3.51 (t, J=6.5 Hz, 2H, SSCH$_2$C$\underline{H}_2$HN$_2$), 3.78 (m, 2H, CONHC$\underline{H}_2$CH$_2$S), 4.11 (t, J=6.7 Hz, 1H, C$\underline{H}$CONH), M (for C$_{15}$H$_{41}$ON$_5$S$_2$)=380.62; m/z (LSIMS)=381.24.

Synthesis of N-(2-Mercaptoethyl)spermine-5-Carboxamide [MESC]

DESC was dissolved in 50 mM sodium phosphate bugger, pH 8.0, containing 250 mM dithiothreitol (DTT), and incubated for 30 minutes at 37° C. in a water bath. The mixture was then loaded on a Dowex™ 50W-X4 cation exchange column equilibrated with H$_2$O, and after washing with 5 column volumes each of 1 N HCl and 2 N HCl, the free thiol was eluted with 10 volumes of 4 N HCl. Amine-containing fractions, as identified by mixing 5 μl aliquots with 200 μl of an o-phthaldialdehyde solution (3.7 mM o-phthaldialdehyde; 0.4 M boric acid, pH 10.4; 1% v/v MsOH; 0.45% v/v 2-mercaptoethanol; 0.03% w/v Bri? 35) and hearing for 20 minutes at 37° C., were then pooled. The amount of N-(2-mercaptoethyl)-spermine-5-carboxamide [MESC] tetrahydrochloride (compound VII, FIG. 1) thus isolated was titrated for thiol equivalents with 5,5'-dithiobis-(2-nitrobenzoic acid) (Jocelyn, P. C. 1987. *Meth. Enzymol.* 143, 44–67) using either cysteamine or DTT as standard. The yield of MESC using this procedure was virtually 100%, based on the number of thiol equivalents determined with 5,5'-dithio-bis-(2-nitrobenzoic acid) and the expected number of thiol equivalents expected per mass of DESC. Finally, MESC purity was configured by ion-pair reversed-phase HPLC using post-column derivatization with o-phthaldialdehyde (Pegg, A. E., Wechter, R., Poulin, R., Woster, P. M. and Coward, J. K. 1989. *Biochemistry* 28: 8446–8453). $^1$NMR δ (CDCl$_3$, 300 MHz) 1.91 (m, 2H, C$\underline{H}_2$CHCONH), 2.08–2.24 (m, 6H, CH$_2$C$\underline{H}_2$CH$_2$), 2.82 (t, J=6.3, 2H, CON HCH$_2$C$\underline{H}_2$SH), 3.22 (m, 10H, C$\underline{H}_2$NH, 3.56 (m, 2H, CONHC$\underline{H}_2$CH$_2$SH), 4.11 (t, J=6.6, 1H, C$\underline{H}$CONH).

Synthesis of Thioester Adducts of MESC with Iodoacetamides

To 1 ml of an extemporaneously prepared, DTT-free solution of MESC (20 mM in H$_2$) were added 50 μl of 50 mM Tris-HCl (pH 7.0) and 105 μl of a 40 mM solution of either iodoacetamide, LY iodoacetamide or ASIB in a light-protected microcentrifuge tube, and the mixture was incubated for 2 hours at 37° C. The extent of thiol modification was assessed by measuring the amount of thiol remaining at the end of the incubation with 5,5'-dithio-bis-(2-nitrobenzoic acid) as described above, and was determined to be essentially complete. Excess iodoacetamide was then inactivated by adding DTT to a final concentration of 40 mM and incubating the solution for 2 hours at 37° C. The resulting solutions of MESC adduct was used without further purification for [$^3$H]spermidine uptake assays conducted as described below. The effect of the respective DTT-inactivated iodoacetamide on spermidine transport was determined in parallel by incubating cells with the same reaction mixture from which MESC was omitted.

Cell Culture

Both ZR-75-1 human breast cancer cells and Chinese hamster ovary cells (CHO-K1) were obtained from the American Type Culture Collection (Rockville, Md.). ZR-75-1 cells were maintained in phenol red-free RPMI 1640 medium supplemented with 10% fetal bovine serum, 2 mM L-glutamine, 1 mM sodium pyruvate, 15 mM Hepes, 10 nM 17β-estradiol, and antibiotics [MEZR medium] (Huber, M. and Poulin, R. 1995. *Cancer Res.*, 55, 934–943). CHO-K1 cells were routinely grown in α-Minimal Essential Medium supplemented with 10% Cosmic™ calf serum in a 5% CO$_2$ humid atmosphere at 37° C.

Even though the present invention has been described with a certain degree of particularity, it is evident that many alternatives, modifications, and variations will be apparent to those skilled in the art in light of the following disclosure. Accordingly, it is intended that all such alternatives, modifications, and variations which fall within the spirit and the scope of the invention be embraced by the defined claims.

EXAMPLE 1

Effect of Inhibitors on Cell Proliferation

For growth studies, ZR-75-1 cells were cultured in MEZR medium or in phenol red-free RPMI 1640 supplemented with 2 mM L-glutamine, 1 mM sodium pyruvate, 15 mM Hepes, antibiotics, 1 nM 17β-estradiol, 0.5 μg of bovine insulin per ml and 5% (v/v) charcoal-treated fetal bovine serum (SD medium), as indicated in the text. When polyamines or polyamine analogs were added to serum-containing media, 1 mM aminoguanidine was added to inhibit bovine serum amine oxidase (BSAO) activity (Morgan, D. M. L. 1989, in *The Physiology of Polyamines* (Bachrach, U., and Heimer, Y. M. eds) Vol. I, pp. 203–229, CRC Press, Boca Raton). The effect of the transport inhibitors on cell growth was measured by incubating ZR-75-1 cells for 11 days in medium supplemented with antagonist, polyamines and/or 1 mM DFMO as indicated, followed by colorimetric determination of DNA content with 3,4-diaminobenzoic acid (Simard, J., Dauvois, S., Haagensen, D. E., Lévesque C., Mérand, Y. and Labrie, F. 1990. *Endocrinology* 126: 3223–3231). Medium was changed every other day in these experiments because of the slow reaction of the compound with an unknown component present in the IMEM and RPMI 1640 medium formulation.

Polyamine Analysis

ZR-75-1 cells were plated in 100 mm culture dishes at 5×10$^5$ cells/dish in MEZR medium and grown for 5 days with medium changes every other day. Fresh MEZR medium containing the indicated concentration of transport antagonist was then added, plus or minus 200 μM cycloheximide (CHX), and cells were incubated for 1 or 6 hours. Medium was then removed, cell monolayers rinsed twice with 10 ml of ice-cold Ca$^{2+}$/Mg$^{2+}$-free phosphate buffered-saline (PBS) (2.7 mM KCl; 1.5 mM KH$_2$PO$_4$; 8.1 mM Na$_2$HPO$_4$; 137 mM NaCl), and harvested by centrifugation (2000×g×90 s at 4° C.) following a 5- to 7-minute-incubation with bovine trypsin/EDTA solution (0.05%/ 0.02%, w/v) in Hanks' Balanced Salt Solution (Huber, M. and Poulin, R. 1995. *Cancer Res.* 55; 934–943). Cell pellets were resuspended in 300 μl of 10% (v/v) trichloroacetic acid or Tris-DTT buffer (50 mM Tris/HCl, 0.1 mM EDTA, 5 mM DTT, pH 7.5) and stored at −20° C. until further analysis. For chromatographic analysis, samples were first quickly thawed and incubated for 15 minutes at 37° C. Trichloroacetic acid was then added to DTT-containing samples to a final concentration of 10% (wt/v). Samples were dispersed for 2 minutes in a sonicating water bath, and pelleted in a microcentrifuge for 5 minutes. The trichloroacetic acid-insoluble pellet was solubilized in 300–500 μl of 1 N NaOH and used to determine protein content using bovine serum albumin (fraction V) as standard. Polyamine contents were then analyzed by ion pair reverse-phase HPLC with fluorometric detection after postcolumn derivatization with o-phthaldialdehyde as described (Pegg, A. E., Wechter, R., Poulin, R., Waster, P. M., and Coward, J. K. 1989. *Biochemistry* 28: 8446–8453; Huber, M., and Poulin, R. 1996. *Cancer Res.*, 55: 934–943). In this system, putrescine, spermidine, spermine, MESC and DEASC were resolved with retention times of 18.5, 31.0, 35.0, 36.5, 37.5, and 44.0 minutes respectively.

DESC Stability

DESC stability was tested by incubating the compound dissolved (at 50 μM) in PBS or in IMEM medium containing 10% (v/v) fetal bovine serum plus or minus 1 mM aminoguanidine in a humid 5% CO$_2$ atmosphere at 37° C. and in the absence of cells. At indicated times, trichloroacetic acid was added to aliquots of this solution to a final concentration 10% (w/v) and the samples directly analyzed by HPLC as above.

Determination of Polyamine Uptake Activity

The rate of putrescine and spermidine transport was determined in ZR-75-1 cells incubated in serum-free RPMI 1640 medium as described (Lessard, M., Zhao, C., Singh, S. M. and Poulin, R. 1995. *J. Biol. Chem.* 270: 1685–1694), using [$^3$H]putrescine (30 Ci/mol) and [$^3$H]spermidine (20 Ci/mol), respectively as substrates for a 20 minute-assay period. Spermine uptake was similarly determined, using 1 μM [$^{14}$C]spermine (32 Ci/mol) as substrate. Uptake activity was expressed per amount of DNA as fluorometrically determined using 3,4-diaminobenzoic acid (Simard, J., Dauvois, S., Haagensen, D. E., Lévesque, C., Mérand, Y. and Labrie, F. 1990. *Endocrinology,* 126: 3223–3231). For the determination of spermidine uptake activity in CHO-K1 cells, 80% confluent cell monolayers were rinsed twice with PBS and incubated for 20 minutes at 37° C. in 400 µl of buffer A (20 mM Tris-HCl, pH 7.4; 0.42 mM CaCl$_2$; 0.41 mM MgSO$_4$; 103 mM NaCl; 5.7 mM KCl; 1.1 mM D-glucose) containing 5 µM [$^3$H]spermidine (20 Ci/mol). Cell cultures were then washed twice with 1 ml PBS containing 5.7 mM sym-norspermidine. Cells were then lysed with 200-µl aliquot of 1 N NaOH and incubated for 30 minutes at 60° C. After neutralization with 200 µl of 1 N HCl, radioactivity was determined from a 250-µl of the cell lysate by scintillation counting. Uptake activity was expressed per amount of total cellular protein as determined by the method of Bradford (Bradford, M. M. 1976. *Anal. Biochem.* 72: 248–254). Non-specific binding of radioactive substrate was similarly determined in parallel for both cell lines after a 15 second-incubation with 400 µl of ice-cold uptake solution.

Kinetic Analyses

Kinetic analysis of polyamine transport was performed by determining uptake activity in the presence of a 3 µM [$^3$H]putrescine or 1 µM [$^3$H]spermidine plus increasing concentrations of nonradioactive substrate. $K_{??}$ $K_i$ and $V_{max}$ values were then estimated by Lineweaver-Burke analysis. For competitive inhibitors, $K_i$ values were also estimated by measuring uptake activity in the presence of logarithmically increasing concentrations of antagonist, and using the Cheng-Prusoff equation (Cheng, Y.-C. and Prusoff, W. H. 1973. *Biochem. Pharmacol.* 22: 3099–3108) by iterative curve fitting for a sigmoidal curve. For mixed competitive/noncompetitive inhibition, two methods were used to calculate kinetic constants. First, the equation $$V = \frac{V\,max}{\dfrac{K_m}{S}\left(1 + \dfrac{i}{k_1}\right) + \left(1 + \dfrac{i}{k'_1}\right)}$$

where v, s, and i are the transport velocity, substrate concentration and inhibitor concentration respectively, was used to calculate the inhibition constants for inhibitor/carrier complex formation ($K_i$) and carrier/inhibitor/substrate complex formation ($K_i'$) (Dixon, M. and Webb, E. C. 1976. *Enzymes*, 3rd Ed., Academic Press, San Diego, Calif.). Alternatively, the value of $K_i$ for a mixed competitor/noncompetitor was estimated from the intersect of equations $v^{-1}$ vs i at two different substrate concentrations (Dixon, M. and Webb, E. C. 1976. *Enzymes*, 3rd Ed., Academic Press, San Diego, Calif.).

Intracellular Accumulation

The time course of intracellular accumulation of spermidine in the presence of transport antagonists was determined by incubating ZR-75-1 cells in 24-well plates with DESC (50 or 200 µM) or MESC (200 µM) in dissolved in MEZR medium containing 5 µM [$^3$H]spermidine in the presence or absence of cycloheximide (CHX, 200 µM), and harvesting at the indicated times for the determination of intracellular radioactive contents, as described above for polyamine uptake assays.

Statistical Analysis

Statistical significance of differences between means was assessed by unpaired Student's t-tests. Unless otherwise indicated, results are expressed as means±SD of determinations from triplicate cell cultures.

Design and Synthesis of DESC, DEASC and MESC

The original rationale for synthesizing MESC (Compound VII of FIG. 1) was to generate an affinity reagent with a thiol side chain that could be derivatized with fluorescent or radioactive sulfhydryl reagents to label the polyamine transporter. The precursor chosen for the synthesis, namely 5-carboxyspermine, has been previously used to prepare lipopolyamines for efficient DNA transfection (Behr, J. P. 1989. *J. Chem. Soc. Chem. Commun.* 101–103; Behr, J. P., Demeneix, B., Loeffler, J.-P. and Perez-Mutul, J. 1989. *Proc. Natl. Acad. Sci. USA* 86: 6982–6986), and more recently, as a photoaffinity reagent to label the polyamine-binding site of casein kinase 2 (Leroy, D., Schmid, M., Behr, J.-P., Filhol, O., Pares, S., Garin, J., Bourgarit, J.-J., Chambaz, E. M. and Cochet, C. 1995 *J. Biol. Chem.* 270: 17400–17406). The scheme used to prepare MESC involved the coupling of a cystamine bridge through amide bonds with two Boc-protected 5-carboxyspermine molecules to form DESC after removal of the Boc groups (Compound V of FIG. 1), followed by reduction of the DESC disulfide bridge. A small amount (10–15%) of the mixed MESC-cysteamine disulfide (DEASC, Compound VI; FIG. 1) was also generated in the coupling process. Complete separation of DEASC from DESC on a preparative basis proved to be difficult even using ion exchange chromatography (data not shown). Consequently, most DESC preparations contained a small amount (1–2%) of DEASC after reversed-phase liquid chromatography on C$_{??}$ silica gel. DESC and DEASC were stable for months in aqueous solutions buffered at pH=7.0, whereas MESC solutions were supplemented with DTT to prevent oxidation.

Figure 2:
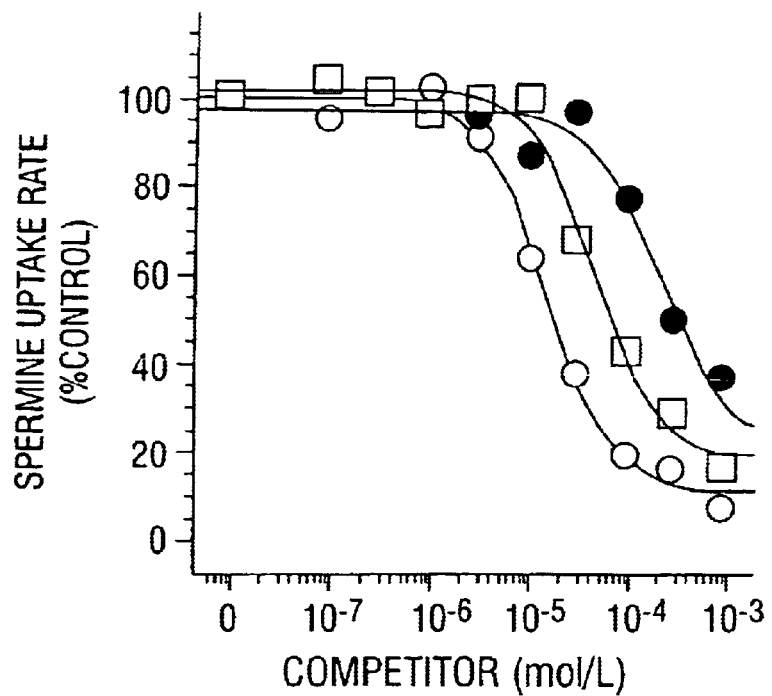
FIG. 2 graphically illustrates the inhibition of [$^{14}$C] spermine transport by MESC, DESC and DEASC in human ZR-75-1 breast cancer cells. The rate of spermine uptake was measured in ZR-75-1 cells grown as monolayers in 24-well culture plates in the presence of the indicated concentrations of DESC (○), MESC (●), and DEASC (□), using 1 μM [$^{14}$C]spermine as substrate. Data are the mean±SD of triplicate determinations.
Figure 3A:
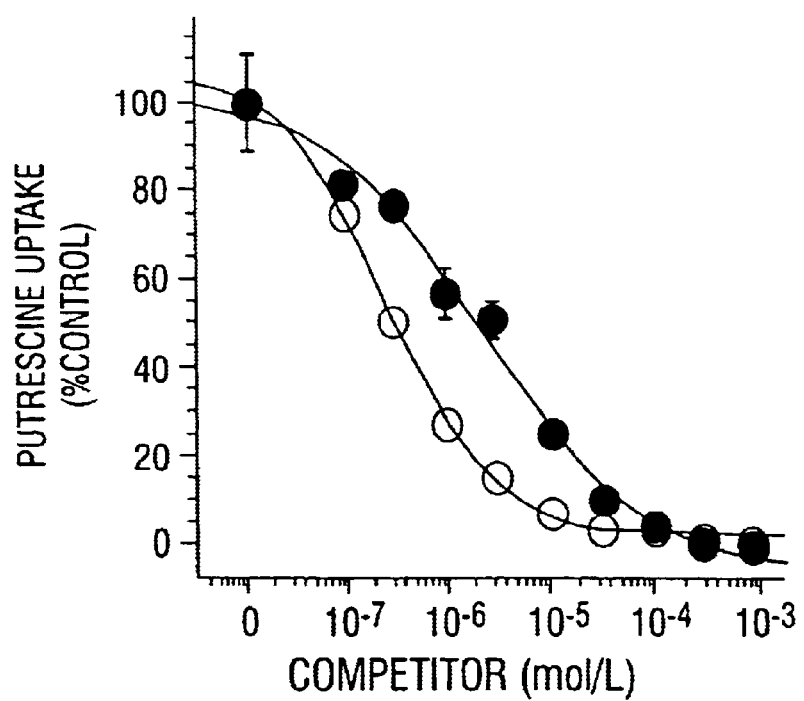
FIG. 3 graphically illustrates the inhibition of [$^3$H] spermidine uptake by spermine and DESC in ZR-75-1 cells. The rate of spermidine uptake was measured in ZR-75-1 cells grown as monolayers in 24-well culture plates in the presence of the indicated concentrations of spermine (○) and DESC (●) using 3 μM [³H]putrescine (A) or 1 μM [³H]spermidine (B) as substrate. Data are the mean±SD of triplicate determinations from a representative experiment.
Figure 3B:
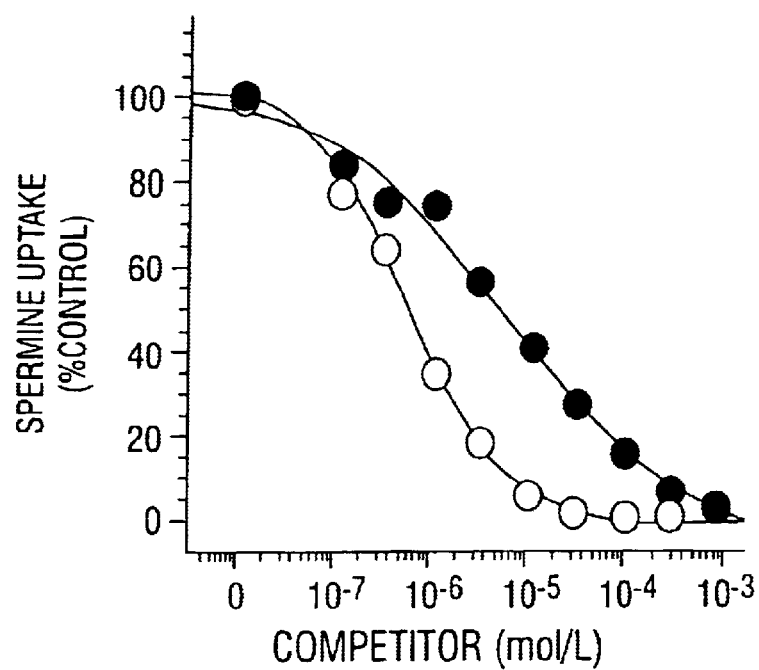
Figure 4A:
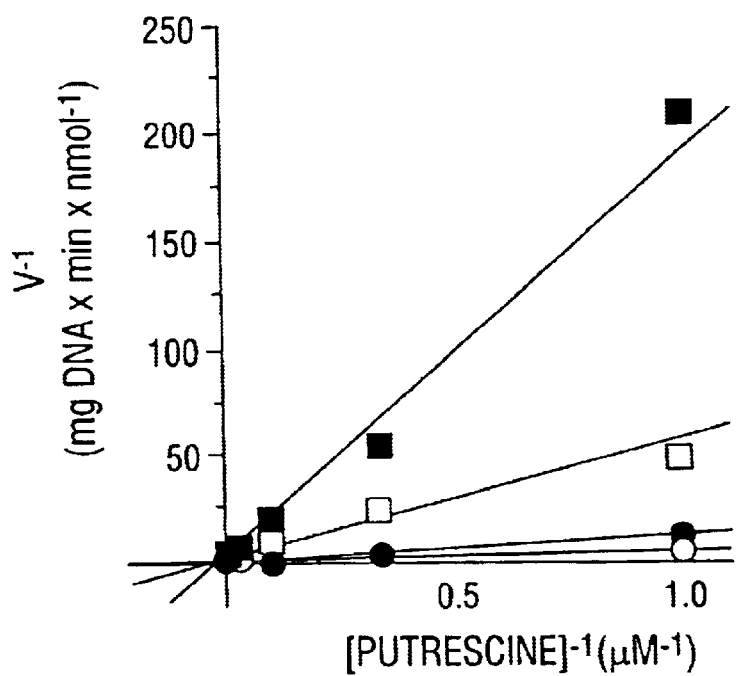
FIG. 4 illustrates graphically the Lineweaver-Burke analysis of putrescine transport inhibition by DESC and DEASC in ZR-75-1 cells. The rate of [³H]putrescine uptake was determined in ZR-75-1 cell cultures with increasing concentrations of substrate (A) in the presence of 0 μM DESC (○), 3 μM DESC (●), 30 μM DESC (□) or 100 μM DESC (■) or (B) in the presence of 0 μM DEASC (○), 20 μM DEASC (●), 50 μM DEASC (□) or 200 μM DEASC (●)
Figure 4B:
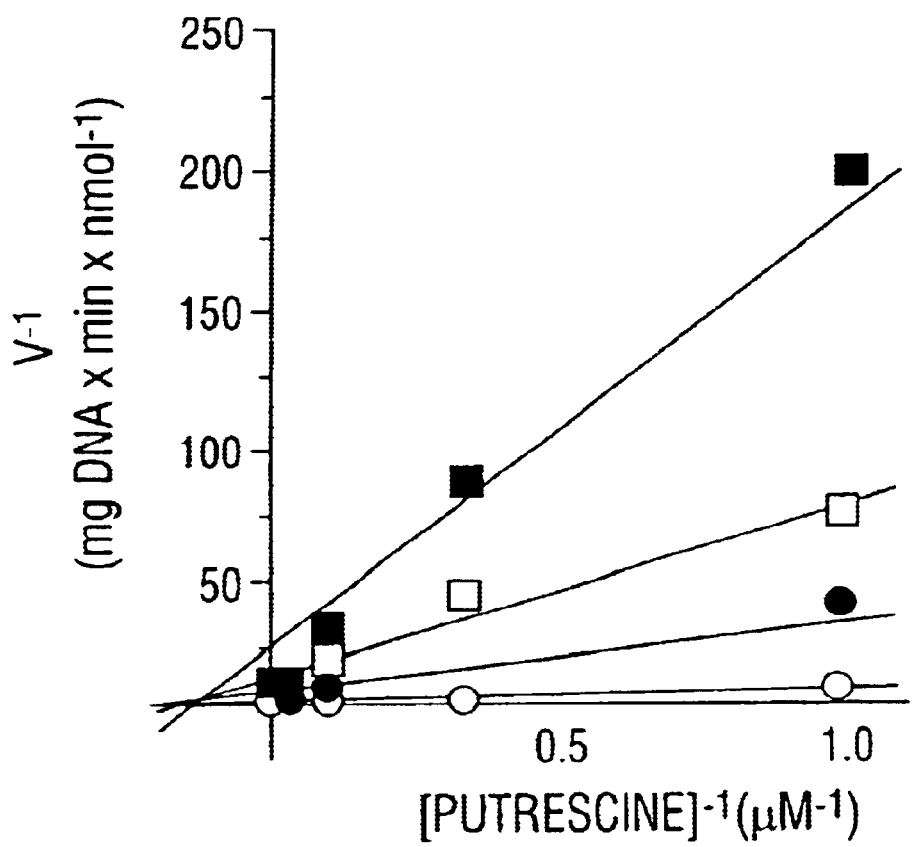

Affinity of DESC, DEASC and MESC for the Mammalian Diamine and Polyamine Transport In order to evaluate the suitability of the spermine conjugates as prospective affinity ligands, their relative ability to inhibit putrescine and polyamine uptake was evaluated. As shown in FIG. 2, DESC was the most potent antagonist of [$^{14}$C]spermine transport in ZR-75-1 cells, with a $K_i$ value about 5-fold and 16-fold lower than that of DEASC and MESC, respectively. The ability of spermine to compete against [$^3$H]putrescine and [$^3$H]spermidine uptake was in fact only about 7-fold higher than that of DESC (FIG. 3). DESC (FIG. 4A) and MESC (data not shown) were pure competitive inhibitors of [$^3$H]putrescine uptake at concentrations up to 100 and 200 µM, respectively. On the other hand, inhibition of putrescine transport by DEASC belonged to a mixed competitive/non-competitive type (FIG. 4B). Table I summarizes the $K_i$ values determined for DESC, MESC and DEASC toward putrescine, spermidine and/or spermine uptake, in relation with the mutual transport interactions between the latter substrates. Notably, $K_i$ values of the three spermine conjugates with respect to putrescine uptake were 3-fold to 5-fold higher than for spermine uptake, unlike spermidine and spermine which both inhibited the uptake of either substrate with similar potency, and with a $K_i$ roughly equal to their $K_m$ as substrate.

TABLE I $K_i$ Values of Inhibition of Diamine and Polyamine Transport by MESC, DESC and DEASC in ZR-75-1 Cells

| | $K_m$ or $K_i$ (µM) | | |
|---|---|---|---|
| Compound | Putrescine | Spermidine | Spermine |
| Putrescine | 3.7 ± 0.4[a] | 125 ± 29[a] | 0.23 ± 0.13[a,b] |
| Spermidine | 0.23 ± 0.05[a] | 0.49 ± 0.15[a] | 0.37 ± 0.09[a] |
| Spermine | 0.33 ± 0.02[a] | ND | 0.20 ± 0.06[g] |
| DESC | 1.6 ± 0.5[b] | 2.7 ± 1.1[b] | 5.0 ± 0.7[b] |
| MESC | 22 ± 3[b] | ND | 80 ± 31[b] |
| DEASC | 5.3 ± 0.6 ($K_i$)[c] 4.1 ± 0.5 ($K_i'$) | ND | 16 ± 3[d] |

Data annotated with a are from Lessard, M., Zhao, C., Singh, S. M., and Poulin, R. 1995. *J. Biol.* 270: 1685–1694, b indicates data obtained with this work; mean±SD of triplicate determinations from 2 to 4 different experiments; c corresponds to values of inhibition constants for carrier/inhibitor complex formation ($K_i$) and for carrier/inhibitor/putrescine complex formation ($K_i'$) assuming a mixed competitive/non-competitive model; mean±SD of triplicate determinations at 3 three inhibitor concentrations at two different substrate concentrations for a series of increasing inhibitor concentrations (Dixon, M, and Webb, E. C. 1976. *Enzymes,* 3rd Ed., Academic Press, San Diego, Calif.).

The relative potency of DESC and MESC as competitive inhibitors of polyamine uptake was also evaluated in CHO-K1 cells, in which they respectively exhibited $K_i$ values of 0.92±0.15 and 33.6±7.2 $\mu$M (FIG. 5).

EXAMPLE 2

Effect of Side Chain Length and Substituents on Spermidine Transport Inhibition by MESC Derivatives The observation that MESC was a less potent inhibitor of diamine and polyamine transport than DESC and DEASC suggested that the nature of the side chain strongly influences the interaction of these compounds with the carrier. The thiol side chain of MESC was thus derivatized with substituting groups of different sizes and charges through thioether linkage with three different iodoacetamides, namely LY iodoacetamide, ASIB and iodoacetamide itself, and the ability of the resulting complexes (MESC-LY, MESC-ASIB, and MESC-acetamide, respectively) to inhibit spermidine uptake was then evaluated. These studies were conducted using CHO-K1 cells. As shown in FIG. 5, derivatization of the thiol group of MESC did not significantly (P>0.10) increase the $K_i$ toward spermidine uptake for the three conjugates studied. In the case of MESC-ASIB, Ki values might have been underestimated by partial inactivation of the polyamine carrier at the assay temperature, although the uptake reaction was conducted under subdued lighting. Thus, the results show that specific recognition of the spermine head of MESC can accommodate considerable variation in length, size, polarity or charge for the side chain without detrimental effect on its affinity for the polyamine carrier. Consequently, inhibitors having different side chains, while maintaining their inhibitory activity on polyamine transport are also encompassed by the present invention.

EXAMPLE 3

Lack of Permeation of DESC and MESC through the Polyamine Transport System

The ability of ZR-75-1 cells to accumulate DESC and MESC was determined. Since DESC was eluted as a late, broad peak in the HPLC system used, DTT was added to cell extracts to reduce DESC to MESC and decrease the detection threshold. Results are shown in Table II. ZR-75-1 cells were incubated for 1 or 8 hours in MEZR medium in the presence of 50 or 200 $\mu$M DESC or MESC prior to determination of polyamine contents. CHX was added at 200 $\mu$M where indicated. Other details are provided under "Materials and Methods." Values are the mean±SD of triplicate determinations from 2 independent experiments.

TABLE II

Intracellular Accumulation of DESC and MESC in ZR-75-1 Cells

| Addition | Time (h) | Polyamine intracellular contents (nmol/mg protein) | | | |
|---|---|---|---|---|---|
| | | Spermidine | Spermine | DESC | MESC |
| Control | 1 | 0.69 ± 0.08 | 8.22 ± 0.48 | — | — |
| | 6 | 0.91 ± 0.07[a] | 9.16 ± 0.13 | — | — |

TABLE II-continued

Intracellular Accumulation of DESC and MESC in ZR-75-1 Cells

| Addition | Time (h) | Polyamine intracellular contents (nmol/mg protein) | | | |
|---|---|---|---|---|---|
| | | Spermidine | Spermine | DESC | MESC |
| +50 $\mu$M DESC | 1 | 0.81 ± 0.14 | 8.27 ± 0.81 | <0.01 | <0.01 |
| | 6 | 0.73 ± 0.11 | 8.60 ± 0.29 | <0.01 | <0.01 |
| +200 $\mu$M DESC | 1 | 0.79 ± 0.11 | 8.77 ± 0.79 | <0.01 | <0.01 |
| | 6 | 0.76 ± 0.11 | 8.66 ± 0.26 | 0.12 ± 0.01 | <0.01 |
| +200 $\mu$M DESC + CHX | 1 | 0.75 ± 0.04 | 9.57 ± 0.31 | <0.01 | <0.01 |
| | 6 | 0.70 ± 0.03 | 9.55 ± 0.13 | 0.10 ± 0.01 | <0.01 |
| +50 $\mu$M MESC | 1 | 0.95 ± 0.11 | 7.77 ± 0.06 | <0.01 | <0.01 |
| | 6 | 0.75 ± 0.11 | 8.13 ± 0.17 | <0.01 | <0.01 |
| +200 $\mu$M MESC | 1 | 1.15 ± 0.07[a] | 8.93 ± 0.53 | <0.01 | 0.020 ± 0.005 |
| | 6 | 0.81 ± 0.15 | 8.32 ± 0.43 | <0.01 | 0.13 ± 0.06 |

[a]Significantly different (P < 0.5) from control value at time = 1 h. (?)

As shown in Table II, only trace amounts of DESC could be recovered in ZR-75-1 cells after a 6-hour incubation with 200 $\mu$M DESC, but not with 50 $\mu$M, DESC could be detected only after reduction with DTT. These levels represent only about 1.5% of the accumulation measured in ZR-75-1 cells under identical conditions for spermine (Lessard, M., Zhao, C., Singh, S. M. and Poulin, R., 1995. J. Biol. Chem. 270: 1685–1694). Moreover, inhibition of protein synthesis by cycloheximide (CHX), which is known to upregulate polyamine uptake by preventing the synthesis of a polyamine-induced feedback repressor of transport (Lessard, M., Zhao, C., Singh, S. M. and Poulin, R. 1995. J. Biol. Chem. 270: 1685–1694; Mitchell, J. L. A., Diveley, R. R., Jr. and Bareyal-Leyser, A. 1992. Biochem. Biophys. Res. Commun. 186: 81–88), did not enhance DESC internalization, in marked contrast with its effect on spermidine accumulation under similar conditions (FIG. 6B) (Lessard, B., Zhao, C., Singh, S. M. and Poulin, R., 1995. J. Biol. Chem. 270: 1685–1694). Likewise, MESC was accumulated to measurable levels by ZR-75-1 cells only when present at 200 $\mu$M (cf. Table II). Thus, neither DESC or MESC appear to be used as substrates for the polyamine transport system despite the high affinity of the former compound as an antagonist of diamine and polyamine uptake.

EXAMPLE 4

Effect of DESC and MESC on Intracellular Polyamine Accumulation

Figure 6A:
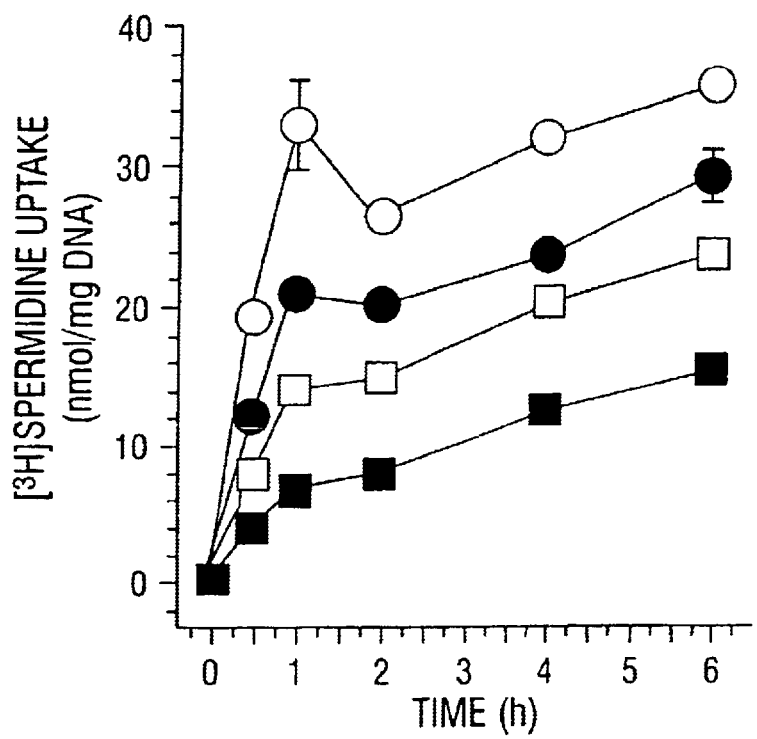
FIG. 6 graphically represents the effect of DESC and MESC on the intracellular accumulation of [³H]spermidine in ZR-75-1 cells, wherein at time 0 (A), 5 μM [³H] spermidine was added to ZR-75-1 cell cultures grown in 24-well plates (1 ml/well) in the presence of 200 μM MESC ( ), 50 μM DESC (□) or 200 μM DESC (●), and accumulation of radio-labeled spermidine determined after the indicated interval. Control cells (○) received vehicle only. B, same as in A, except that 200 μM CHX was added at time 0 in the presence of 0 (●), 50 (□) or 200 μM DESC (●). Data are the mean±SD of triplicate determinations.

The time course of internalization of radio-labeled spermidine was determined in ZR-75-1 cells incubated for up to 6 hours in the presence of the impermeant agonists. As illustrated in FIG. 6A, steady-state [$^3$H]spermidine accumulation in the absence of competitor abruptly reached a near plateau after about 1 hour, which results from the induction of feedback inhibition of polyamine transport (Lessard, M., Zhao, C., Singh, S. M. and Poulin, R., 1995. *J. Biol. Chem.* 270: 1685–1694). MESC and DESC decreased the initial rate of spermidine uptake according to their respective potency as competitive antagonists. Interestingly, spermidine accumulation in the presence of either inhibitor followed a pattern similar to that of control cells, i.e. a rapid phase during the first 60 minutes, followed by a much slower rate of accumulation thereafter, which was nearly independent of antagonist concentration. This pattern suggests that even cellular levels of newly internalized spermidine as low as 20% of those found under control conditions, e.g., in cells treated with 200 $\mu$M DESC, may induce a near maximal degree of feedback repression of polyamine transport.

Figure 6B:
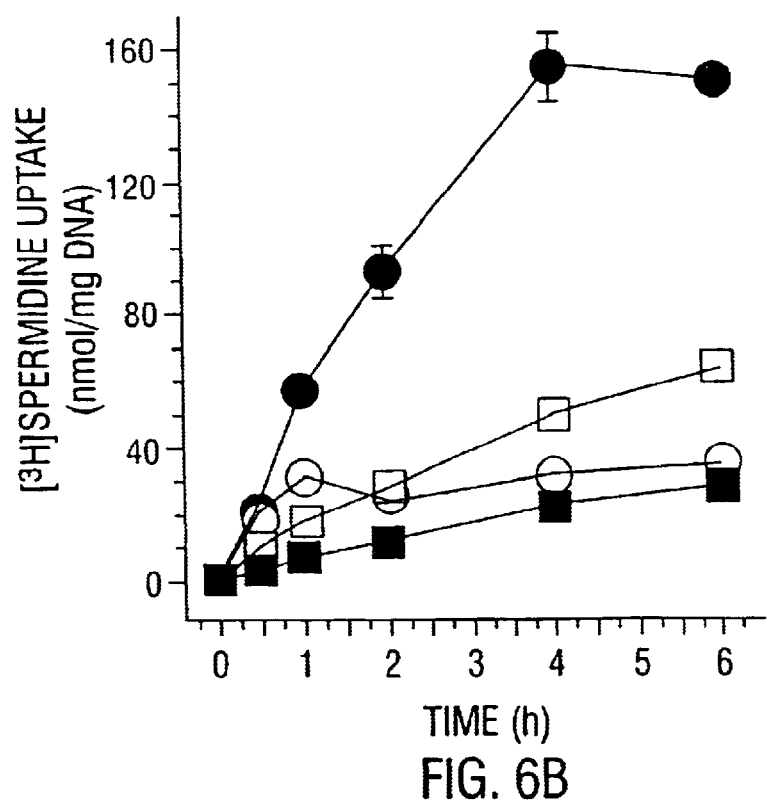

Nevertheless, even a 40-fold excess of the most potent antagonist (i.e. 200 µM DESC) only decreased net spermidine accumulation by only 50% after 6 hours. As previously observed ((Lessard, M., Zhao, C., Singh, S. M. and Poulin, R., 1995. *J. Biol. Chem.* 270: 1685–1694), CHX abolished the induction of feedback transport inhibition, resulting in a 4-fold increase in spermidine accumulation after 4 hours (FIG. 6B). Protein synthesis inhibition also enhanced spermidine accumulation in DESC-treated cells, a finding consistent with the onset of substantial feedback transport repression by subthreshold levels of internalized substrate. Thus, in the absence of the feedback mechanism, the highest concentration of DESC tested (200 µM) decreased net [$^3$H]spermidine accumulation by 80 to 85% after 6 hours and to a level lower than that found in control cells with a fully repressed uptake activity.

EXAMPLE 5

Effect of DESC, DEASC and MESC on Cell Proliferation

Figure 7:
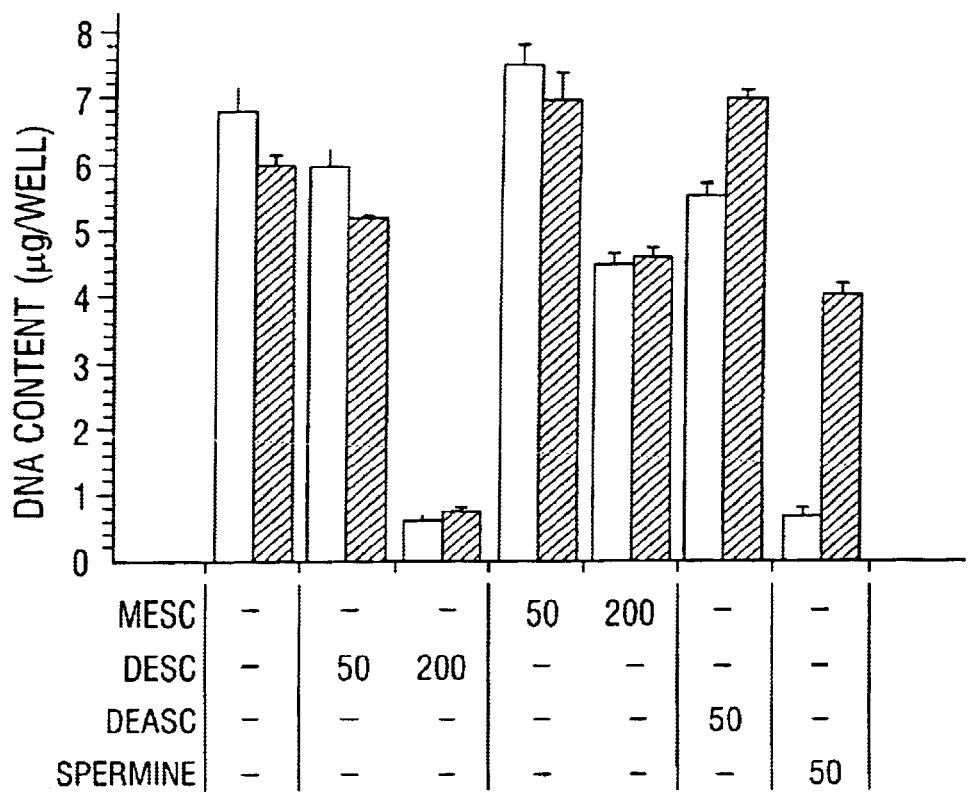
FIG. 7 illustrates the effect of spermine, MESC, DESC and DEASC on ZR-75-1 cell proliferation. Cells were incubated for 11 days in MEZR medium with the indicated concentration of spermine, DESC, MESC, or DEASC in the presence (shaded bars) or absence (plain bars) of 1 mM aminoguanidine, and DNA content per culture was then determined. Data represent the mean±SD of triplicate determinations.

Due to the analogy of the novel transport antagonists with spermine, it might be surmised that they would exhibit significant cytotoxicity like the parent molecule. The marked toxicity of low (<10$^{-3}$M) spermine concentrations in biological media mostly results from catabolism by copper amine oxidases, which generates a dialdehyde, acrolein and H$_2$O$_2$ as deleterious products and can be irreversibly inhibited by carbonyl reagents such as aminoguanidine (Morgan, D. M. L. 1989. in *The Physiology of Polyamines* (Bachrach, U., and Heimer, Y. M. eds) Vol. I, pp. 203–229, CRC Press, Boca Raton). The biocompatibility of DESC, MESC, and DEASC was thus evaluated during a long-term (11-day) incubation with ZR-75-1 cells grown in RPMI 1640 containing 10% (v/v) FBS in the absence and presence of 1 mM aminoguanidine. As shown in FIG. 7, aminoguanidine alone had a slight inhibitory effect on ZR-75-1 cell growth as previously observed (Huber, M. and Poulin, R. 1995. *Cancer Res.* 55: 934–943). Although DESC was only mildly growth inhibitory at 50 µM, there was an abrupt, aminoguanidine-resistant increase in toxicity at 200 µM. In contrast, spermine was acutely cytotoxic at 50 µM, an effect that was only partly prevented by aminoguanidine. MESC was considerably less toxic than its dimer, with a 35% decrease in cell growth at 200 µM which was not blocked by aminoguanidine. On the other hand, 50 µM DEASC caused a 20% inhibition of cell proliferation which could be completely prevented by the amine oxidase inhibitor. Thus, DESC, and to a much lesser degree, its thiol monomer MESC, are cytotoxic toward breast cancer cells at high concentrations through a mechanism that does not involve BSAO. Weak growth inhibition caused by the mixed MESC-cysteamine disulfide, however, apparently involved degradation by a copper amine oxidase.

EXAMPLE 6

Figure 8:
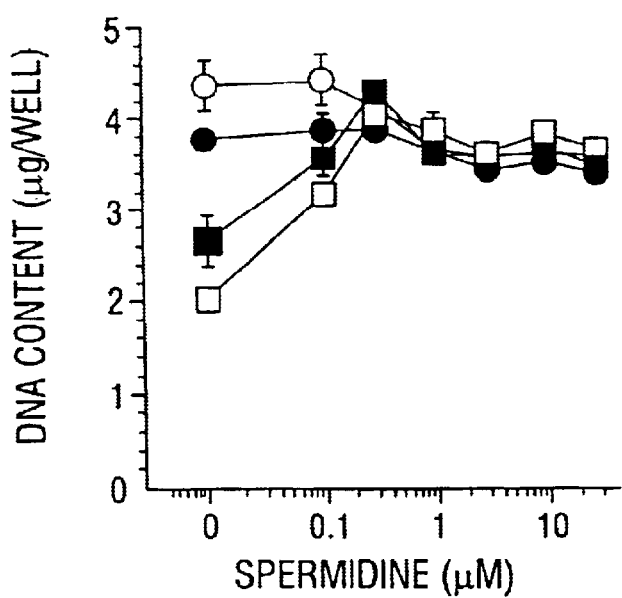
FIG. 8 represents the effect of DESC on the reversal of DFMO-induced growth inhibition by exogenous spermidine in ZR-75-1 cells. Cells were incubated for 11 days in SD medium with the indicated concentrations of spermidine in the presence of 50 μM DESC (●), 1 mM DFMO (□), or the combination thereof (■), or in the absence of drugs (○). Data are the mean±SD of triplicate cultures.

Effect of DESC on Rescue of Demo-induced Growth Inhibition by Exogenous Spermidine Although DESC is indeed a potent antagonist of polyamine accumulation, the slow residual uptake that occurred even at a 40-fold molar excess of inhibitor might be sufficient to counteract polyamine depletion by inhibitors of polyamine biosynthesis. This possibility was assessed by comparing the ability of DESC to prevent the reversal of DFMO-induced growth inhibition by increasing concentrations of exogenous spermidine. At concentrations superior to 0.3 µM, spermidine inhibited ZR-75-1 cell proliferation by up to 20% (FIG. 8). This effect could be due to an incomplete inhibition of BSAO by aminoguanidine (Seiler, N. 1987. in *Inhibition of Polyamine Metabolism. Biological Significance and Basis for New Therapies* (McCann, P. P., Pegg, A. E. and Sjoerdsma, A. eds.), pp. 49–77, Academic Press, Orlando), since it was not observed in media supplemented with equine serum, which does not contain amine oxidase activity (Blaschko, H. and Hawes, R. 1959. *J. Physiol.* 145: 124–131), instead of FBS (data not shown). The approximately 50% growth inhibition induced by 1 mM DFMO after an 11-day incubation was completely reversed by as little as 0.3 µM spermidine, whereas 0.1 µM spermidine already restored growth of DFMO-treated cells to 78% of control value. However, addition of 50 µM DESC was unable to prevent the reversal of DFMO-induced growth inhibition by spermidine, even at a DESC:spermidine ratio of 500. Essentially similar results were obtained using horse serum instead of FBS, or replacing RPMI 1640 medium, which contains 3.2 µM reduced glutathione that might undergo thiol/disulfide exchange with DESC, with thiol-free IMEM (data not shown).

EXAMPLE 7

Stability of DESC in Biological Media

Figure 9A:
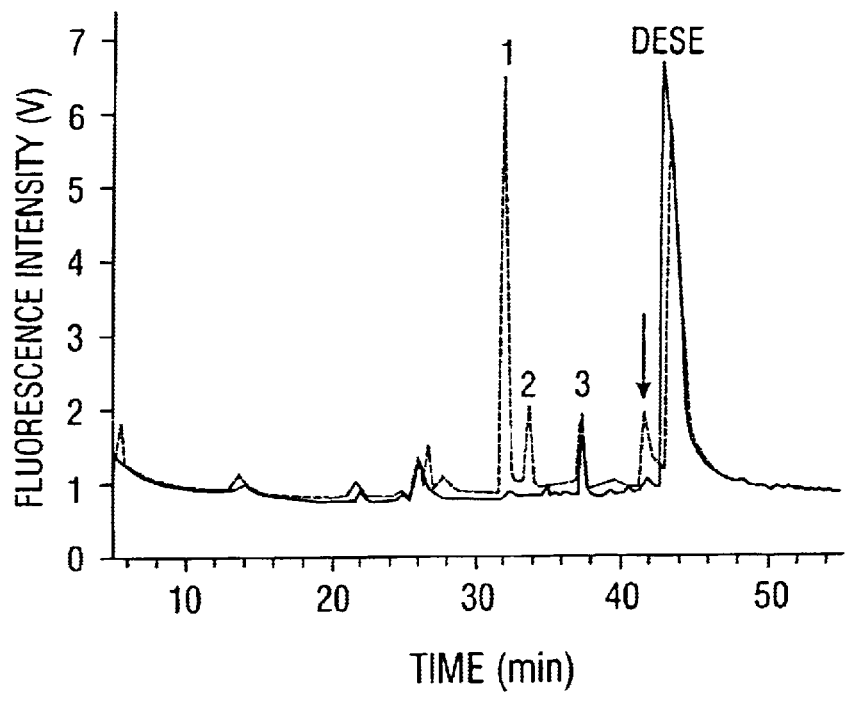
FIG. 9 represents the chromatographic profile of DESC and its degradation products in IMEM or PBS. DESC (50 μM) was added to 1 ml of IMEM containing 10% fetal bovine serum in the absence (A) or presence (B) of 1 mM aminoguanidine, or 1 ml PBS (C) in 24-well culture plates in the absence of cells. Media were analyzed after 20 minutes (solid lines) or 48 hours (dotted lines) of incubation at 37° C. in 95% air: 5% $CO_2$, water-saturated atmosphere for amine composition by ion-pair reversed-phase HPLC as described supra. Peaks 1 and 2 are degradation products of DESC, whereas peak 3 is a minor amount of DEASC initially present in the DESC preparation. Note the disappearance of peak 3 (DEASC) and the appearance of a shoulder (indicated by the arrow) at 42 minutes on the 48-hour profile in panel A.
Figure 9B:
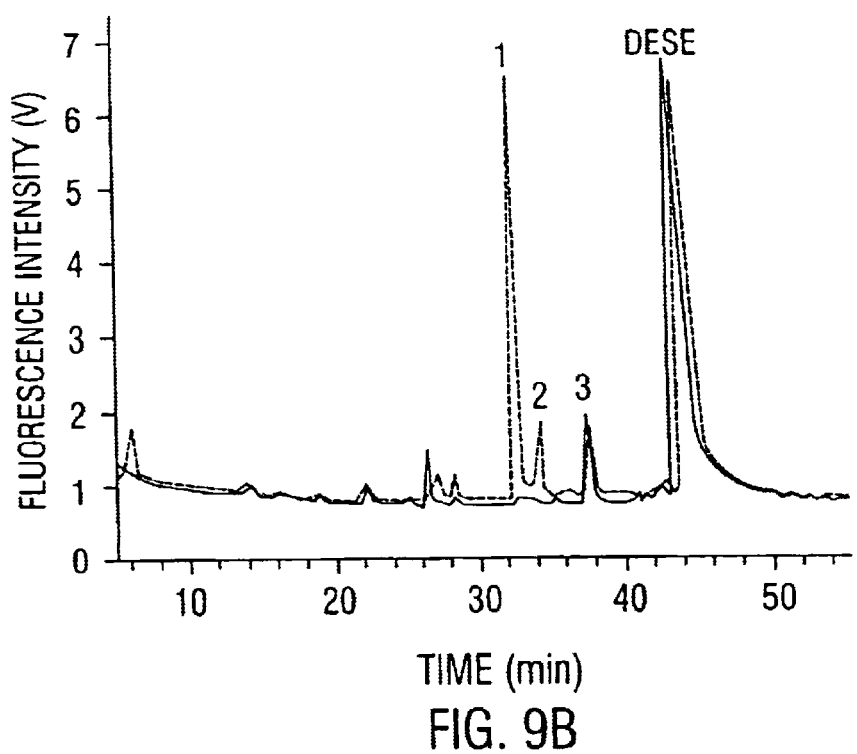
Figure 9C:
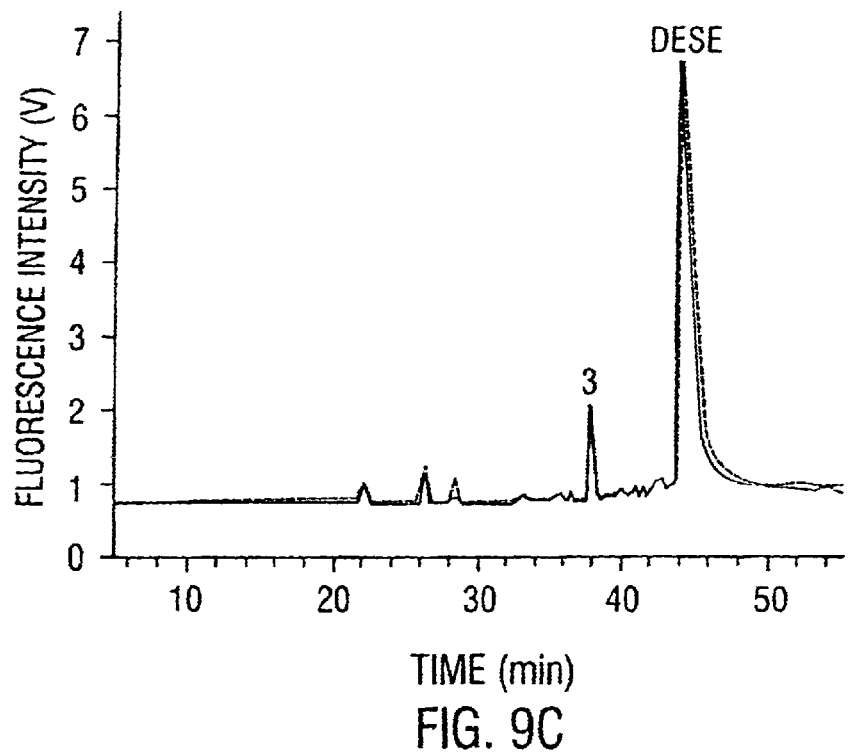
Figure 10:
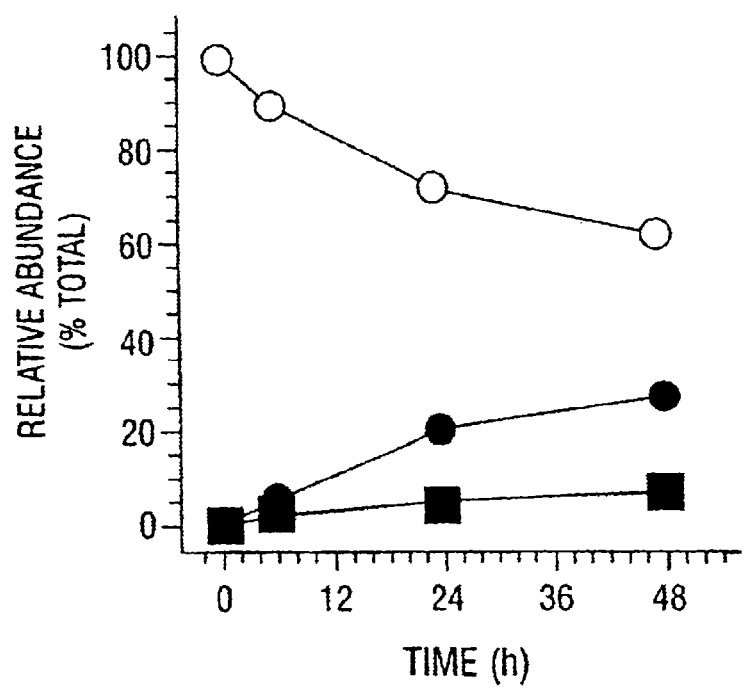
FIG. 10 represents the time course of degradation of DESC in growth medium. At time 0, 50 μM DESC was added to 1 ml of IMEM in 24-well culture plates and the content in DESC (○), compound 1 (Comp 1, ●) and compound 2 (Comp 2, □) determined by HPLC after the indicated incubation period at 37° C. in a 5% $CO_2$ atmosphere. Data represent the mean of triplicate determinations from a representative experiment.

The inability of DESC to block the biological effect of exogenous spermidine, even when present at large molar excesses, might have been caused by its degradation in growth media. To assess this hypothesis, DESC solutions (20 µM) made in PBS or in sterile IMEM medium enriched with 10% (v/v) FBS were incubated for 20 minutes or 48 hours under cell-free conditions at 37° C. in a humid 5% CO$_2$ atmosphere, and the polyamine analog was then analyzed by ion-pair reversed-phase HPLC. After 48 hours, degradation of DESC to two new amine-containing derivatives occurred in IMEM (FIG. 9A, B) but not in PBS (FIG. 9C), as evidenced by the appearance of a major (compound 1) and minor (compound 2) peaks of o-phthaldialdehyde-reactive material eluting earlier than DESC. Although aminoguanidine did not prevent DESC degradation to the two unknown products, it did prevent the degradation of a trace amount of DEASC (indicated as compound 3) initially present in the DESC preparations, thus confirming that DEASC can indeed be a substrate of serum copper amine oxidase (FIG. 7). MESC could not be detected, indicating that DESC does not undergo reduction to MESC under conditions used for cell culture. Furthermore, the decomposition of DESC in IMEM showed an identical pattern in the presence or absence of FBS, which thus ruled out a serum component as being responsible for the degradation. FIG. 10 shows that DESC was slowly degraded to compounds 1 and 2. After 48 hours, i.e. the interval at which freshly made DESC-containing media were added to cell cultures in growth experiments, 40% of the DESC originally present had been decomposed by IMEM. Identical results were obtained using RPMI 1640 medium instead of IMEM. Thus, the present inventors propose that a component present in IMEM and RPMI 1640 medium, but not in PBS, must be responsible for the degradation of DESC.

DESC, a novel type of spermine derivative, is shown to be endowed with high affinity for the polyamine transport system while being highly resistant to cellular uptake. The combination of these two attributes confers unique characteristics to DESC as a pure competitive antagonist of polyamine uptake.

As compared with spermine, the higher Ki of MESC against putrescine, spermidine and spermine uptake could owe to the presence of an amide linkage, which decreases the basicity of the neighboring secondary amino group of the spermine head (pKa=5.5 in comparison with 8.9–9.8 for spermine) (Tabor, C. W. and Tabor, H. 1984. Ann. Rev. Biochem. 53: 749–790; Remy, J.-S., Kichler, A., Mordvinov, V., Schuber, F. and Behr, J.-P. 1995. Proc. Natl. Acad. Sci. USA 92: 1744–1748, and/or may cause steric hindrance for its interaction with the polyamine binding site (Bergeron, R. J. and Seligsohn, H. W. 1986. Bioinorg. Chem. 14: 345–355; Porter, C. W., Cavanaugh, P. F., Jr., Stolowich, N., Ganis, B., Kelly, E., and Bergeron, R. J. 1985. Cancer Res. 45: 2050–2057). Despite the particular structural features of MESC as a ligand, its dimerization into DESC increased by up to 20-fold the affinity of the resulting structure for the polyamine transporter. There is no precedent for dimeric polyamine structures like DESC. Its overall design is reminiscent of that of 2-N-4-(1-azi-2,2,2,-tri-fluoroethyl) benzoyl-1,3-bis(D-mannos-4-yloxy)-2-propylamine, an impermeant ligand which binds to the exofacial domain of facilitative glucose transporters and bears two symmetrical sugar moieties linked tail to tail (Clark, A. E. and Holman, G. D. 1990. Biochem. J. 269: 615–622). At least one mammalian glucose transporter, namely GLUT-1, exists as a tetrameric complex in its native form (Hebert, D. N. and Carruthers, A. 1992. J. Biol. Chem. 267: 23829–23838; Gould, G. W. and Holman, G. D. 1993, Biochem. J. 295: 329–341). The stronger affinity of DESC relative to MESC could reflect a dyad symmetry in the organization of the transporter complex. Alternatively, dimerization of MESC into DESC could impose conformational constraints (e.g. due to electrostatic repulsion) that would favor recognition of the polyamine binding site of the carrier by each of the symmetrical spermine moieties.

MESC thioethers as diverse in size as MESC-LY, MESC-ASIB, or MESC-acetamide had $K_i$ values virtually identical to that of MESC, indicating that the thiol group of MESC does not specifically determine its lower affinity as a polyamine transport inhibitor as compared with DESC. These data suggest that additional bulk on the side chain has little influence on the interaction of MESC with the polyamine transporter, in agreement with the observation that large substituents attached to the distal end of a spacer of sufficient length do not notably decrease the affinity of spermidine as a substrate for uptake (Holley, J. O., Mather, A., Wheelhouse, R. T., Cullis, P. M., Hartley, J. A., Bingham, J. P., and Cohen, G. M. 1992. Cancer Res., 52: 4190–4195). Unexpectedly, the MESC-cysteamine mixed disulfide (DEASC) was found to block putrescine uptake as a mixed competitor/non-competitor, whereas MESC and DESC behaved like pure competitive inhibitors of putrescine transport. Since the interaction of DESC or MESC with the polyamine transporter was strictly competitive, and because DEASC exhibits higher affinity than MESC as an inhibitor of diamine and polyamine transport, the spermine head and the cysteamine side chain of DEASC might be respectively responsible for the competitive and non-competitive components of its transport inhibition.

The biochemical properties of DESC clearly illustrate that the binding affinity of a compound can be dissociated from its ability to serve as a substrate for the polyamine transporter. The large size of DESC cannot be the main factor preventing its internalization through the channel-like portion of the transporter since MESC was also virtually impermeant. Thus, the mere attachment of an amido side chain on the spermine backbone would appear to be responsible per se for the impaired internalization of MESC and its derivatives. Indeed, $N^4$-alkylated spermidine derivatives are far better competitors of spermidine uptake than their $N^4$-acyl counterparts in mouse leukemia cells, in support of the notion that charged secondary amino groups are important in the interaction with the polyamine carrier (Porter, C. W., Cavanaugh, P. F., Jr., Stolowich, N., Ganis, B., Kelly, E., and Bergeron, R. J. 1985. Cancer Res. 45: 2050–2057). However, the latter argument cannot account for the fact that long-chain aliphatic, α,ω-diamines with at least 6 to 7 methylene groups have an affinity comparable to that of spermidine (Lessard, M., Zhao, C., Singh, S. M. and Poulin, R., 1995. J. Biol. Chem. 270: 1685–1694, Bergeron, R. J. and Seligson, H. W. 1986. Bioinorg. Chem. 14: 345–355; Porter, C. W. and Bergeron, R. J. 1983. Science 219: 1083–1085; Minchin, R. F., Martin, R. L., Summers, L. A. and Hett, K. F., 1989. Biochem. J. 262: 391–395; Gordonsmith, R. H., Brooke-Taylor, S., Smith, L. L. and Cohen, G. M. 1983. Biochem. Pharmacol. 32: 3701–3709). A more likely explanation for the poor affinity of polyamines bearing an acyl side chain might be the steric hindrance due to the amide group, which restricts the freedom of rotation around the adjacent carbon and nitrogen atoms. There are indications that cyclic or pseudocyclic conformations of polyamines stabilized by hydrogen bonds might be energetically favored for recognition and/or internalization of substrates of the polyamine transport system (Lessard, M., Zhao, C., Singh, S. M. and Poulin, R., 1995. J. Biol. Chem. 270: 1685–1694; Bergeron, R. J. and Seligsohn, H. W. 1986. Bioinorg. Chem. 14: 345–355). The formation of such folded conformers would be impaired by the presence of an amide group next to the polyamine chain. In support of this hypothesis, chlorambucil-spermidine, which bears a N-propyl chlorambucil carboxamide side chain on the central nitrogen of spermidine, is a good substrate of the polyamine transport system, with a $K_m$ averaging that of spermidine (Holley, J. L., Mather, A., Wheelhouse, R. T. Cullis, P. M., Hartley, J. A., Bingham, J. P., and Cohen, G. M. 1992. Cancer Res. 52: 4190–4195). In marked contrast, a spermidine conjugate with a chlorambucil carboxamide side chain directly attached at the C5 position of the spermidine head is a very poor substrate of the polyamine uptake system (Stark, P. A., Thrall, B. D., Meadows, G. G., and Abdel-Monam, M. M. 1992. J. Med. Chem. 35: 4264–4269).

Although a 40-fold molar excess of DESC dramatically reduced the rate of spermidine uptake in ZR-75-1 cells, slow but continuous spermidine accumulation was still observed in the presence of the inhibitor. The low rate of polyamine internalization observed, even in the presence of a large excess of DESC, in addition to the slow decomposition of the inhibitor, may largely explain the complete inability of DESC to prevent polyamine-mediated prevention of growth inhibition by DFMO.

Since the affinity of MESC thioethers remains virtually unaffected relative to the unconjugated polyamine, MESC-ASIB might serve as a photoaffinity label to detect polyamine-binding proteins, including the polyamine carrier. Experiments are currently conducted with $^{125}$I-labeled MESC-ASIB to assess its usefulness as a probe to identify the mammalian polyamine transporter. A recent report has described the specific labeling of discrete plasma membrane proteins using $^{125}$I-labeled $N^1$-azidosalicylamido-norspermine and $N^4$-azido-salicylamidoethylspermidine as photoaffinity reagents (Felschow, D. M., MacDiarmid, J., Bardos, T., Wu, R., Woster, P. M. and Porter, C. W. 1995. J. Biol. Chem. 270: 28705–28711). However, these conjugates are internalized by mammalian cells (Felschow, D. M., MacDiarmid, J., Bardos, T., Wu, R., Woster, P. M. and Porter, C. W. 1995. J. Biol. Chem. 270: 28705–28711), and MESC-ASIB or similar derivatives could be useful as a photoactivatable probes to exclude labeling of intracellular proteins.

While not intended to be limited to any particular theory, the slow degradation of DESC observed in growth media, but not in PBS, was likely due to L-cystine, which is present at 100 and 200 μM in IMEM or RPMI 1640 medium, respectively, through the formation of mixed disulfides with DESC. Nevertheless, the cytotoxicity of high concentrations of DESC and MESC is unlikely to be solely due to the formation of such adducts, since MESC was less toxic than DESC, despite the fact that the free thiol group of the former would make it more reactive toward L-cystine]. The present data clearly show that DESC has remarkably low toxicity in comparison with its homolog spermine. Thus, the basic features of this molecule, including its resistance to BSAO, should be useful for the design of potent transport inhibitors with minor non-specific effects on cell viability. The inherent structural features of DESC that confer its high affinity and resistance to uptake should thus provide a useful framework for the design of potent irreversible inhibitors of polyamine transport, which could incorporate an alkylating group such as that used in the design of specific suicide substrates of mammalian glucose transporters (Clark, A. E, and Holman, G. D. 1990. *Biochem. J.* 269: 615–622; Lehmann, J., and Scheuring, M. 1995. *Carbohydrate Res.* 276: 57–74)].

Polyamine derivatives (natural or synthetic) comprising sulfur in the side chain have been made, because they conducted to the formation of dimers simply by forming a disulfide bridge. By-products which are not dimers have also shown an activity. However, it will be readily apparent to those skilled in the art that compounds being more stable than those containing sulfur atoms are contemplated. Therefore, the side chains used for increasing the affinity of the derivatives for a polyamine transporter and/or as substrates for labeling molecules and/or as a spacer in the making of a dimer can be varied to optimize the characteristics of the derivatives of the present invention.

Any equivalent structures of modifications obtainable without departing from the teachings and the spirit of this invention are considered as part of the scope thereof because the invention is in no way limited to the particularly disclosed embodiments, as reflected in the appended claims.

EXAMPLE 8

Synthesis and Evaluation of Spermine Dimers as Inhibitors or Polyamine Transport and Enhancers of Eflornithine Action in Tumor Cells and Tumor-Bearing Animals Novel spermine analogs will be synthesized and evaluated as blockers of transport in tumor cells simultaneously treated with D,L-α-difluoromethylornithine (FMO=Eflornithine). These molecules are based on the overall design of a prototype, 2,2'-dithiobis(N-ethyl-spermine-5-carboxamide) (DESC). DESC has recently been reported to act as a competitive and potent antagonist of polyamine uptake in leukemia and breast cancer cells. DESC is proposed here to potentiate the chemotherapeutic efficacy of DFMO. While not intending to be limited to any particular theory, it is proposed that such effect is provided by preventing the replenishment of DFMO-treated tumor cells with polyamines from exogenous sources. Structural modifications to the molecule will improve it to a pharmacologically useful compound. These modification include: [i] the replacement of the disulfide bridge with a fully reduced aliphatic chain to prevent its rapid reaction with biological thiols and disulfides and [ii] the addition of substituents to prevent its oxidative deamination by the ubiquitous plasma enzyme, serum amine oxidase.

Two types of DESC analogs will be synthesized, and characterized for their ability to inhibit polyamine transport and to enhance the therapeutic action of DFMO in various tumor cell types, including animal models. The first type of analogs will be simply obtained by substituting the original cystamine side chain of DESC with α,ω-diamine cross-linkers of varying length. The synthesis of these analogs will help in the short term to optimize the length of the cross-linker chain, and to rapidly evaluate their relative ability to potentiate DFMO action in vitro. The second type of analogs will be made according to a new route of synthesis to introduce methyl groups at the extremities of the spermine-like backbone, and will also incorporate alkylation instead of acylation of the aliphatic, α,ω-diamine cross-linker in order to improve their affinity for the polyamine transport system, their potency as antagonists of uptake and as enhancers of DFMO therapeutic action. The pharmacological evaluation of the second-type analogs will be conducted in a standard mouse model bearing L1210 leukemia tumor cell treated with DFMO.

2,2'-dithiobis (N-ethyl-spermine-5-carboxamide) (DESC) and its thiol monomer, N-(2-mercaptoethyl) spermine 5-carboxamide (MESC) (FIG. 11) have been synthesized as precursors of photoaffinity labeling probes of polyamine-binding proteins (21). Characterization of the potency of DESC and MESC to inhibit polyamine transport unexpectedly showed that DESC has ≠20-fold higher affinity than MESC for the polyamine carrier. The marked difference in transport inhibitory potency between MESC and its dimer suggested that the carrier protein might have a dyadic symmetry, and that the conjugation of two spermine molecules through a cross-linking side chain could markedly enhance the interaction with the polyamine transporter. Moreover, neither DESC nor MESC is significantly internalized by human breast cancer cells or mouse leukemia cells at concentrations that saturate the polyamine carrier, indicating that they are essentially membrane-impermeant (21). The combination of high affinity and lack of carrier-mediated permeation of DESC provided the basis for a novel design of pure polyamine transport antagonists that could be used in combination with DFMO to enhance polyamine depletion in tumor cells exposed to physiological levels of exogenous polyamines.

DESC was designed for biochemical use. It was found to degraded in physiological media due to thiol-disulfide reaction with compounds such as L-cystine. DESC cannot efficiently counteract the ability of exogenous spermidine to reverse DFMO-induced cytostasis in breast cancer cells as a result of this instability (21). DESC is also subject to attack by serum amine oxidase (SAO), an ubiquitous plasma enzyme which oxidatively deaminates aminopropyl groups, albeit to a much lesser degree than the parent compound spermine. Modifications that further improve the design of DESC analogs that are part of particular embodiments of the present invention are:

(1) To use chemically inert, aliphatic diamines as cross-linkers to conjugate two spermine-like moieties; and/or (2) To introduce methyl groups on the terminal carbons of the spermine-like backbones of the molecule. This latter modification will prevent/reduce the oxidation of spermine by SAO.

8.2) Synthesis and biochemical evaluation of unmethylated, stable DESC analogs DESC analogs are prepared with unmodified-spermine backbones but different side chain lengths as lead compounds to guide us in the design of methylated analogs described herein. This series of compounds will be synthesized in order to:

(i) Perform a structure-function study in the short-term to determine the optimal length of the cross-linker for inhibition of polyamine uptake.

Compounds VIIIa to VIIID (FIG. 12) will be rapidly available in amounts sufficient for in vitro testing. A refinement to the originally propose route of synthesis will be the use of FMOC-blocked diamine precursors. One such diamine precursor is $NH_2(CH_2)_nNH_2$ where n=3 to 6. Instead of simultaneously coupling two spermine-like moieties to a diamine cross-linker, each amino group of the diamine cross-linker was sequentially amidated to the spermine-like precursor with the N-FMOC-diamine, and then the other amine group was deprotected for the second amidation reaction. This sequential reaction scheme improves the purification of the spermine dimer from the spermine monoamide. This was difficult to achieve with the original method. The present method will improve the yield of desired product through a better control of the reaction stoichiometry.

Figure 12:
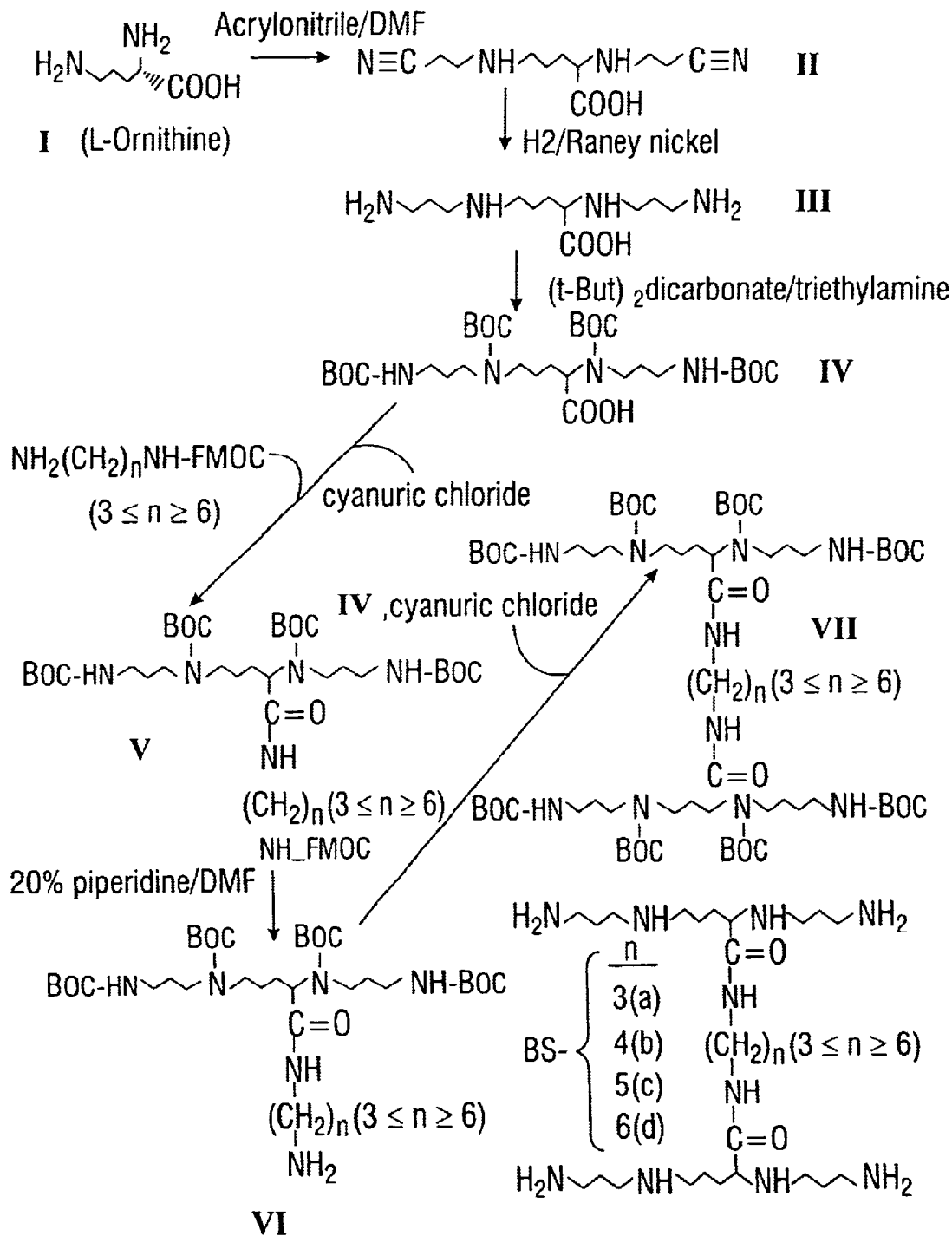
FIG. 12. Structure and scheme for the synthesis of unmethylated spermine analogs as polyamine transport inhibitors with a linker attached via amide bonds to the polyamine chains (BS-3, BS-4, BS-5 and BS-6 compounds). The method of synthesis is described in greater detail in Example 1.

The kinetic properties of these DESC analogs (abbreviated as BS-3, BS-4, BS-5 and BS-6; FIG. 12), as inhibitors of polyamine transport will be determined by uptake assays of radiolabeled putrescine, spermidine and spermine, according to procedures in Huber et al. (1996), J. Biol. Chem., 271:27556–27563, which is specifically incorporated herein by reference. These structures are shown below.

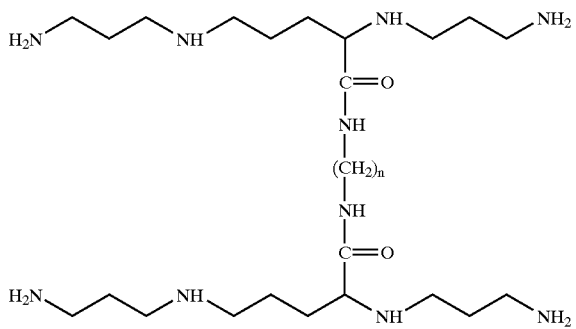

wherein n is 3, 4, 5 or 6.

(ii) Use of analogs to potentiate the effect of DFMO in the presence of exogenous polyamines, which is the main criterion of pharmacological activity for polyamine transport inhibitors.

These compounds are expected to be stable under cell culture conditions in the presence of aminoguanidine, a SAO inhibitor (13, 28, 40, 46, 49, 66, 67). These polyamine transport inhibitors will be evaluated using ZR-75-1 human breast cancer cells and L1210 mouse leukemia cells. Briefly, the rate of cell proliferation will be determined in ZR-75-1 and L1210 cells grown in the presence or absence of DFMO (1 and 5 mM, respectively), and of the transport inhibitor candidate to be analyzed, in the presence of increasing concentrations of putrescine or spermidine. The ability of the transport antagonist to prevent the reversal of DFMO-induced growth inhibition by exogenous putrescine or spermidine will provide a valid measurement of the pharmacological potential of these compounds as enhancers of DFMO action in vivo. These studies will also include (a) dose-response experiments to evaluate the cytotoxicity of these analogs and the optimal concentration for their use as inhibitors of polyamine uptake, and (b) measurement of the uptake of the transport inhibitors during incubation with tumor cells by HPLC, along with their effect on polyamine pools.

Since the latter type of inhibitors will rapidly provide the first stable DESC analogs available, the thorough analysis of their biological properties with cultured tumor cells will be important to validate the concept of spermine dimers as polyamine transport blockers. Moreover, the structure-function relationships of this series will help in refining the design of the methylated analogs described in the following section.

Figure 13:
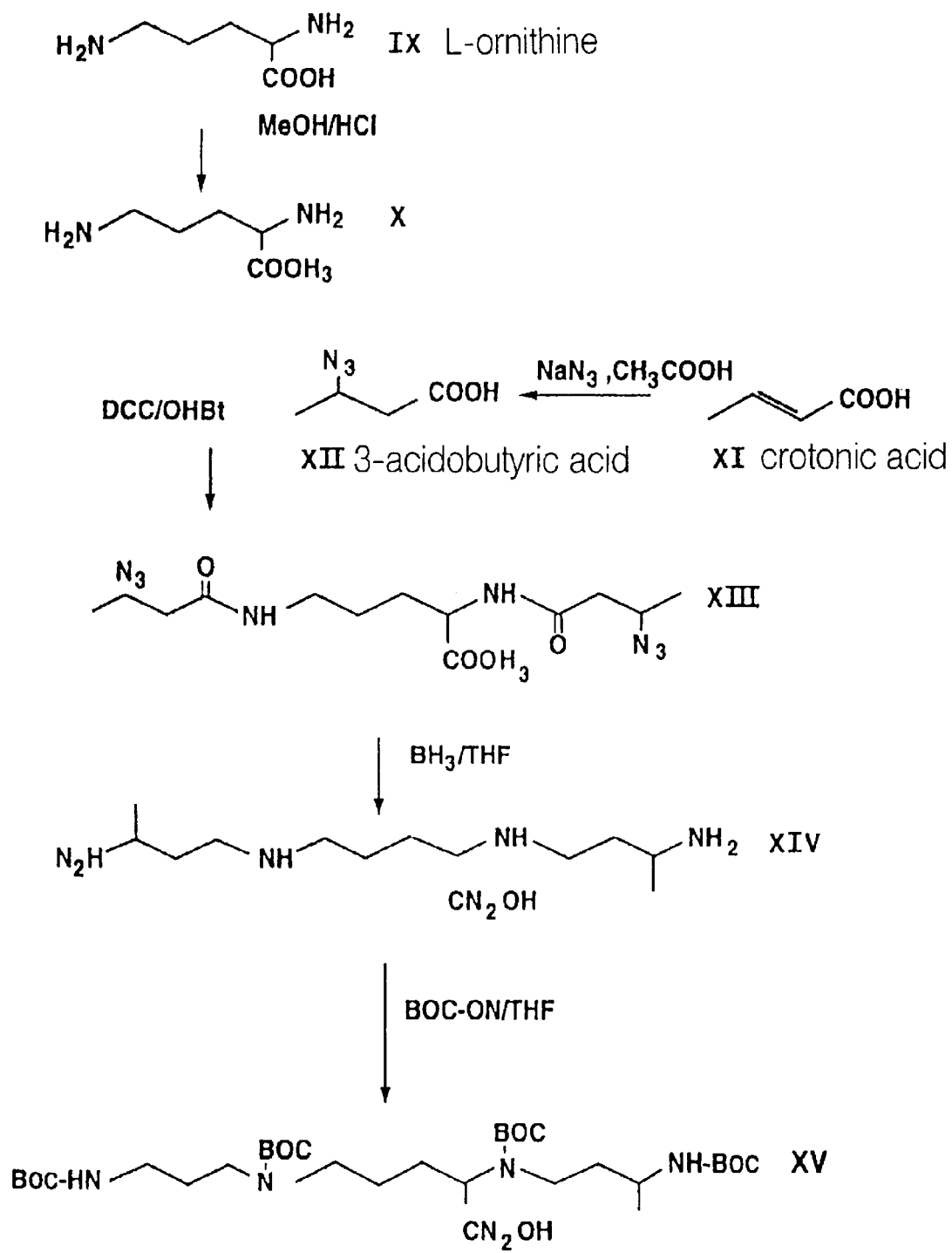
FIG. 13. Initial route of synthesis of terminal C-methylated, dimeric spermine analogs as transport inhibitors with a linker attached via an alkyl bond to the polyamine chains (BMS-3, BMS-4, BMS-5 and BMS-6). The steps presented in this figure describe the complete route of synthesis leading to the precursor $N^1$, $N^4$, $N^8$, $N^{12}$-tetra (Boc)-1, 12-dimethylspermine-5-carbinol (XV).
Figure 14:
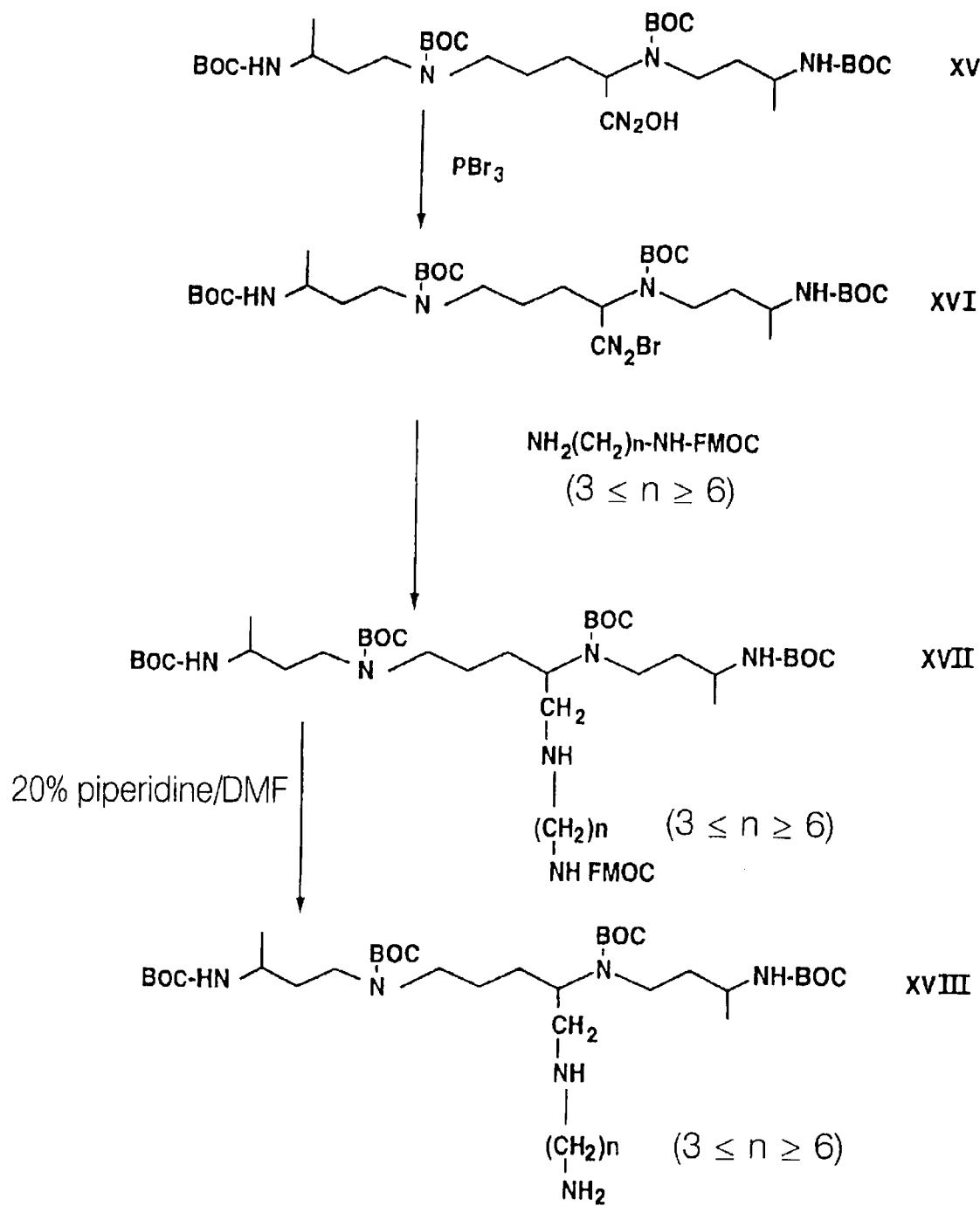
FIG. 14. The first step in the coupling of $N^1$, $N^4$, $N^8$, $N^{12}$-tetra (Boc)-1, 12-dimethylspermine-5-carbinol (XV) to the linker L (=a N-mono-FMOC-diaminoalkane), toward the synthesis of BMS compounds.
Figure 15:
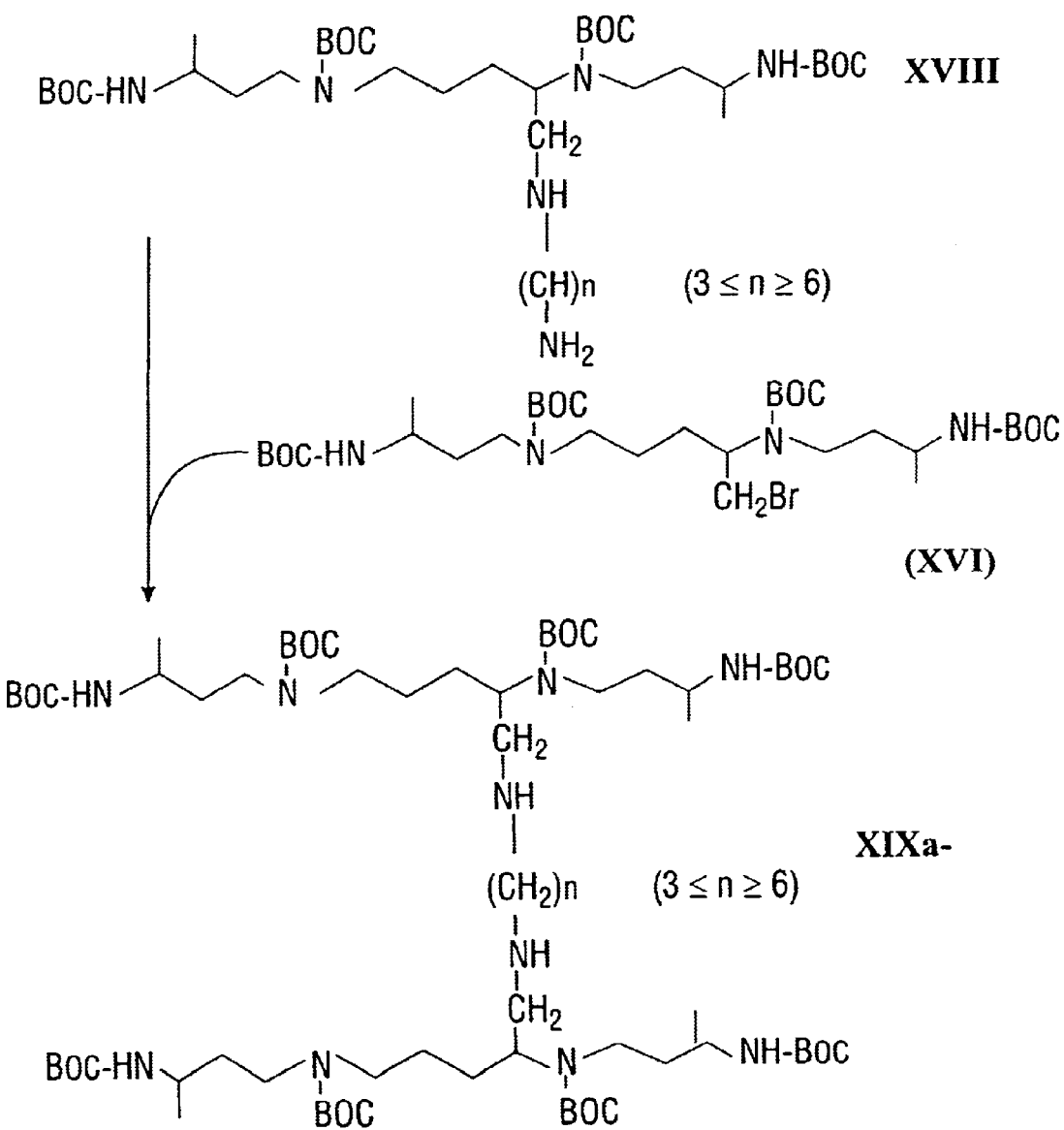
FIG. 15. The second step in the coupling of $N^1$, $N^4$, $N^8$, $N^{12}$-tetra (Boc)-1, 12-dimethylspermine-5-carbinol (XV) to the linker L (=aN-mono-FMOC-diaminoalkane) toward the synthesis of BMS compounds.
Figure 16:
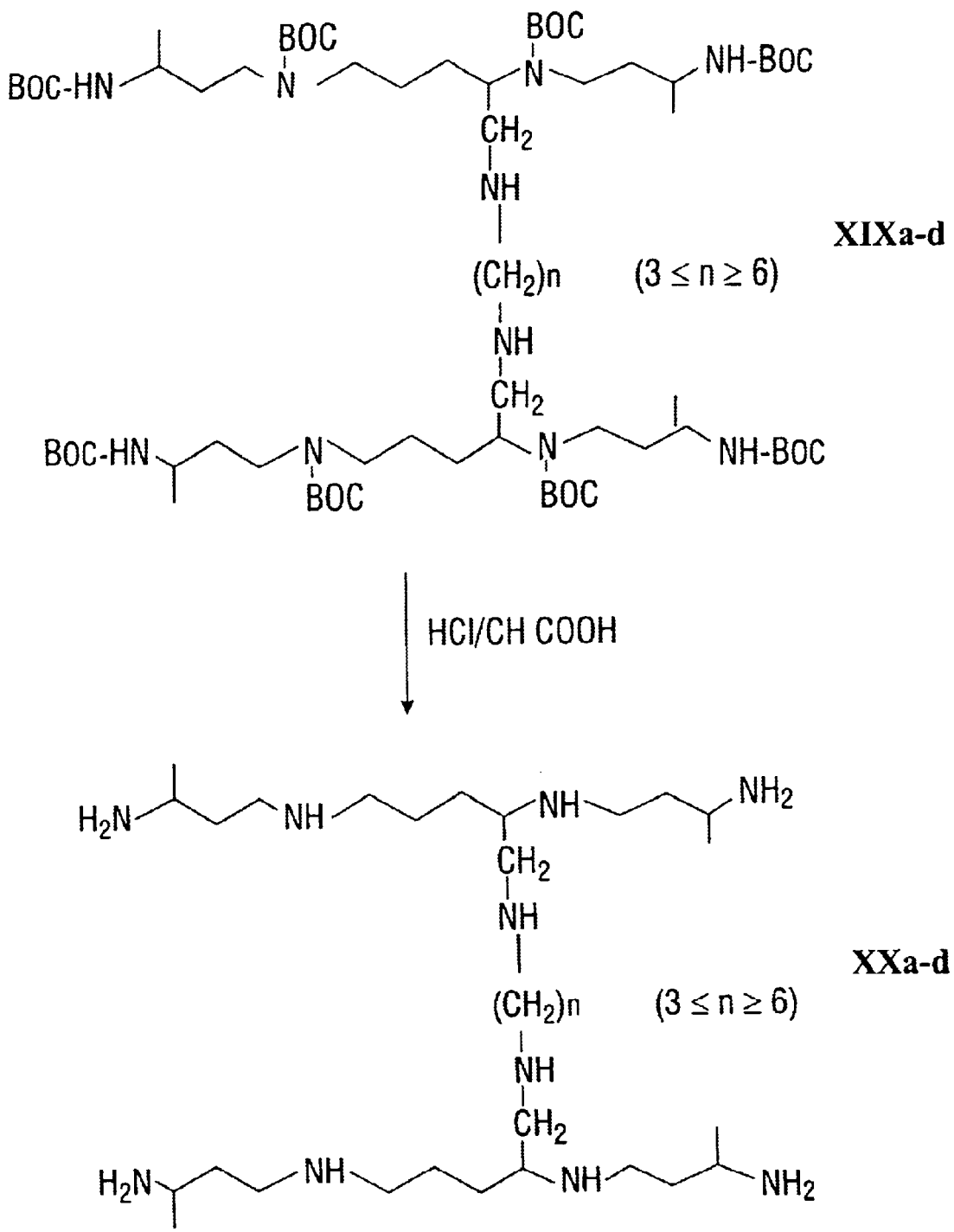
FIG. 16. The final step of the synthesis of BMS compounds (XX); the Boc-protected, cross-linked 1, 12-dimethylspermine dimer is deprotected to generate the BMS compounds. BMS-3, BMS-4, BMS-5 and BMS-6 correspond to $N^\alpha$, $N^\omega$-bis ([1, 12-dimethyl-spermine]-5-methyl)-diaminoalkanes where the diaminoalkane linker is 1,3-diaminopropane, 1,4-diaminobutane, 1,5-diaminopentane, and 1,6-diaminohexane, respectively.

8.3) Design, synthesis and evaluation of oxidation-resistant, stable methylated DESC analogs While replacing the nature of the cross-linking chain is a rather straightforward modification, the second alteration required considerable changes in the preparation scheme originally used for DESC synthesis. The reduction step proposed to obtain a 1,12-dimethylspermine 5-carboxyl methyl ester from a 1,4-bis(3-azidobutyramido) ornithine methyl ester (FIG. 13, XIII) could not spare the ester group, resulting instead into the formation of 1,12-dimethylspermine 5-carbinol (FIG. 3, XIV). Changing the nature of the ester group did not improve the synthesis since steric hindrance problems prevented amidation of the amino groups of ornithine methyl ester the most proximal to the ester group. The nature of the proposed precursor was modified, and two 1,12-dimethylspermine 5-methyl chains were conjugated to an α,ω-diamine cross-linker through alkylation rather than through amide bonds (FIGS. 14 to 16). This modification represents an improvement over the original design, since direct alkylation will lead to compounds with a higher affinity for the polyamine transporter—and higher potency as transport antagonists—as compared with the more rigid acylated analogs, as previously shown for spermidine analogs (8, 19, 44, 52, 54, 56). The proposed scheme of synthesis, for which steps IX to XIV have already been realized, is provided in FIGS. 13 to 16. This improved scheme also includes the use of mono-FMOC-protected diamines as building blocks for cross-linking the dimethylspermine-5-methyl precursors, as described above for the unmethylated DESC analogs. The resulting compounds are abbreviated as BMS-3, BMS-4, BMS-5 and BMS-6 (FIG. 16; compounds XXa to Xxd).

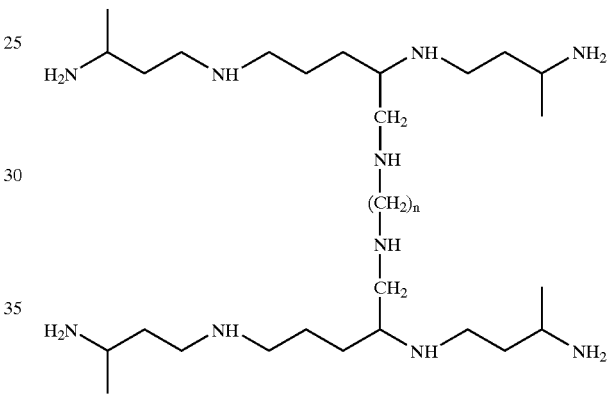

wherein n is 3, 4, 5 or 6.

The in vitro evaluation of this series will be conducted for the unmethylated DESC analogs. The effectiveness of a combination of polyamine depletion with the selected PA transport antagonist as an antitumor strategy will then be assessed in vivo. For this purpose, an established experimental cancer model, namely L1210 mouse leukemia, will be used to evaluate the therapeutic potential of the candidate transport inhibitor. This leukemia model is an aggressive tumor type with a median host survival time of 9 days in the absence of treatment. Moreover, it is completely resistant to DFMO as a single tumor agent in vivo (albeit very sensitive in vitro), whereas PA transport deficiency and/or reduction of exogenous PA sources confers a striking ability to DFMO to extend survival rates, with complete cure being observed in ≧75% of animals (1, 50).

Protocol 1—Toxicity will first be determined by single i.v. and i.p. injections of logarithmically increasing drug concentration to mice and estimating the $LD_{50}$. Blood samples will be taken at intervals to measure the plasma drug concentration by ion pairing reverse-phase HPLC (22, 23). Body weight and liquid consumption will also be monitored for 10 days, at the end of which period animals will be sacrificed to evaluate the incidence of liver and kidney damage. A similar experiment will be conducted by dissolving the drug in the drinking water with free access to the animals.

Protocol 2—On day 0, mice will be injected with L1210 cells, with concomitant treatment with DFMO or vehicle, plus or minus 2 different sublethal doses of the transport antagonist on a daily schedule. Oral. i.v. and i.p. routes will be compared for the transport antagonist. Survival will be evaluated for up to 120 days, with regular body weight measurements and blood sampling to determine the steady-state plasma concentrations of inhibitor. L1210 cells are strongly immunogenic tumors and cured animals develop extended immunity against this leukemia (1). Thus, to evaluate the curative potential of the drug combination, survivors will be rechallenged with L1210 cells in the absence of treatment and survival monitored.

EXAMPLE 9

The present example demonstrates the utility of the present invention with the use of compounds that are analogs of spermine that include two chains connected to one another through a linker. The linker molecule that attaches the two spermine chains may be any spacer chain that is capable of bridging the polyamine chains.

The two chains may attach to the linker at an internal C atom or an N group within the chain. It is also possible for one chain to be connected to the linker through one of its carbon molecules, while the second chain attaches to the linker molecule through an N group within its chain.

The general structure of compounds claimed in the following characteristics:

(1) The central carbon chain of the spermine backbone can have between 3 and 7 methylene groups or carbon atoms. This is the range of central chain length that can be accommodated with good affinity by the mammalian polyamine transporter (81).

(2) Each methylene group of the polyamine chains can be modified by methyl groups without compromising the ability of the inhibitor to interact with the polyamine transporter.

(3) The linkage between the polyamine chains and the spacer may comprise any type of linkage compatible with a $K_i \leq 20$ μM (relative to spermine) for the resulting inhibitor, such as direct alkyl substitution or ether group on the central methylene groups (Structure 1), or alkylation on the secondary amino (Structure 2) groups of the polyamine chain.

Structure 1

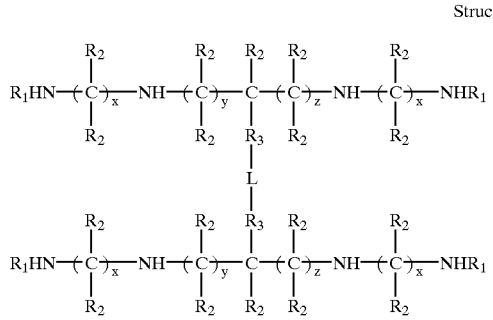

wherein $R_1$ is H, methyl, ethyl or propyl, $R_2$ is H or methyl, x is greater than two and less than five (2<x<5), and the sum of y+z is greater than or equal to 2 and less than or equal to 6 (2≦y+z≦6). $R_3=Ch_2$, S, C=O or NH; 2<x<5; 2≦y+ ≧≦6; L=a chemical structure (the linker) connecting covalently the two polyamine chians via alkyl, amide, ether or thioether bonds with a substituent group ($R_3$) attached on a carbon atom located between the two most internal amino groups of the polyamine chain.

Structure 2

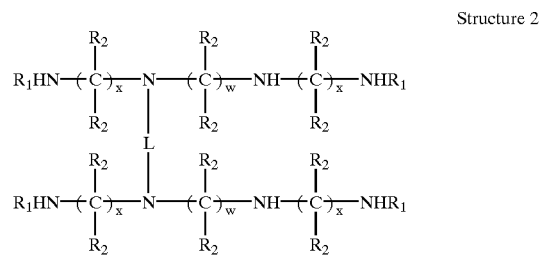

wherein $R_1$ is H, methyl, ethyl or propyl, $R_2$ is H or methyl, x is greater than two and less than five (2<x<5), w is greater than 2 and less than 8 (2<x<8) and the sum of y+z is greater than or equal to 2 and less than or equal to 6 (2≦y+z≦6).

The invention when a carbon of one chain is attached by a linker to the nitrogen of a second chain is represented in Structure 3.

Structure 3

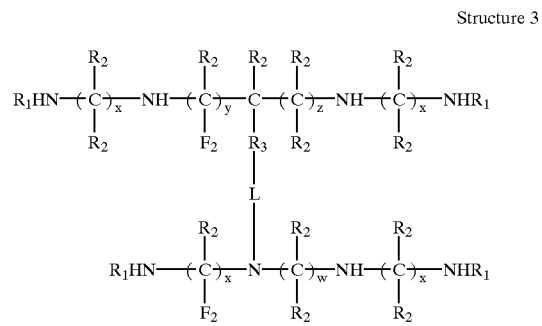

wherein $R_1$ is H, methyl, ethyl or propyl, $R_2$ is H or methyl, x is greater than two and less than five (2<x5), w is greater than 2 and less than 8 (2<x<8) and the sum of y+z is greater than or equal to 2 and less than or equal to 6 (2≦7+z≦6). $R_3=Ch_2$, S, C=O or NH; 2<x<5; 2≦y+≧≦6; L=a chemical structure (the linker) connecting covalently the two polyamine chains via alkyl, amide, ether or thioether bonds with a substituent group ($R_3$) attached on a carbon atom located between the two most internal amino groups of the polyamine chain.

Alkylation can be preferred over amidation because the former allows a greater flexibility to the polyamine chain to adopt the optimal conformation to interact with the polyamine transporter (81).

(4) The Linker (L) can be of any nature or chain length, as long as the total mass of the final structure does not exceed 3,000. These molecules may in other embodiments be described as having a total mass of between about 50 to about 2,500, or about between 500 to about 1500 or about 1,000 as a total mass. By way of example, such linkers may comprise alkyl, ether, a thioether, amide, phosphono, keto, amine, or sulfonyl groups or a combination thereof.

The linker may comprise a carbon chain by a length of 2 to 50 carbons.

In some embodiments, the carbon chain will have a length of between 5 to about 25 carbons, or between 10 and 20 carbons, or in even other embodiments, the carbon length of 2 to about 15 or 12 carbons.

EXAMPLE 10

Dimeric Spermidine Dimers as Polyamine Transport Inhibitors

In another family of synthetic derivitives of original polyamines, the synthetic original polyamine is either sym-norspermidine, sym-homospermidine, or spermidine, and is cross linked to a second original polyamine by a side group on the central amino group of said polyamines.

Various examples of such molecules, which by no means include all embodiments made possible by this alternative design, are (A) spermidine dimers cross-linked by an α,α'-dialkyl disulfide side chain via N-alkyl bonds with the central amino group of each triamine chain as depicted for type compound I. N,N'-bis)3-aminopropyl),N,N'-bis(4-aminobutyl)cystamine or BABAC (structure I, FIG. 25), (B) sym-norspermidine dimers [BNSpd-(n+2), structure II, FIG. 25] or spermidine dimers [BSpd-(n+2), structure III. FIG. 25] cross-linked by an aliphatic chain with n+2 methylene groups (0<n<8) via N-alkyl bonds with the central amino group of each triamine chain. (C) sym-norspermidine dimers cross-linked by an aryl-containing side chain via N-alkyl bonds with the central amino group of each triamine chain as depicted for type compound IV, N,N,N',N-tetrakis(3-aminopropyl)-p-xylylenediamine or TADAX (structure IV, FIG. 25), or their sym-homospermidine and spermidine-like homologs (not illustrated), (D) sym-homospermidine, sym-norspermidine or spermidine dimers cross-linked by an alkene side chain via N-alkyl bonds with the central amino group of each triamine chain with either a trans(BABA-trans, structure V, FIG. 26) or a cis configuration around the single double bond (BABA-cis, structure VI, FIG. 26) and (E) sym-homospermidine, sym-norspermidine or spermidine dimers cross-linked by an alkyne side chain via N-alkyl bonds with the central amino group of each triamine chain as depicted for structure VII (BABA-yne, FIG. 26).

The general structure of the noval compounds claimed (Structure 4) include the following characteristics:

(1) The two polyamine backbones are either spermidine [N-(3-aminopropyl)-1,4-diaminobutane], sym-homospermidine [N-(4-aminobutyl)-1,4-diaminobutane] or sym-norspermidine [N-(3-aminopropyl)-1,3-diaminopropane].

(2) Each methylene group of the polyamine chain can be modified by methyl groups without compromising the ability of the inhibitor to interact with the polyamine transporter.

(3) Each primary amino group of the polyamine chains can be modified by methyl, ethyl or propyl groups without compromising the ability of the inhibitor to interact with the polyamine transporter.

(4) The central secondary amino groups of the two polyamine chains are connected via N-alkyl bonds by a linker (L) so that the resulting inhibitor has a $K_i \leq 20$ $\mu$M (relative to spermine).

(5) The linker (L) can be of any nature or chain length, as long as the total final structure does not exceed 3,000. These molecules may in other embodiments be described as having a total mass of about 50 to about 2,500, or about between 500 to about 1,500, or about 1,000 as a total mass. By way of example, such linkers may comprise alkyl, aryl, ether, thioether, disulfide, amide, phosphono, keto, amine and sulfonyl groups or a combination thereof.

The general design and use of dimers of spermidine, sym-homospermidine and sym-norspermidine corresponding to general Structure 4 comprise yet another aspect of the present invention.

For example, in some embodiements, these synthetic derivatives comprise a structure of a first polyamine chain and a second polyamine chain according to the structure.

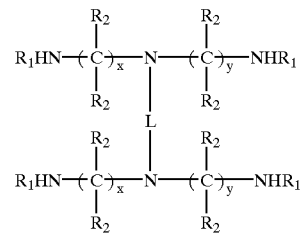

Structure 4 wherein $R_1$ is H, methyl, ethyl or propyl, $R_2$ is H or methyl, x is greater than two and less than five (2<x<5), y is greater than two and less than five (2<y<5), and L is a chemical structure (the linker) covalently connecting said second polyamine chain to said second chain through an alkyl bond, such as a α, ω, -diamine cross-linker.

In order to evaluate the effectiveness of dimeric triamines as polyamine transport inhibitors, we synthesized N,N'-bis (3-aminopropyl),N,N'-bis(4-aminobutyl)cystamine or BABAC (structure 1, FIG. 25; FIG. 31), and its thiol form N-(3-aminopropyl),N-(4-aminobutyl)cysteamine or AAC (FIG. 31) according to Scheme 4 described above (FIG. 30), using spermidine as a precursor polyamine. The ability of BABAC and AAC to inhibit the intracellular uptake of radio-labeled putrescine and spermidine in the ZR-75-1 human breast cancer cell line was then determined according to standard published procedures (Lessard, et al. and Poulin, et al.) Briefly, ZR-75-1 cells were grown for four days in twenty-four well plates in RPMI 1640 medium supplemented with 10% fetal bovine serum. 1 nM estradiol, 2 mM L-glutamine, 1 mM sodium pyruvate, 15 mM Hepes and antibiotics, and specific uptake of [$^3$H] putrescine, [$^3$H] spermidine and [$^{14}$C]spermine was measured as described (Lessard, et al.), using 20 $\mu$M and 3 $\mu$M substrate, respectively. ZR-75-1 cells are a convenient system to assess the potential of polyamine transport inhibitors because they exhibit elevated polyamine uptake activity (Lessard, et al.)

Figure 31A:
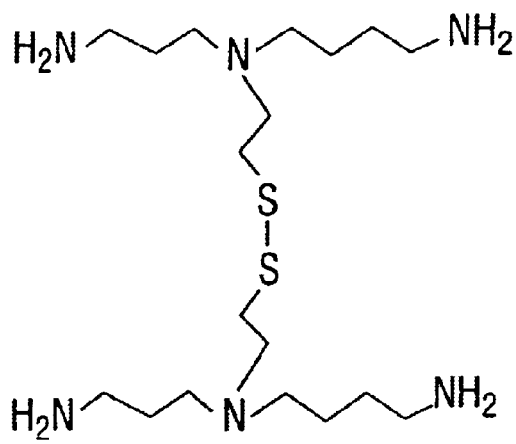
FIG. 31 illustrates a comparison between the structures of N,N'-bis(3-aminopropyl),N,N'-bis(4-aminobutyl)cystamine (BABAC), a dimeric spermidine derivative with a diethyldisulfide linker, of its monomeric thiol form N-(3-aminopropyl),N-(4-aminobutyl)cysteamine (AAC) and of 2,2'-dithiobis[N-ethyl-spermine 5-carboxamide (DESC).
Figure 31B:
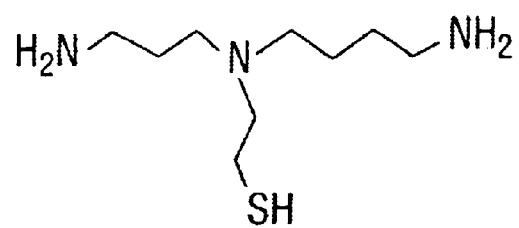
Figure 31C:
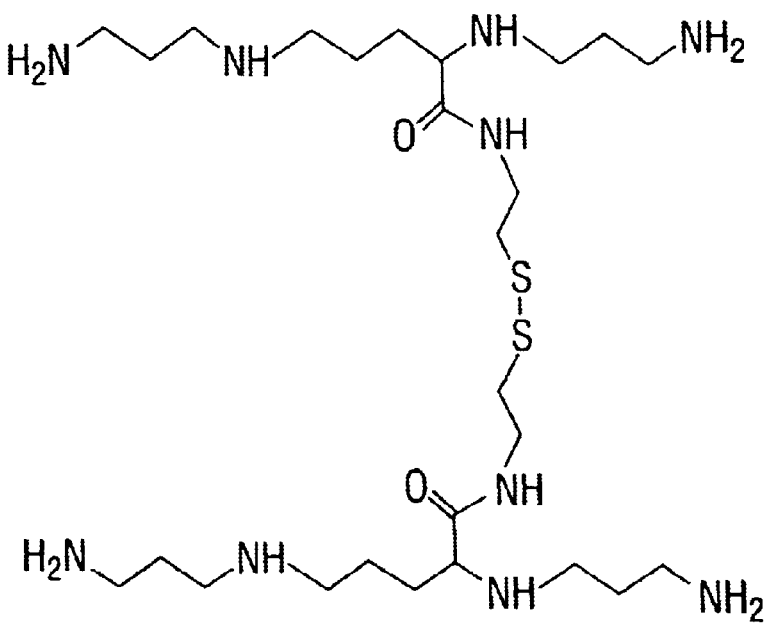
Figure 32A:
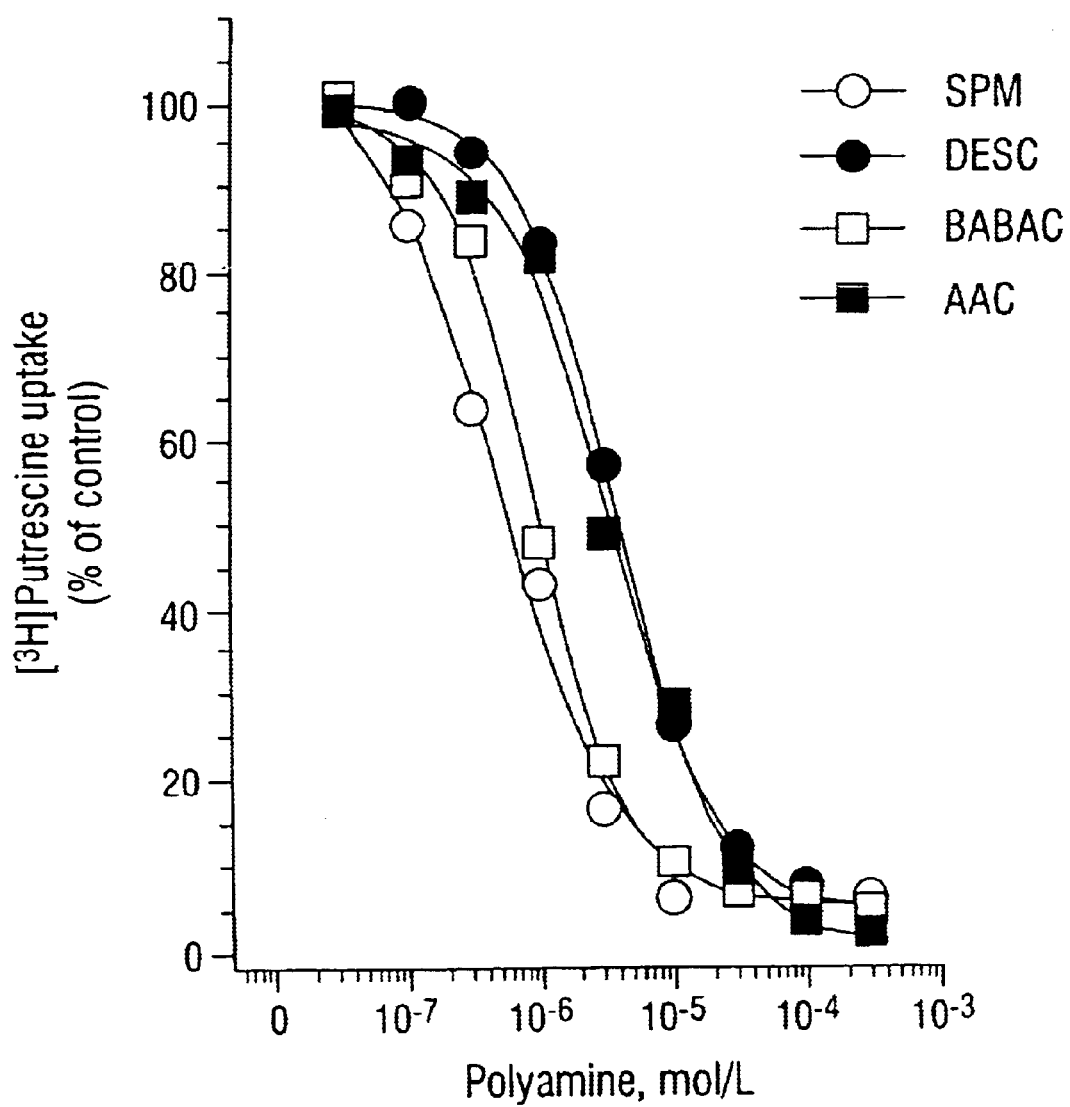
FIG. 32 [A-32C] represents the inhibition of [$^3$H] putrescine (32A), [$^3$H]spermidine (32B) and [$^{14}$C]spermine uptake (32C) by spermine (SPM), DESC, BABAC and AAC in human breast cancer cells ZR-75-1. Data represent the mean of triplicate determinations fro a representative experiment. Standard deviations, which did not exceed 10% of the mean value, were not shown for the sake of clarity.
Figure 32B:
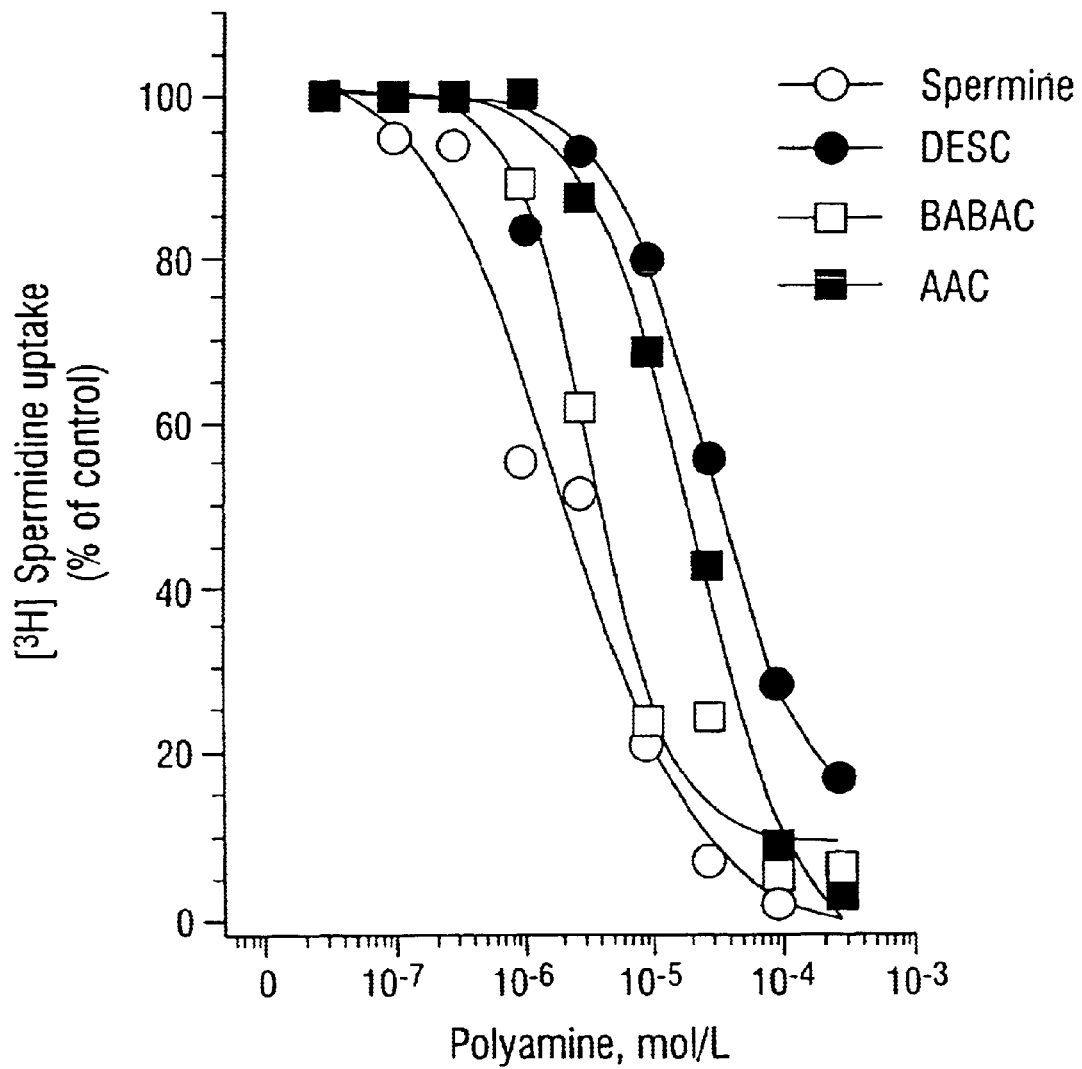
Figure 32C:
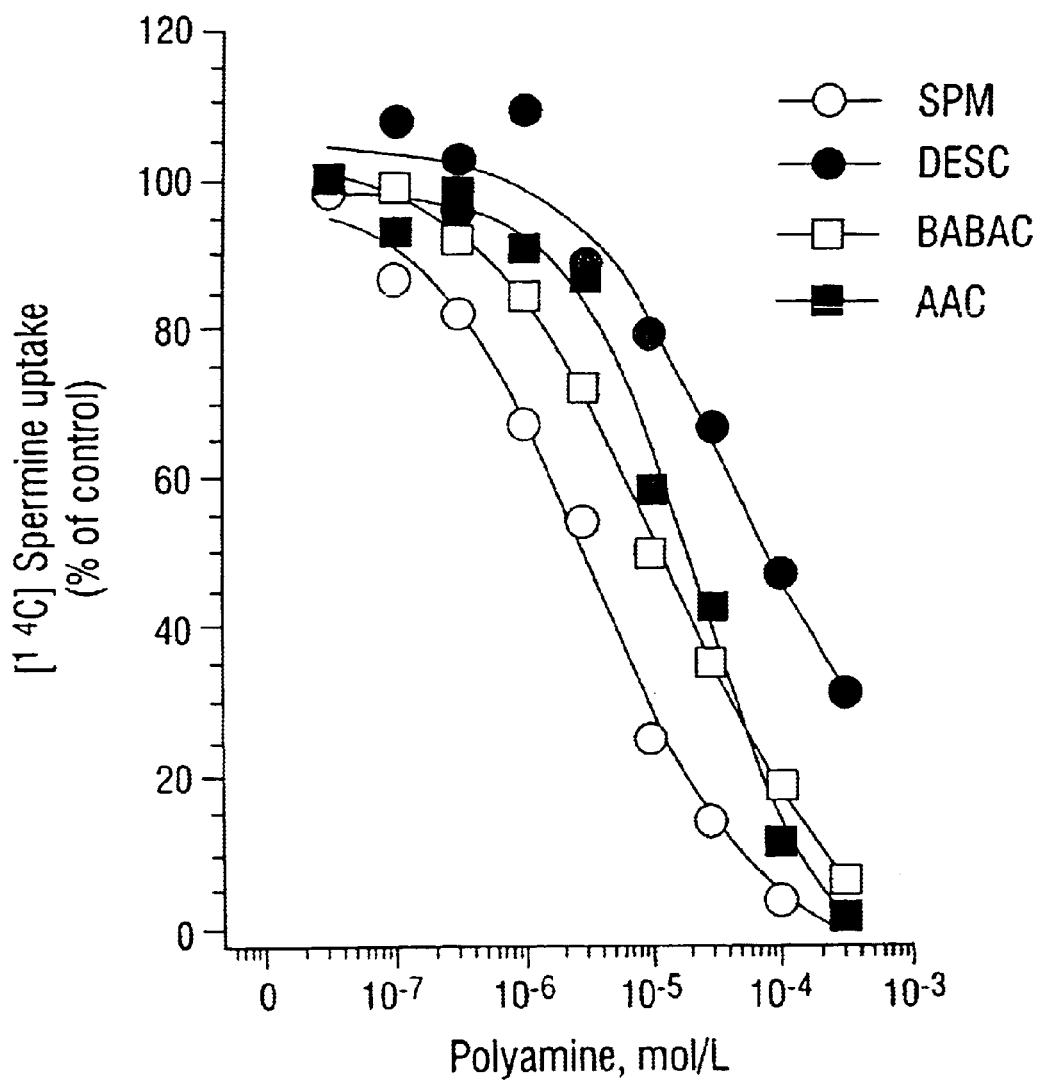
Figure 33:
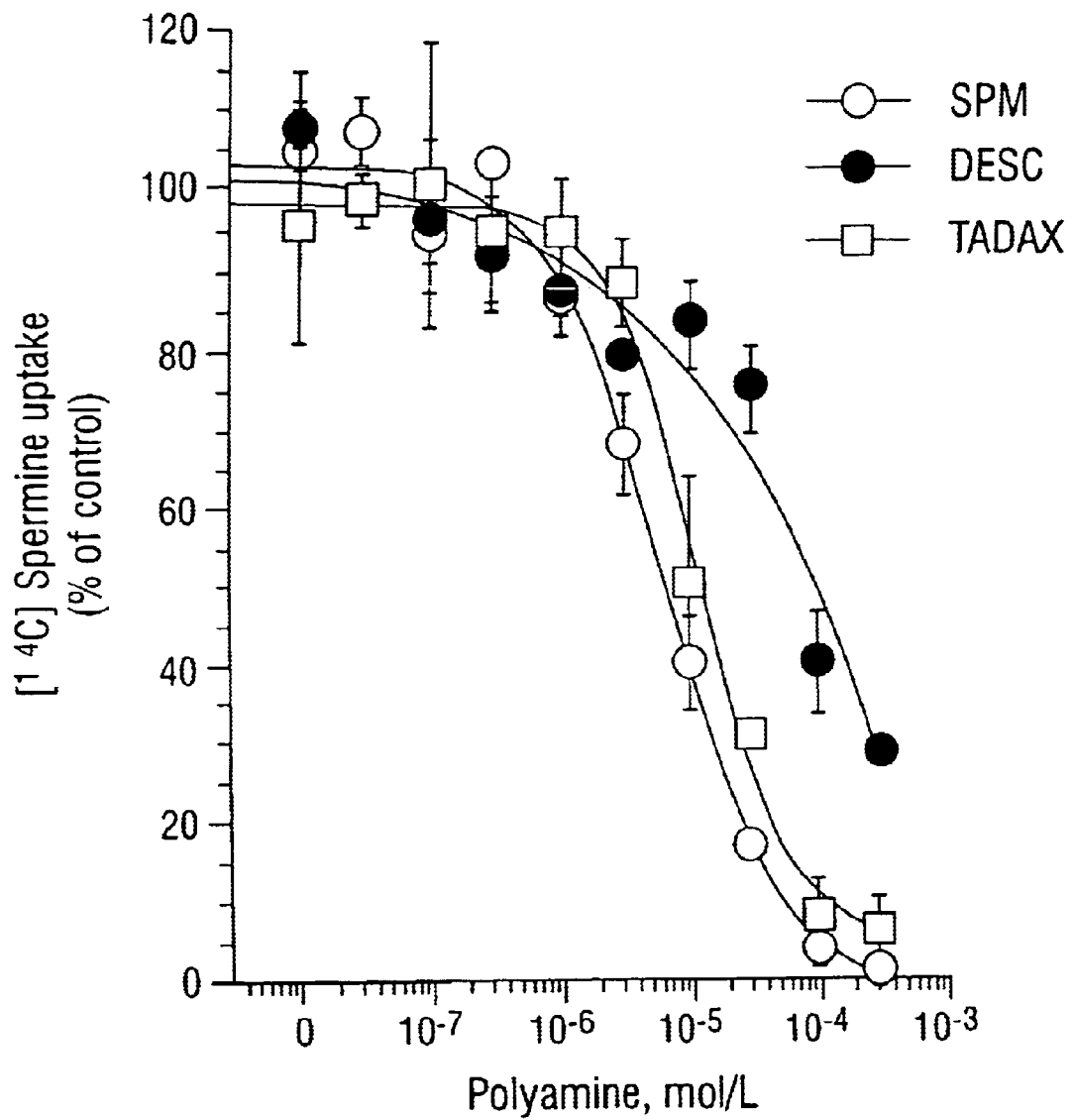
FIG. 33 represents the inhibition of [$^{14}$C]spermine uptake by spermine (SPM), DESC and TADAX in ZR-75-1 human breast cancer cells. Data are the mean±SD of triplicate determinations from a representative experiment.

As shown in FIG. 32, BABAC was a potent inhibitor of putrescine, spermidine and spermidine uptake in ZR-75-1 cells, with calculated apparent $K_i$ values of 0.15 $\mu$M, 0.68 and 2.1 $\mu$M, respectively. Its thiol monomer AAC was a less potent transporter inhibitor ($K_i$=0.54, 4.37 and 3.9 $\mu$M, respectively, as expected from the potentiating effect of dimerization on polyamine transport inhibition. Although the potency of BABAC to inhibit putrescine and spermidine uptake was only slightly lower than that of spermine ($K_i$ of 0.0745 and 0.40 $\mu$M, respectively, for spermine), it was clearly greater than that of the dimeric spermine-like inhibitor DESC (FIG. 31), which inhibited putrescine, spermidine and spermine uptake with apparent $K_i$ values of 0.54, 5.6 and 7.5 $\mu$M, respectively. These data clearly indicate that dimerization of a shorter polyamine chain (i.e. spermidine relative to spermine) can still generate potent polyamine transport inhibitors, and that the nature of the linker L as well as its site of covalent attachment on the polyamine backbone can strongly influence the potency of the dimer to inhibit polyamine uptake. A comparison between the structures of DESC and BABAC suggests that a N-alkyl type of attachment leads to superior properties of polyamine transport inhibition than an amide linkage on a methylene group of the polyamine backbone, and that this effect dominates over the effect of elongating the polyamine chains.

EXAMPLE 11

Polyamine Transport Inhibition by Sym-norspermidine Dimers

To further evaluate the validity of the design of dimeric triamines as polyamine transport inhibitors, we have assessed the ability of a sym-norspermidine dimer, namely N,N,N',N'-tetrakis(3-aminopropyl)-p-xylylenediamine (TADAX) (FIG. 25), to inhibit polyamine uptake in ZR-75-1 cells.

TADAX (FIG. 25) was synthesize according to the Scheme 2 described above (FIG. 26). Briefly, into a solution of norspermidine (2.55 g) and diethylamine (8.0 mL) in chloroform (100 mL) was added trityl chloride (10.87 g) portionwise. After addition, stirring was continued for 24 h. The reaction mixture was washed with water and dried over anhydrous potassium carbonate. The solution was concentrated under reduced pressure and the residue was re-crystallized from dichloromethane-methanol to obtain $N^1,N'$-bis(trityl)norspermidine. $^1$H NMR (300 MHz, CHCl$_3$) δ2.26 (m, 12H, aromatic H), 7.12–7.30 (m, 18H, aromatic H), 2.36 (t, 4H, J=8 Hz, 2×CH$_2$N), 2.18 (t, 4H, J=8 Hz, 2×CH$_2$N), 1.66 (m, 6H, 2× CH$_2$ and 2×NHTr).

A mixture containing N',N'-bis(trityl)norespermidine (770 mg), α,α=-dibromo-p-xylene (166 mg), anhydrous Na$_2$CO$_3$ (573 mg), acetonitrile (45 ml) and DMF (3 drops) was refluxed under nitrogen atmosphere for 3 days. Then, the mixture was filtered while it was still hot and the filtered solid was washed thoroughly with water and dried to give N,N,N',N'-tetrakis(N-trityl-3-aminopropyl) p-xylylene diamine. $^1$H NMR (300 MHz, CHCl$_3$) δ7.24 (m, 24H, aromatic H), 6.92–7.34 (m, 36H, aromatic H), 3.42 (s, 4H, 2×CH$_2$), 2.42 (m, 8H, 4×CH$_2$N), 2.08 (m, 8H, 4×CH$_2$N), 1.64 (m, 12H, 4×CH$_2$ and 4×NHTr).

N,N,N',N'-tetrakis(N-trityl-3-aminopropyl) p-xylene diamine (374 mg) was suspended in a solution of HCl 6 M (20 mL) and the mixture was refluxed for 24 hours. The solid was removed by filtration and the aqueous phase concentrated to 2–3 mL by rotary evaporation. Addition of ethanol into the concentrated solution afforded the hexahydrochloride salt of N,N,N',N'-tetrakis(3-aminopropyl) P-xylenediamine, or TADAX (FIG. 25).

The ability of TADAX to inhibit [$^{14}$C]spermine transport was next compared in ZR-75-1 human breast cancer cells using 3μM substrate (FIG. 32). In this assay, spermine has an apparent $K_m$=0.6 μM. It is clear that the p-xylylene norspermidine dimer TADAX ($K_i$=1.5 μM) is a much more potent spermine transport inhibitor than the prototypic spermine dimer DESC ($K_i$=17 μM), and was nearly as potent as the substrate spermine at interacting with the polyamine carrier in these cells. These data further demonstrate the importance of the crosslinker L in the relative ability of triamine dimers to inhibit polyamine transport.

Figure 34:
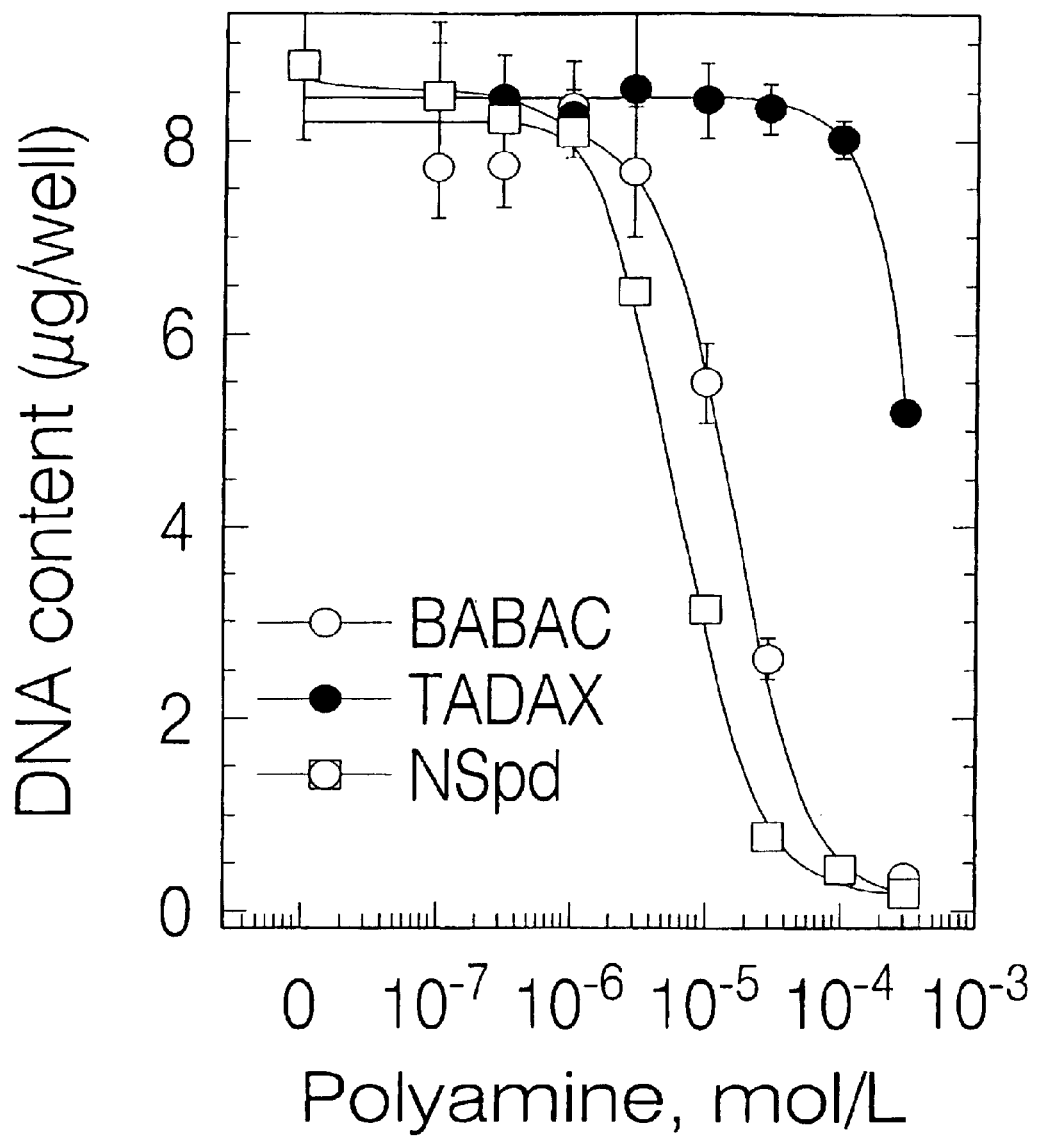
FIG. 34 represents the relative cytotoxicity of sym-norspermidine (NSpd), BABAC and TADAX in ZR-75-1 human breast cancer cells. Data are the mean±SD of triplicate determinations from a representative experiment.

To further substantiate the usefulness of triamine dimers such as TADAX as transport inhibitors, the cytotoxicity of TADAX and its ability to serve a transported substrate for the polyamine carrier were then evaluated. As shown in FIG. 34. TADAX was remarkably non-toxic to ZR-75-1 cells (IC$_{50}$>500 μM), as compared to sym-norspermidine or the disulfide BABAC, which had lethal effects on ZR-75-1 cells with IC$_{50}$ values of 6.4 and 17 μM, respectively. While the cytotoxicity of sym-norspermidine has been well documented (Bergeron and Seligshon, Komori and Ohsugi, Porter and Bergeron), a less pronounced, but yet significant cytotoxicity of DESC has been found using ZR-75-1 breast cancer-cells. That cytotoxicity may well be related to the reactivity of the disulfide groups of DESC and BABAC with biological thiols and disulfides found in growth media and at the cell surface. Thus, despite the presence of four 3-aminopropyl groups on the TADAX backbone, and its two sym-norspermidine-derived moieties, it is remarkably inert toward biological functions. This is consistent with the fact that no detectable accumulation of the compound was found in ZR-75-1 cells even after a 6-hour incubation, as determined by ion pairing-reverse phase high-pressure liquid chromatography of cell extracts performed as described (Lessard, et al.) (data not shown). These data suggests that the very low cytotoxicity of TADAX is related to its lack of uptake by ZR-75-1 cells. Moreover, these properties are those expected from an impermeant, pure antagonist of polyamine transport such as DESC, thus supporting the potential usefulness of TADAX and similar triamine dimers to preempt polyamine uptake by tumor cells.

Synthesis of Embodiments (1) Unmethylated spermine analogs (FIG. 17A): $N^1,N^4,N^8,N^{12}$-tetra-Boc-5-carboxyspermine (IV, FIG. 12) is first prepared as described (88). If the linker is going to be amidated to the polyamine chain, the carboxyl group used as an acceptor is activated with cyanuric chloride (88), and conjugated with a N-mono-FMOC diaminoalkane of the desired length to generate the corresponding $N^1,N^4,N^8,N^{12}$-tetra-Boc-spermine-5-N-(N-FMOC-aminoalkyl) carboxamide (V, FIG. 12). The FMOC group of the latter compound is removed with 20% piperdine/DMF, and the resulting $N^1,N^4,N^8,N^{12}$-tetra-Boc-spermine-5(N-ω-aminoalkyl) carboxamide (VI, FIG. 12) is then reacted with the acid chloride form of $N^1$, $N^4$, $N^8$, $N^{12}$-tetra-Boc-5-carboxyspermine (IV, FIG. 12). The latter compound is then deprotected with HCl/CH$_3$COOH to obtain the corresponding $N^α,N^ω$-bis (spermine-5-oyl)-diaminoalkane, the desired transport inhibitor (VII, FIG. 12). These compounds are symbolized as BS compounds, and BS-3, BS-4, BS-5 and BS-6 corresponds to the forms where the diaminoalkane linker is 1,3-diaminopropane, 1, 4-diaminobutane, 1,5-diaminopentane and 1, 6-diaminohexane, respectively. If the spacer is going to be alkylated to the polyamine chain, the carboxyl group used as an acceptor in an amidation reaction is first reduced to an alcohol with LiAH$_4$. After protecting the amine groups with carbobenzoxy (CBZ) groups, the alcohol is then converted to a bromide with PBr$_3$. The resulting CBX-protected spermine bromide is then reacted with a diamine spacer with a 2:1 stoichmetry to generate the CBZ-protected spermine dimer. This dimer is finally deprotected by catalytic hydrogenation with Pd/C (82) to generate the unmethylated spermine dimer (the transport inhibitor). If an ether linkage is desired, the alcohol obtained as above is then converted to an alkoxide with sodium metal, and then reacted with an alkyl dihalide (e.g. 1,3-diiodopropane) with a 2:1 stoichiometry to generate the CBZ-protected polyamine dimer, which is then deprotected as above to generate the unprotected polyamine dimer (the transport inhibitor). As an alternative precursor to ornithine, one may use instead 2-hydroxyputrescine, synthesized as described (83), and proceed with carboxyethylation and catalytic hydrogenation as in the route using ornithine as precursor, to obtain 6-hydroxyspermine. The four amino groups of the latter are protected with carbobenzoxy groups, and the alcohol is converted into an alkyl halide or alkoxide for subsequent reaction with the spacer as described above.

(2) Methylated spermine analogs (FIG. 17A): For example, ornithine methylester (X, FIG. 13) is synthesized as described (89) and is diamidated with two equivalents of 3-azidobutyric acid (XII, FIG. 13) using DCC/OHB, (90) to generate $N^1$, $N^4$-bis(3-azidobutyryl)-ornithine methylester (XIII, FIG. 13). The latter is than reduced using BH$_3$/THF (90) to obtain 1, 12-dimethylspermine-5 carbinol (XIV, FIG. 13). After protection of all four amino groups with Boc groups (XV, FIG. 13), the carbinol group is activated with PB$_3$ to generate 1,12-dimethyl-$N^1$, $N^4$, $N^8$, $N^{12}$-tetra(Boc)-5-bromomethyl spermine (XVI, FIG. 14), and reacted with FMOC-NH-(CH$_2$)$_n$NH$_2$ (where 3≦n≦6) to generate the corresponding 1, 12-dimethyl-$N^1,N^4,N^8,N^{12}$-tetra(Boc)-spermine-5 ($N^α$-methyl, $N^ω$FMOC-diaminoalkane) (XVII, FIG. 14). After removing the FMOC group with piperdine/ dimethylformamide (XVIII, FIG. 14), the free amino group of compound XVIII is alkylated with one equivalnet of compound XVI to generate a $N^α$, $N^ω$bis[1, 12-dimethyl-$N^1$, $N^4,N^8,N^{12}$-tetra(Boc)-spermine]-5-methyl)-diaminoalkane (XIX, FIG. 15). The latter compound is then deprotected with HCl/CH$_3$COOH to finally obtain the methylated spermine analog (BMS-3, BMS-4, BMS-5 and BMS-6), which are the desired transport inhibitors (XXa–d, FIG. 15).

(3) Unmethylated, N-alkylated spermine analogs (FIG. 17B): A symmetrical dimer that can be made where the linker (L) bridges two polyamine derivatives chains through one of the innermost, secondary nitrogens of each polyamine chain.

(a) N-benzyl-1,3-diaminopropane (XXI, FIG. 18) is first obtained by catalytic hydrogenation of 3-(benzylamino)propiononitrile with Raney nickel as described (84).

(b) N-benzyl-1,3-diaminopropane is then N-alkylated with 3-bromobutyronitrile to generate $N^1$-benzyl, $N^3$-(3-cyanopropyl)-1,3-diaminopropane (XXII, FIG. 18) (85).

Figure 18:
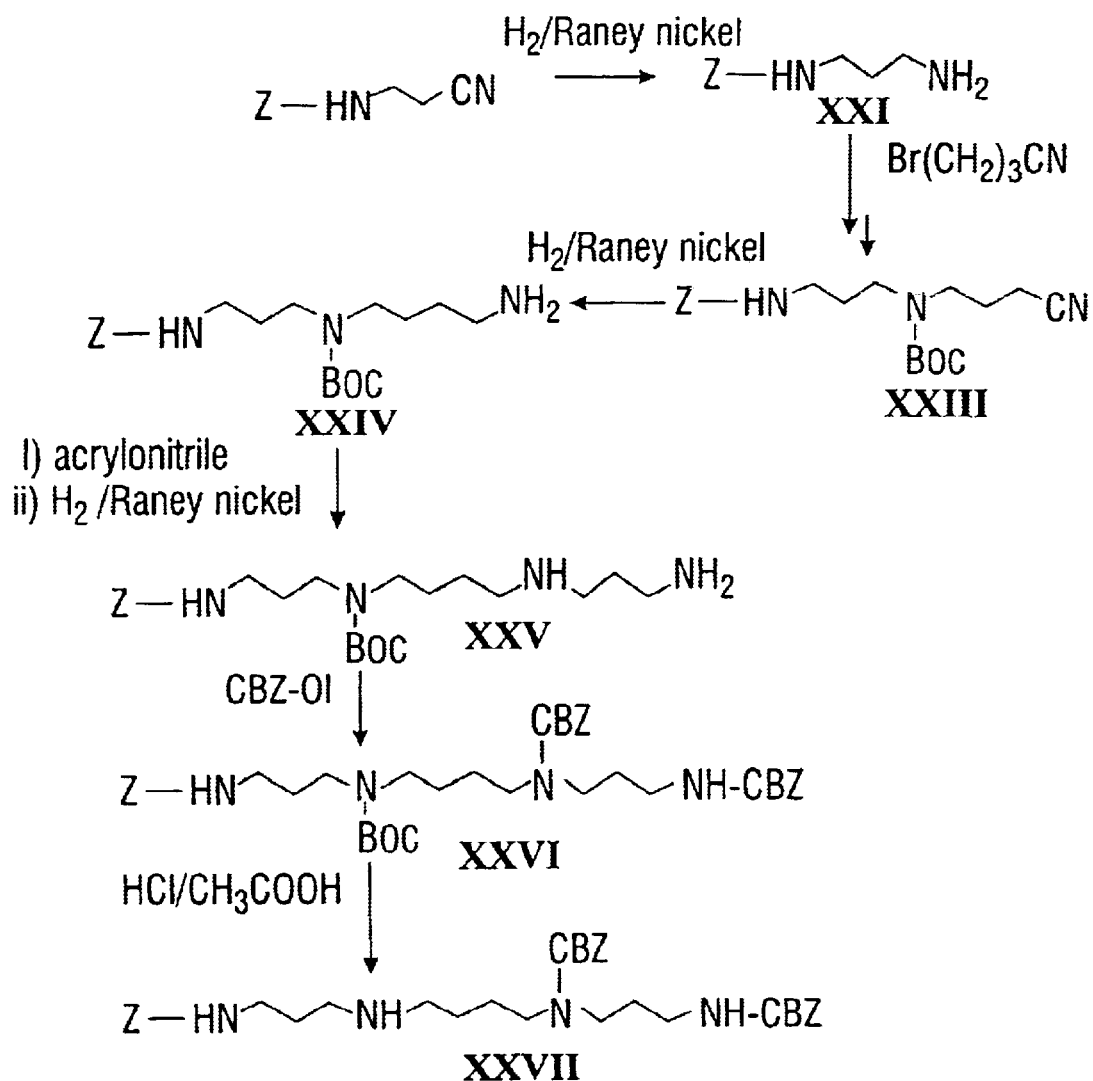
FIG. 18. Initial route of synthesis of unmethylated, $N^4$-alkylated dimeric spermine analogs (FIG. 17B). Steps leading to the synthesis of the intermediate $N^1$-benzyl, $N^8$, $N^{12}$-di(CBZ)-spermine.

(c) $N^1$-benzyl, $N^3$-(3-cyanopropyl)-1,3-diaminopropane is protected with a Boc group (86) to generate $N^1$-benzyl, $N^3$-Boc, $N^3$-(3-cyanopropyl)-1,3-diaminopropane (XXIII, FIG. 18)

(d) $N^1$-benzyl, $N^3$-Boc, $N^3$-(3-cyanopropyl)-1,3,-diaminopropane is reduced to $N^1$-benzyl, N-Boc-spermidine (XXIV, FIG. 18) by catlytic hydrogenation with Raney nickel (84).

(e) $N^1$-benzyl, $N^4$-Boc-spermidine is then cyanoethylated with acrylonitrile to generate $N^1$-benzyl, $N^4$-Boc, $N^8$-cyanoethyl-spermidine, and reduced to $N^1$-benzyl, $N^4$-Boc-spermine by catalytic hydrogenation with Raney nickel (84) (XXV, FIG. 18).

(f) The two free amino groups of $N^1$-benzyl, $N^4$-Boc-spermine are protected wtih CBZ groups are described (87) to generate $N^1$-benzyl, $N^4$-Boc, $N^8$, $N^{12}$-di(CBZ)-spermine (XXVI, FIG. 18).

(g) $N^1$-benzyl, $N^4$-Boc, $N^8$, $N^{12}$-di(CBZ)-spermine is then deprotected to $N^1$-benzyl, $N^8$, $N^{12}$-di(CBZ)-spermine with trifluoroacetic acid as described (87) (XXVII, FIG. 18).

Figure 19:
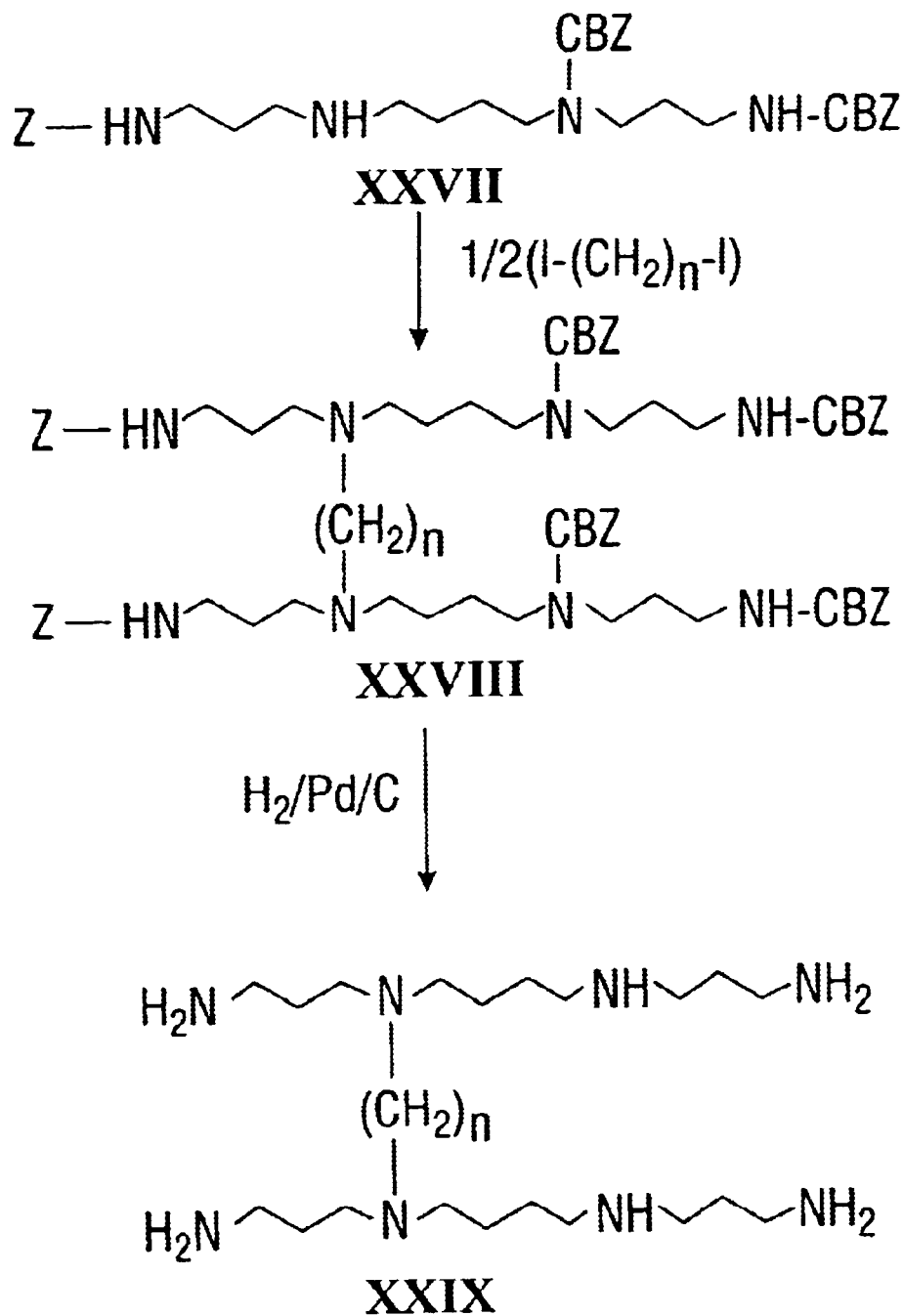
FIG. 19. Final steps for the synthesis of unmethylated, $N^4$-alkylated dimeric spermine analogs (FIG. 17B, represented by type compound XXIX). For the aliphatic linker —$(CH_2)_n$—, 2<n<51.

(h) $N^1$-benzyl, $N^8$, $N^{12}$-di(CBZ)-spermine can then be cross-linked with an α,ω-dibromoalkane of the desired chain length to generate the corresponding bis($N^1$-benzyl, $N^8$, $N^{12}$-di(CBZ)-spermine) dimer (XXVIII, FIG. 19), which is then deprotected by catalytic hydrogenation with Pd/C (87) to generate the unmethylated, N-alkylated spermine dimer (the transport inhibitor) (XXIX, FIG. 19).

Figure 20:
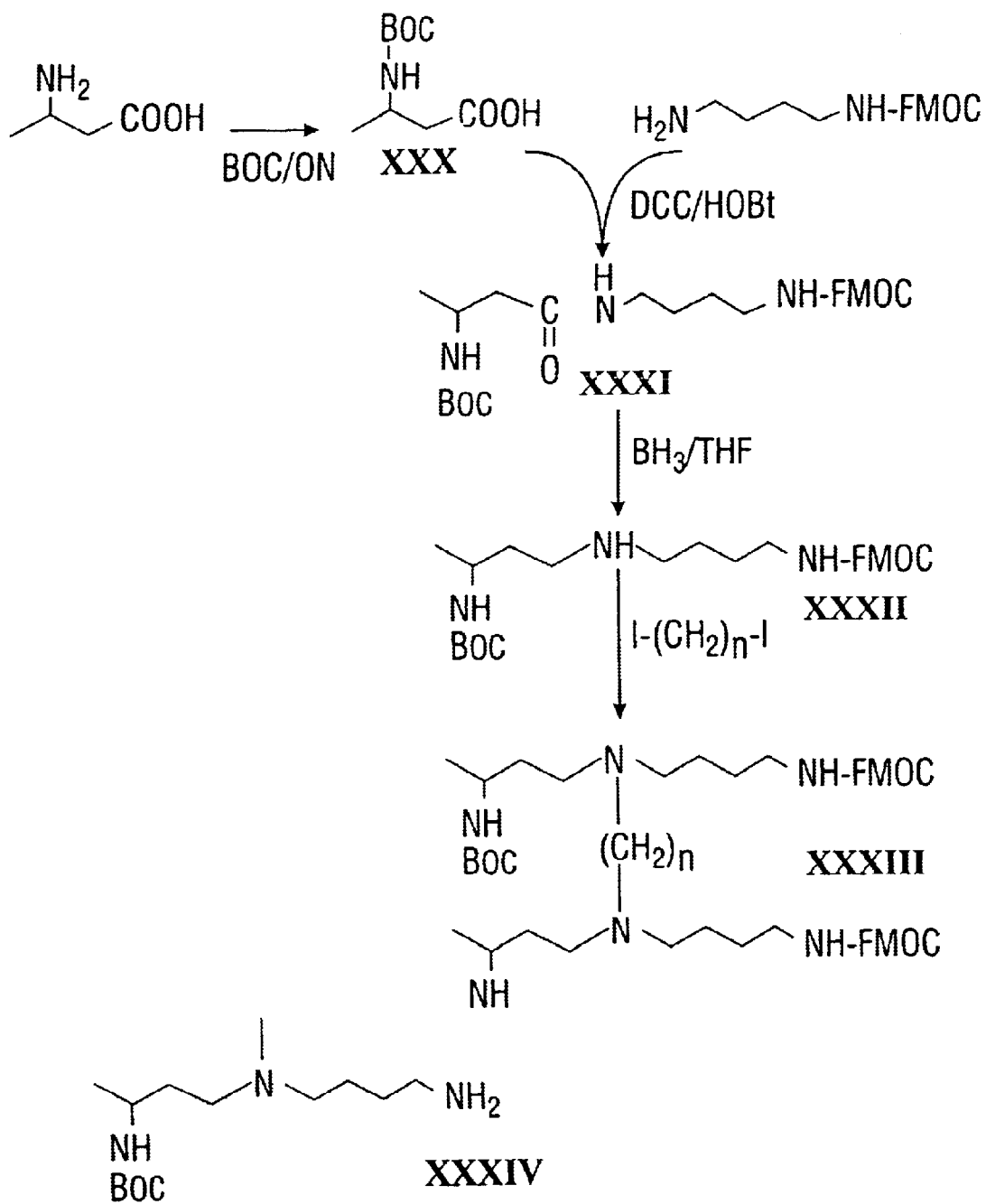
FIG. 20. Initial route of synthesis of terminal C-methylated, $N^4$-alkylated dimeric spermine analogs (FIG. 17B). Steps leading to the synthesis of the intermediate $N^\alpha$, $N^\omega$-bis (N-[N'-Box-3-amino, 3-methylpropyl], N-[4-aminobutyl])-α,ω-diminoalkane. For the aliphatic linker—$(CH_2)_n$—, 2<n<51.

(4) Methylated, N-alkylated spermine analogs (FIG. 17B):

(a) The amino acid group of 3-aminobutyric acid is protected with Boc as described (89), and the resulting N-Boc-3-aminobutyric acid (XXX, FIG. 20) is condensed with N-FMOC-1, 4-diaminobutane using DCC/OHBt (88) to obtain $N^1$-(N-Boc-3-aminobutyryl), $N^4$-FMOC-1,4-diamonobutane (XXXI, FIG. 20).

(b) $N^1$-(N-Boc-3-aminobutyryl), $N^4$-FMOC-1, 4diaminobutane is then reduced to $N^1$-Boc-$N^8$-FMOC-1-methylspermidine with BH$_3$/THF (88) (XXXII, FIG. 20).

(c) Two equivalents of $N^1$-Boc-$N^8$-FMOC-1-methylspermidine are then $N^4$-alkylated with one equivalent of the α,ω-diiodalkane of the desired length to obtain the corresponding $N^\alpha$, $N^\omega$-bis(N-(NBoc-3-amino, 3methylpropyl], N-[N-FMOC-4-aminobutyl]-α,ω-diaminoalkane (XXXIII, FIG. 20).

(d) The FMOC groups of the resulting $N^\alpha$, $N^\omega$-bis(N-[NBoc-3-amino, 3-methylpropyl], N-[N-FMOC-4-aminobutyl]-α,ω-diaminoalkane are then deprotected with 20% piperidine/DMF to yield the corresponding $N^\alpha$, $N^\omega$-bis (N-[NBoc-3-amino,3-methylpropyl], N-[N-4-aminobutyl])-α,ω-diaminoalkane (XXXIV, FIG. 20), which is then condensed with 3-azidobutyric acid, prepared as described (88),using DCC/OHBt, to generate the corresponding $N^\alpha$, $N^\omega$-bis(N-[NBoc-3-amino,3-methylpropyl], N-[N-8-amino-5-aza-octanoyl]-α,ω-diaminoalkane.

Figure 21:
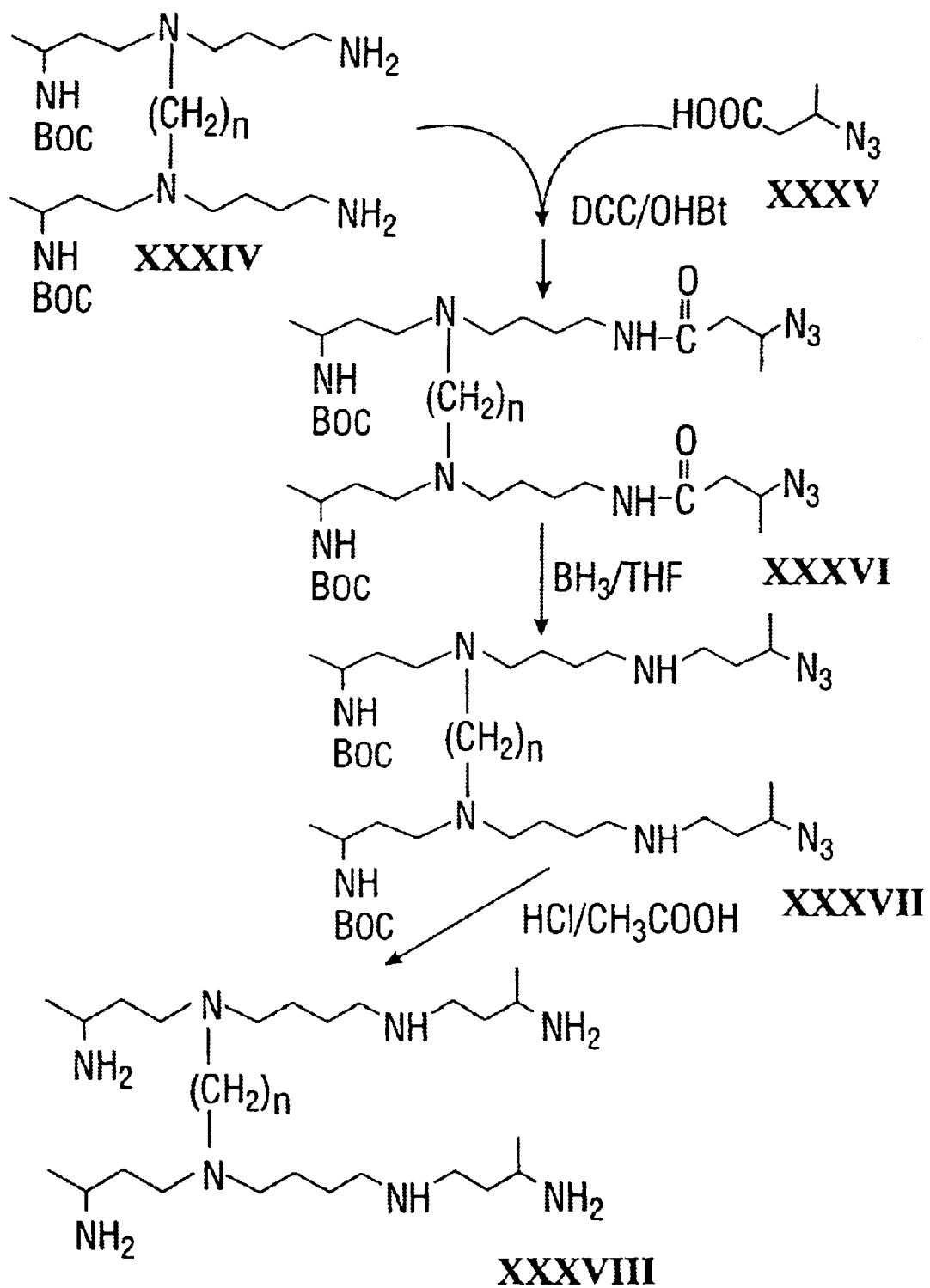
FIG. 21. Final steps for the synthesis of terminal C-methylated, $N^4$-alkylated dimeric spermine analogs (FIG. 17B, represented by type compound XXXVIII). For the aliphatic linker—$(CH_2)_n$—, 2<n<51.

(e) The $N^\alpha$, $N^\omega$-bis(N-[N-Boc-3-amino,3-methylpropyl], N-[N-8-amino-5-aza-octanoyl])-α,ω-diaminoalkane is then reduced to the corresponding $N^\alpha$, $N^\omega$, bis-(N-[N-Boc-3-amino,3-methylpropyl], N-[N-8-amino-5-aza-octyl])-α,ω-diaminoalkane with BH$_3$/THF (88) (XXXVII, FIG. 21).

(f) The Boc groups of $N^\alpha$, $N^\omega$-bis(N-[N-Boc-3-amino,3-methylpropyl], N-[N-8-amino-5-aza-octyl])-α,ω-diaminoalkane are then removed with HCl/CH$_3$COOH to generate the desired transport inhibitor, a $N^\alpha$, $N^\omega$-bis (N-[3-amino, 3-methyl-propyl], N-[8-amino-5-aza-octyl])-α,ω-diaminoalkane (XXXVIII, FIG. 21).

Figure 22:
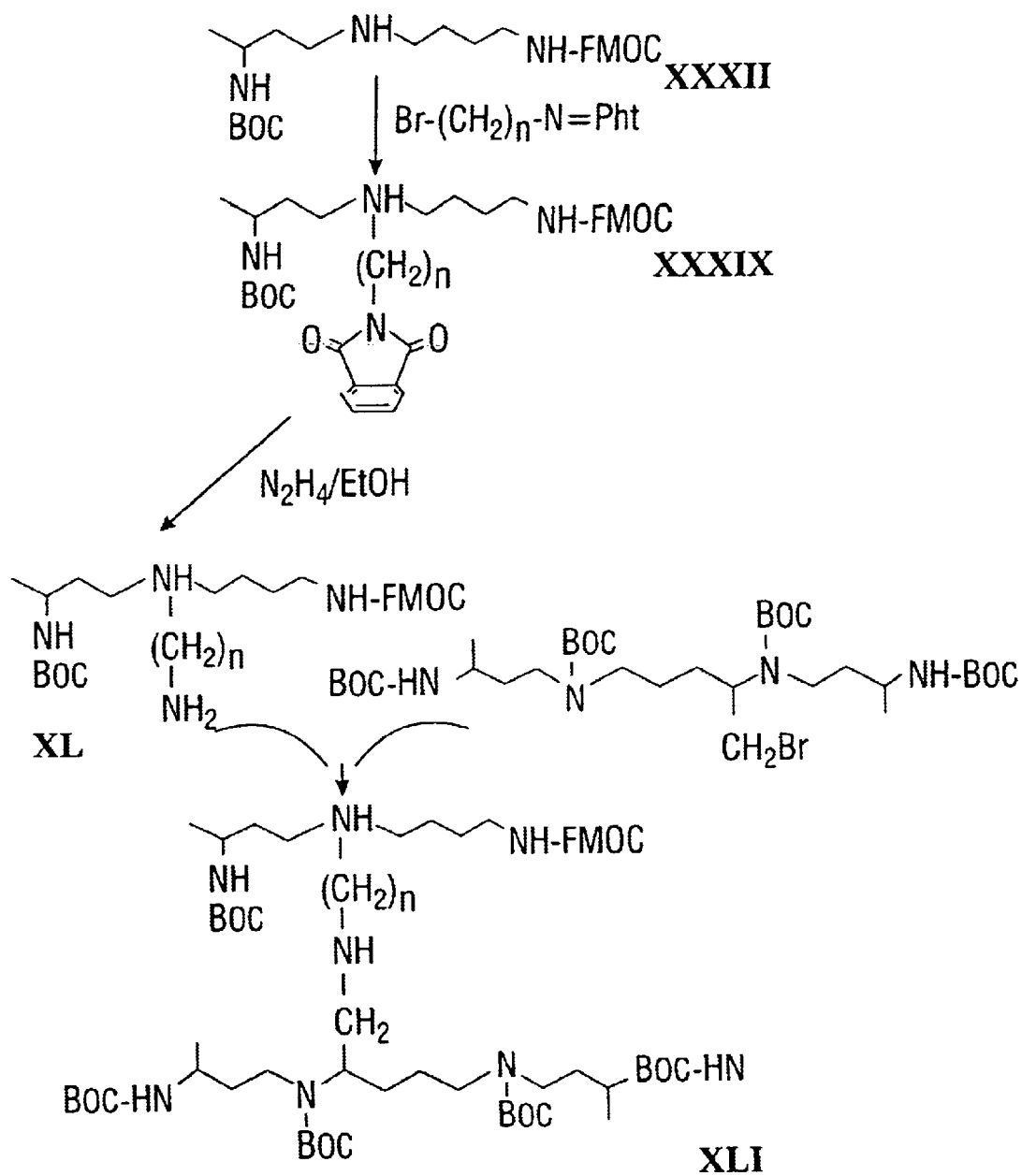
FIG. 22. Initial route of synthesis of 1,12-dimethylspermine dimers cross-linked through $N^4$-alkyl/5-alkyl attachments of the linker (FIG. 17C). Steps leading to the synthesis of the intermediate $N^\alpha$([N'-Boc-3-amino, 3-methylpropyl], N-[N'-FMOC-4-aminobutyl]), $N^\omega$-[5-($N^1$, $N^4$, $N^8$, $N^{12}$-tetra (Boc)-spermine)-methyl]-α,ω-diaminoalkane. For the aliphatic linker —$(CH_2)_n$—, 2<n<51.

(5) 1,12-Dimethylated spermine dimers cross-linked N-alkyl/C-alkyl attachments of the linker (FIG. 17C):

Dimeric polyamine transport inhibitors of a different type can be generated by cross-linking one polyamine chain to a linker through a N-alkyl bond as in Examples 3 and 4 above, and the other polyamine chain via a C-linked anchor lying between the two innermost secondary amino groups as in Examples 1 and 2 above. Such compounds (as terminal-C-methylated spermine analogs) can be obtained as follows:

(a) $N^1$-Boc-$N^8$-FMOC-1-methylspermidine (XXXII, FIG. 20), obtained as described above (Example 4, steps a to b), is $N^4$-alkylated using an ω-bromoalkyphthalimide of the desired length as described (92), to generate the corresponding $N^1$-Boc, $N^4$-alkylphthalimide, $N^8$-FMOC-1-methylspermidine (XXXIX, FIG. 22).

(b) The phthalimide group of $N^1$-Boc, $N^4$-alkylphthalimide, $N^8$-FMOC-1-methylspermidine is removed with hydrazine in.EtOH (88, 90) to generate the corresponding $N^1$-Boc, $N^4$-(ω-aminoalkyl), N-$^8$FMOC-1-methylspermidine (XL, FIG. 22).

(c) The free amino group of $N^1$Boc, $N^4$-(ω-aminoalkyl), $N^8$-FMOC-1-methylspermidine is then alkylated with $N^1$, $N^4$, $N^8$, $N^{12}$-tetra(Boc)-1,12-dimethyl-5-bromomethylspermine prepared as described in Example 2 (XVI, FIG. 14) to obtain the corresponding $N^\alpha$(N-Boc-3-amino, 3-methylpropyl], N-[$N^8$-FMOC-4-aminobutyl]), $N^\omega$-[5-($N^1$, $N^4$, $N^8$, $N^{12}$-tetra(Boc)-spermine)-methyl]α,ω-diaminoalkane (XLI, FIG. 22).

Figure 23:
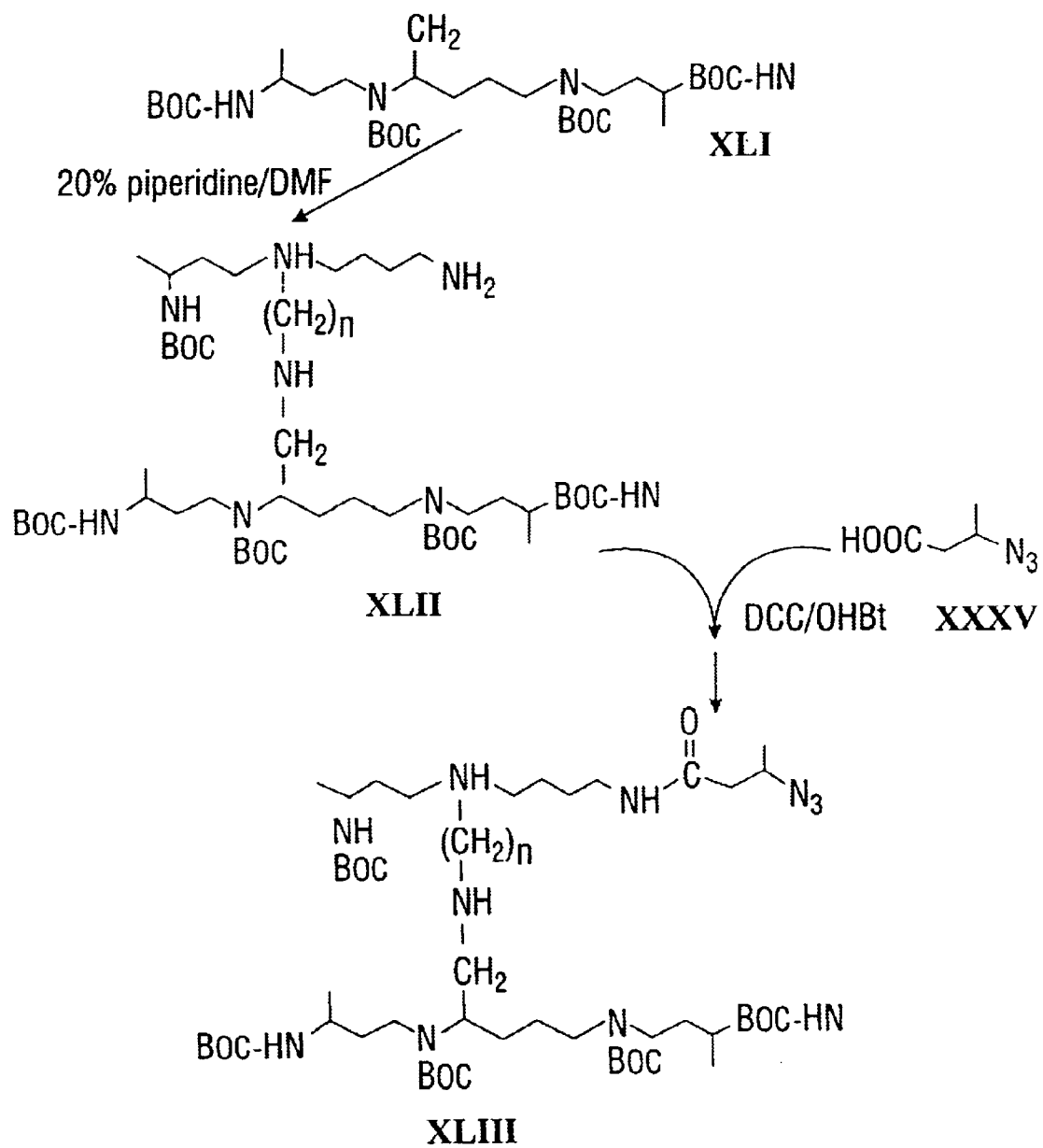
FIG. 23. Intermediate route of synthesis of 1,12-dimethylspermine dimers cross-linked through $N^4$-alkyl/5-alkyl attachments of the linker (FIG. 17C). Steps leading to the synthesis of the intermediate $N^\alpha$([N'-Boc-3-amino, 3-methylpropyl], N-[8-amino-5-aza-octanoyl]), $N^\omega$-[5-($N^1$, $N^4$, $N^8$, $N^{12}$-tetra(Boc)-spermine)-methyl]-α,ω-diaminoalkane. For the aliphatic linker —$(CH_2)_n$—, 2<n<51.

(d) The FMOC group of $N^\alpha$([N-Boc-3-amino, 3-methylpropyl], N-[N-FMOC-4-aminobutyl]), $N^\omega$-[5-($N^1$, $N^4$, $N^8$, $N^{12}$-tetra(Boc)-spermine)-methyl]α,ω-diaminoalkane is then removed with 20% piperidine/ DMF, and the resulting $N^\alpha$([N-Boc-3-amino, 3-methylpropyl], N-[4-aminobutyl]), $N^\omega$-[5-($N^1$, $N^4$, $N^8$, $N^{12}$-tetra(Boc)-spermine)-methyl]α,ω-diaminoalkane (XLIII, FIG. 23) is condensed with 3-azidobutyric acid (XXX. FIG. 21) as in Example 4 (step d) above, to generate the corresponding $N^\alpha$([N-N-Boc-3-amino, 3-methylpropyl], N-[8-amino-5-aza-octanoyl]), $N^\omega$-[5-($N^1$,$N^4$,$N^8$,$N^{12}$-tetra(Boc)-spermine)-methyl]α,ω-diaminoalkane (XLIII, FIG. 23).

Figure 24:
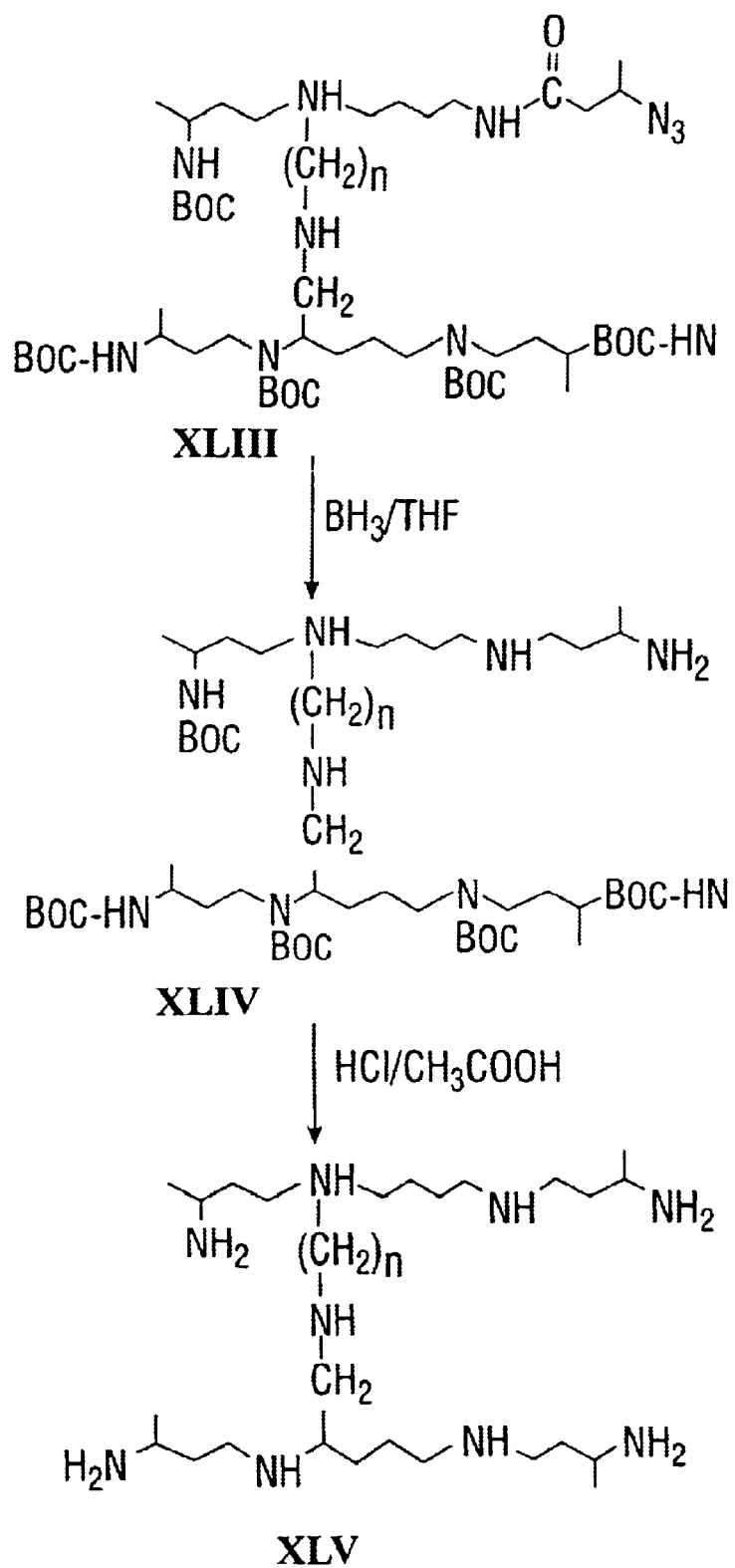
FIG. 24. Final route of synthesis of 1,12-dimethylspermine dimers cross linked through $N^4$-alkyl/5-alkyl attachments of the linker (FIG. 17C represented by type compound XLV). For the aliphatic linker —$(CH_2)_n$—, 2<n<51.
Figure 25A:
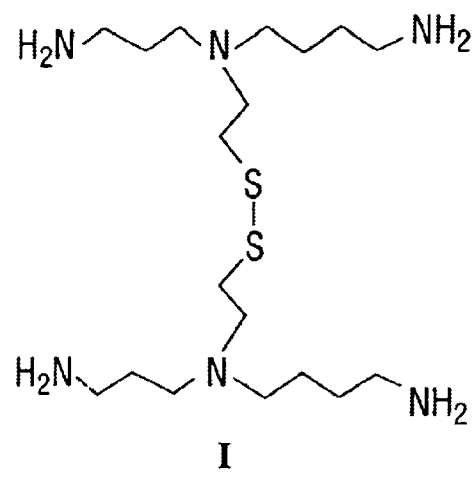
FIG. 25 illustrates the structure of representative dimeric transport inhibitors with a triamine backbone that are included in the present invention. BABAC is N,N'-bis(3-aminopropyl), N,N'-bis(4-aminobutyl)cystamine, a dimeric spermidine derivative with a diethyl disulfide linker: (BNSpd-(n+2) (standing for bis(sym-norspermidine) molecules with a carbon chain length of n+2 atoms; 0<n<7) represents the general structure of dimeric sym-norspermidine-derived transport inhibitors with an aliphatic linker; BSpd-(n+2) (standing for bis(spermidine) molecules with a carbon chain length of n+2 atoms; 0<n<7) represents the general structure of dimeric spermidine-derived transport inhibitors with an aliphatic linker; TADAX is N,N,N', N'-tetrakis(3-aminopropyl)-p-xylylenediamine, a dimeric sym-norspermidine derivative with a p-xylylenediamine linker.
Figure 25B:
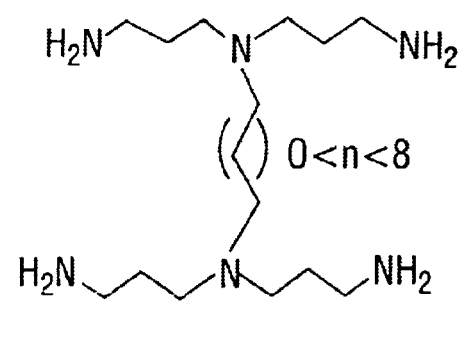
Figure 25C:
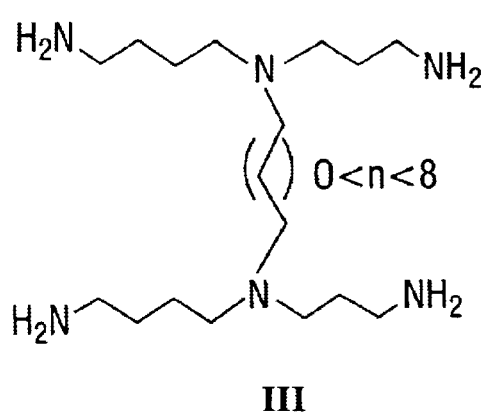
Figure 25D:
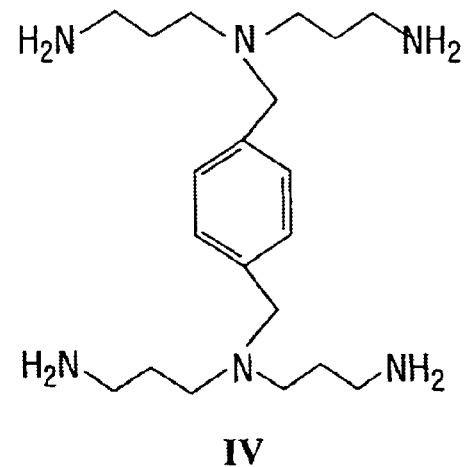

(e) $N^\alpha$(N-[N-Boc-3-methylpropyl], N-[8-amino-5-aza-octanoyl], $N^\omega$-[5-($N^1$, $N^4$, $N^8$, $N^{12}$-tetra(Boc)-spermine)-methyl]-α,ω-diaminoalkane is then reduced to N$^\alpha$(N-[N-Boc-3-amino, 3-methylpropyl], N-[8-amino-5-aza-octyl]), N$^\omega$-[a5-(N$^1$, N$^4$, N$^8$, N$^{12}$-tetra (Boc)-spermine)-methyl]-α,ω-diaminoalkane (XLIV, FIG. 24) with BH$_3$/THF as in Example 4 (step e) above, and the Boc groups of the resulting compound are removed with HCl/CH3COOH to generate the corresponding N$^\alpha$(N-[N-[3-amino, 3-methyl-propyl], N-[8-amino-5-aza-octyl]), N$^\omega$-[5-(1, 12-dimethyl-spermine)-methyl]-α,ω-diaminoalkane (XLV, FIG. 24), which is the desired polyamine transport inhibitor.

(6) SCHEME 1 (FIG. 27): synthesis of sym-norspermidine dimers using total cyanoethylation of aliphatic or aromatic diamines This scheme is used to prepare symmetrical dimers of sym-norspermidine by Michael addition via total cyanoethylation of hydrochloride salts of aliphatic or aromatic α,ω-diamines. This route is the simplest one to generate polyamine dimers since no amine protection is neccessary. The diamin hydrochloride of the desired nature and chain length (VIII, FIG. 27) to be used as a crosslinker is stirred with a 4-fold excess of acrylonitrile in the presence of triethylamine (Et$_3$N) is aqueous solution, yielding a N,N,N', N'-tetrakis(cyanoethyl)-α,ω-diamine (IX, FIG. 27). Cyanoethyl groups are then reduced with NaBH$_4$ in the presence of methanolic CoCl$_2$ as a reducing agent, resulting in the formation of a sym-norspermidine dimer (X, FIG. 27) with the desired linker L. The compound is obtained as its hexahydrochloride salt after alkaline extraction with CHCl$_3$/Na$_2$CO$_3$ and solubilization in HCl.

Figure 27A:
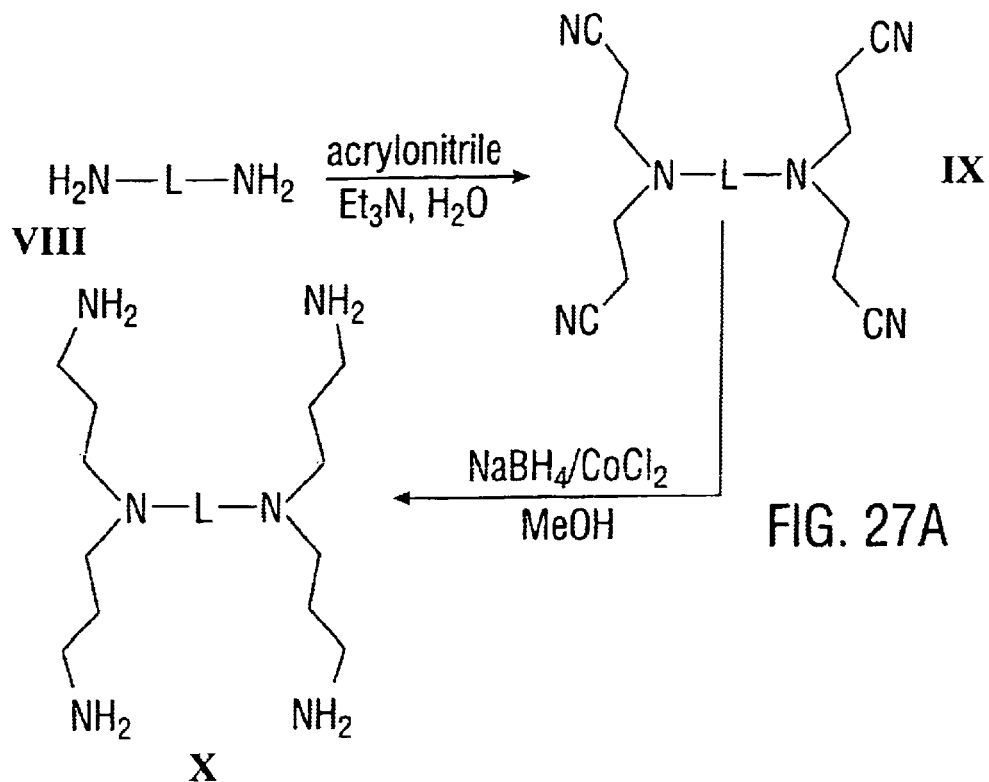
FIG. 27 illustrates synthetic Scheme 1 used to obtain dimeric sym-norspermidine-derived polyamine transport inhibitors (X) from a precursor cross-linking diamine (VIII) containing the linker (L), and typical examples of said linker. $Et_3N$=triethylamine.
Figure 27B:
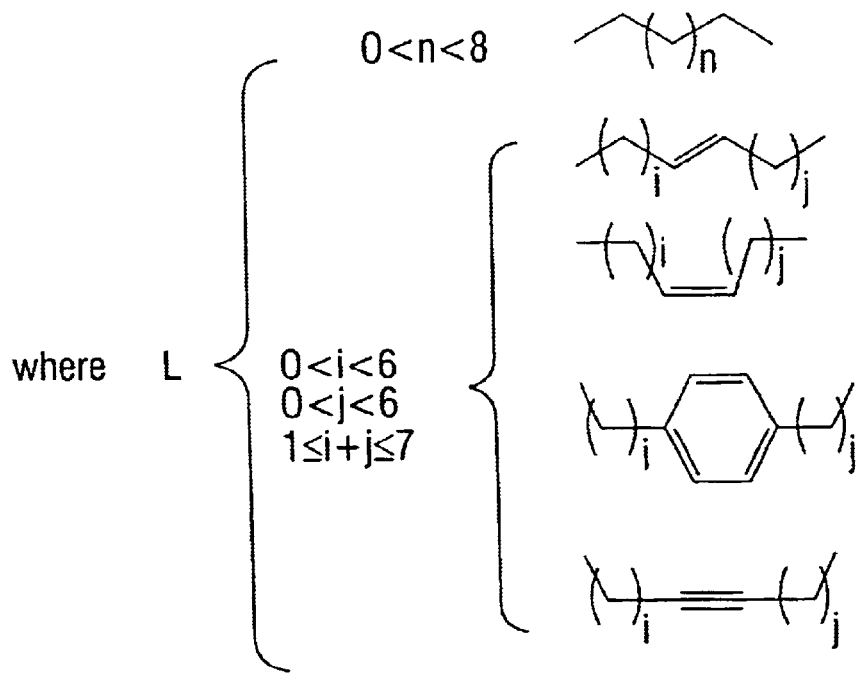

Various linkers can be used according to that scheme, including aliphatic α,ω-diaminoalkanes (preferably with a chain length greater than two and less than ten) which may incorporate one double bond in a cis or trans configuration, or one triple bond, and aromatic diamines where the amino groups are present as aminoalkyl substituents at two different positions of the aromatic cycle, such as the para configuration shown in FIG. 27.

Figure 28A:
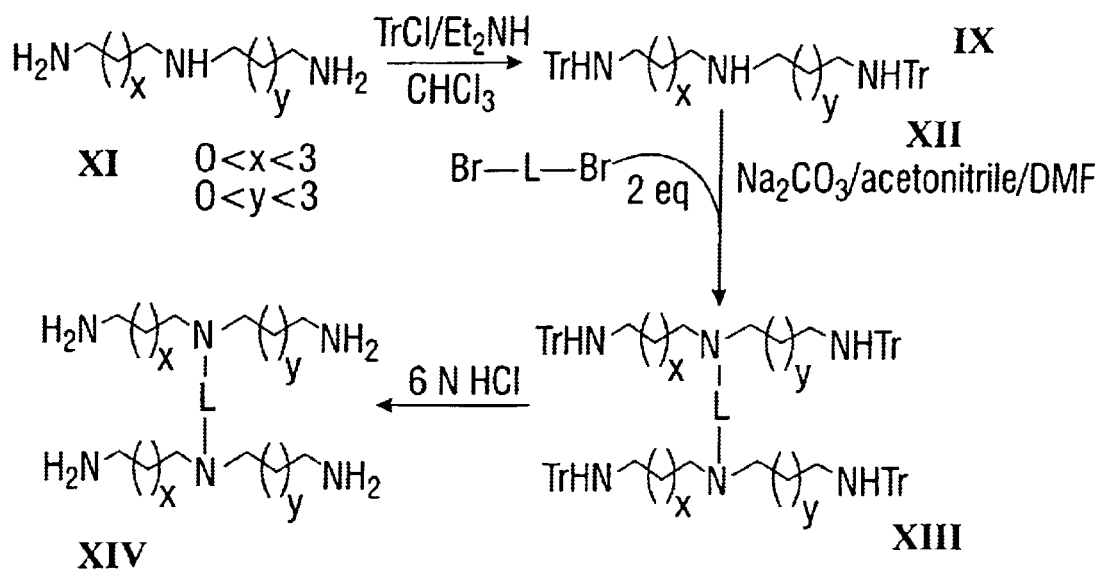
FIG. 28 illustrates synthetic Scheme 2 used to obtain dimeric sym-homospermidine-, sym-norspermidine-, or spermidine-derived polyamine transport inhibitors (XIV) from the parent triamine (XI) cross-linked with a linker L via symmetrical N-alkylation of the secondary amino group of said triamine, and typical examples of said linker. TrCl= trityl chloride; $Et_2NH$=diethylamine; DMF= dimethylformamide.
Figure 28B:
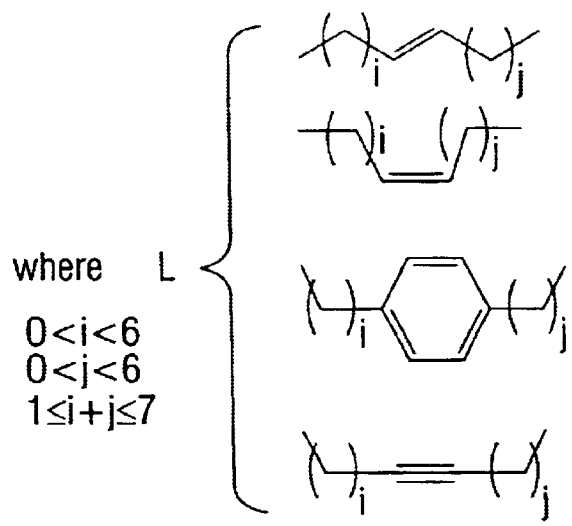

(7) SCHEME 2 (FIG. 28): synthesis of spermidine, sym-homospermidine and sym-norspermidine dimers using direct alkylation of the central secondary amino group with a dibromoalkene or dibromoarene Spermidine, sym-homospermidine and sym-norspemidine dimers can be prepared by protecting the primary amino groups of the precursor triamine with trityl groups, and directly alkylating the secondary amino group of the triamine with a dibromoalkene, a dibromoalkyne or a dibromoarene with the desired crosslinking carbon chain (Zang and Sadler). For this purpose, the primary amine groups of the triamine (FIG. 28) are reacted with trityl chloride in the presence of diethylamine in CHCl$_3$ to obtain the N$^\alpha$, N$^\omega$-bis(trityl) polyamine chain XII (FIG. 28). Two equivalents of the latter compound are then refluxed with the alkyl or aryl dibromide form of the desired linker L to generate the trityl-protoected form of the desired triamine dimer (XIII, FIG. 28). The trityl groups of this dimer are then removed by refluxing with 6 N HCL to obtain the hexahydrochloride salt of the polyamine transport inhibitor XIV (FIG. 28). Dibromoalkanes tend to form heterocyclic by-products with the triamine precursor, and therefore the present scheme is chiefly used as a simply synthetic method to generate dimeric triamine-derived polyamine transport inhibitors with unsatured or aromatic linkers.

Figure 29A:
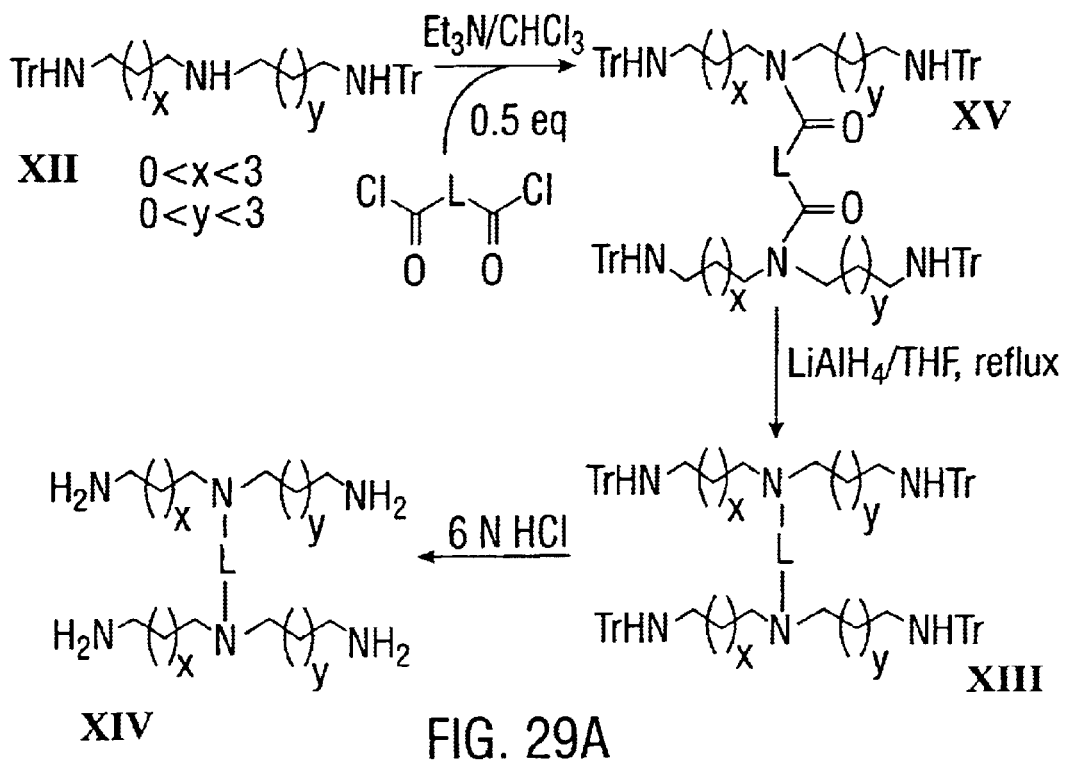
FIG. 29 illustrates synthetic Scheme 3 used to obtain dimeric sym-homospermidine-, sym-norspermidine-, or spermidine-derived polyamine transport inhibitors (XIV) from the trityl-protected parent triamine (XII) cross-linked with a linker L via symmetrical amidation of the secondary amino group of said triamine followed by reduction of the amide bonds, and typical examples of said linker. THF= tetrahydrofuran.
Figure 29B:
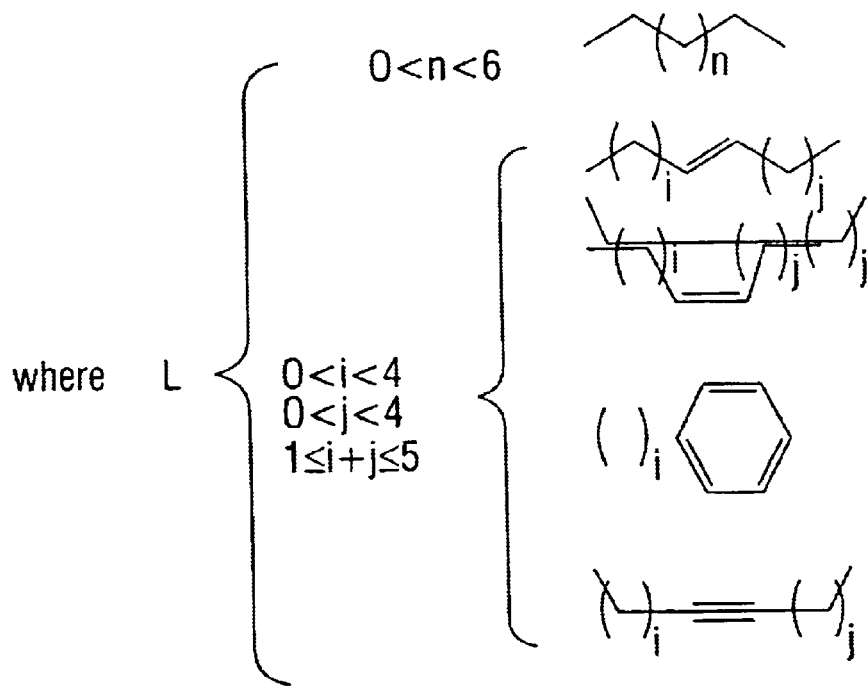

(8) SCHEMe 3 (FIG. 29): synthesis of spermidine sym-homospermidine and sym-norspermidine dimers by amidation with an acyl chloride followed by reduction of the amide groups An alternative, even more versatile approach to generate spermidine, sym-homospermidine and sym-norspermidine dimers as polyamine transport inhibitors is to crosslink the secondary amino groups of the triamine chains, protected with trityl groups as in Scheme 2 (XII, FIG. 28 and FIG. 29), with the α,ω-diacyl chloride form of the desired linker L, and then reduce the amide bonds of the resulting molecules. For this purpose, two equivalents of the trityl-protected triamine precursor XII are reacted with the diacyl chloride of choice in the presence of triethylamine/CHCl$_3$ to obtain the corresponding diamide form of a trityl-protected triaminen dimer XV (FIG. 29). The diamide is then reduced to its N-alkyl form with LiAlH$_4$ in dry THF under nitrogen to obtain the trityl-protected form of the triamine dimer (XIII, FIG. 28 and FIG. 29). The primary amine groups are then freed with 6 N HCl as in Scheme 2 to generate the desired dimeric polyamine transport inhibitor XIV (FIG. 28 and FIG. 29).

This scheme is superior to Scheme 2 for dimerizing triamine molecules with aliphatic linkers of the general structure (—(CH$_2$)$_n$—, which tend to form heterocycles with the polyamine chain when reacted in their dihalide form.

(9) SCHEME 4 (FIG. 30): synthesis of dimeric spermidine, sym-homospermidine and sym-norspermidine disulfides Synthesis of useful dimeric polyamine transport inhibitors is not limited to those containing aliphatic or aromatic carbon chains. Triamines can be dimerized via N-alkyl bonds with a linker L containing a disulfide bond, generating polyamine transport inhibitors with even higher potency than DESC, which is a dimeric spermine disulfide cross-linked through amide bonds with position C5 of each spermine skeleton. The following scheme allows the synthesis of dimeric triamines cross-linked via N-alkyl bonds with a diethyl disulfide chain.

Figure 30:
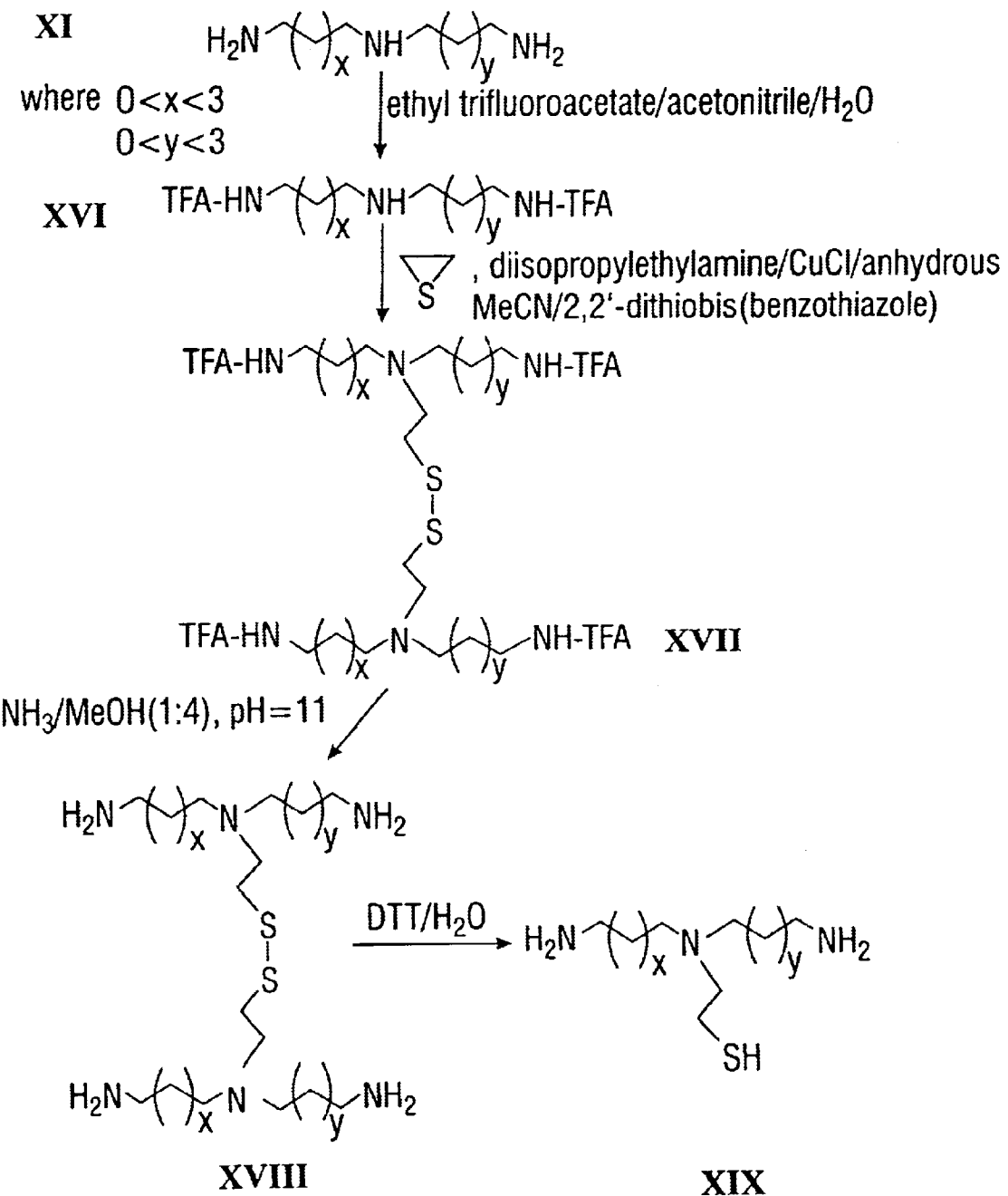
FIG. 30 illustrates synthetic Scheme 4 used to obtain dimeric sym-homospermidine-, sym-norspermidine-, or spermidine-derived polyamine transport inhibitors (XVIII) from the parent triamine (XI) cross-linked via a diethyl disulfide linker L by symmetrical alkylation of the secondary amino group of said triamine. TFA=trifluoroacetyl.

The primary amino groups of the desired triamine XI (FIG. 28 and FIG. 30) are first protected with ethyl trifluoroacetate in aqueous acetonitrile to obtain the bis-trifluoroacetyl)-protected triamine XVI (FIG. 30). The latter compound is then reacted with one equivalent with ethylene sulfide (Cohen, et al.), 1.2 equivalent of diisopropylethylamine (Hunig's base) and 0.1 equivalent of CuCl in dry acetonitrile in the presence of 2,2'-dithiobis(benzothiazole) to catalyze the formation of the disulfide from an intermediate thiol (Brzezinska and Ternay), to generate the trifluoroacetyl-protected triamine dimeric disulfide XVII (FIG. 30). Trifluoroacetyl groups are removed from the latter compound using MeOH/NH$_3$ (4:1) at pH 11, yielding the free dimeric triamine disulfide XVIII (FIG. 30). The latter disulfide can be further reduced to its free thiol XIX (FIG. 30) with either dithiothreitol or tris(carboxyethyl)phosphine (Burns, et al.).

REFERENCES

The following references are specifically incorporated herein by reference for the purposes indicated:

1. Ask, A., L. Persson, and O. Heby. Increased survival of L1210 leukemic mice by prevention of the utilization of extracellular polyamines. Studies using a polyamine-uptake mutant, antibiotics and a polyamine-deficient diet. *Cancer Lett.* 66:29–34, 1992.
2. Aziz, S. M., M. N. Gillespie, P. A. Crooks, S. F. Tofiq, C. P. Tsuboi, J. W. Olson, and M. P. Gosland. The potential of a novel polyamine transport inhibitor in cancer chemotherapy. *J. Pharmacol. Exper. Ther.* 278: 185–192, 1996.
3. Aziz, S. M., M. P. Gosland, P. A. Crooks, J. W. Olson, and M. N. Gillespie. A novel polymeric spermine conjugate inhibits polyamine transport in pulmonary artery smooth muscle cells. *J. Pharmacol. Exp. Ther.* 274: 181–196, 1995.
4. Bacchi, C. J., and P. P. McCann. Parasitic protozoa and polyamines. In: *Inhibition of Polyamine Metabolism. Bio-*

*logical Significance and Basis for New Therapies,* edited by P. P. McCann, A. E. Pegg and A. Sjoerdsma. Orlando, Fla.; Academic Press, 1987, p. 317–344.

5. Bacchi, C. J., H. C. Nathan, A. B. Clarkson, Jr., E. J. Bienen, A. J. Bitonti, P. P. McCann, and A. Sjoerdma. Effects of the ornithine decarboxylase inhibitors DL-α-difluoromethylorthine and α-monofluoromethyldehydroornithine methyl ester alone and in combination with suramin against *Trypanosoma brucei brucei* central nervous system models. *Am. J. Trop. Med. Hyg.* 36: 46–52, 1987.

6. Bardocz, S. The role of basolateral polyamine uptake in intestinal adaptation. In: *Polyamines in the Gastrointestinal Tract,* edited by R. H. Dowling, U. R. Fölsch and C. Löser. Dordrecht: Kluwer Academic Publ., 1992, p. 409–416.

7. Bardocz, S., G. Grant, D. S. Brown, J. C. Stewart, J. F. J. G. Koninkx, H. G. C. J. M. Hendriks and A. Pusztai. Effect of fasting and refeeding on basolateral polyamine uptake and metabolism by the rat jejunum. In: *Polyamines in the Gastrointestinal Tract,* edited by R. H. Dowling, U. R. Fölsch and C. Löser. Dordrecht: Kluwer Academic Publ., 1992, p. 435–445.

8. Bergeron, R. J., and H. W. Seligsohn. Hexahydropyrimidines as masked spermidine vectors in drug delivery. *Bioinorg. Chem.* 14: 345–355, 1986.

9. Byers, T. L., and A. E. Pegg. Regulation of polyamine transport in Chinese hamster ovary cells. *J. Cell. Physiol.* 143: 460–467, 1990.

10. Chaney, J. E., K. Kobayashi, R. Goto, and G. A. Digenis. Tumor selective enhancement of bioactivity uptake in mice treated with α-difluoromethylornithine prior to administration of $^{14}$C-putrescine. *Life Sci.* 32: 1237–1241, 1983.

11. Chang, B. K., P. R. Libby, R. J. Bergeron, and C. W. Porter. Modulation of polyamine biosynthesis and transport by oncogene transfection. *Biochem. Biophys. Res. Commun.* 157:264–270, 1988.

12. Duranton, B., E. Nsi-Emvo, R. Schleiffer, F. Gossé, M. Galluser, and F. Raul. Suppression of preneoplastic changes in the intestine of rats fed low levels of polyamines. *Cancer Res.* 57: 573–575, 1997.

13. Frébort, I., and O. Adachi. Copper/quinone-containing amine oxidases, an exciting class of ubiquitous enzymes. *J. Ferment. Bioeng.* 80: 625–632, 1995

14. Gordonsmith, R. H., S. Brooke-Taylor, L. L. Smith, and G. M. Cohen. Structural requirements of compounds to inhibit pulmonary diamine accumulation. *Biochem. Pharmacol.* 32: 3701–3709, 1983.

15. Hayashi, S., Y. Murakami, and S. Matfufuji. Ornithine decarboxylase antizyme—A novel type of regulatory protein. *Trends Biochem. Sci.* 21: 27–30, 1996.

16. He, Y., T. Suzyki, K. Kashiwagi, and K Igarashi. Antizyme delays the restoration by spermine of growth of polyamine-deficient cells through its negative regulation of polyamine transport. *Biochem. Biophys. Res. Commun.,* 203: 608–614, 1994.

17. Hessels, J., A. W. Kingma, H. Ferwerda, J. Keij, G. A. Van der Berg, and F. A. J. Muskiet. Microbial flora in the gastrointestinal tract abolishes cytostatic effects of α-difluoromethylornithine in vivo. *Int. J. Cancer* 43: 1155–1164, 1989.

18. Hinuma, K, M. Maghsoudloo, G. M. Murphy, and R. H. Dowling. Dietary and intestinal polyamines in the rat: in vitro transport studies. In: *Polyamines in the Gastrointestinal Tract,* edited by R. H. Dowling, U. R. Fölsch and C. Löser. Dordrecht: Kluwer Academic Publ., 1992, p. 463–472.

19. Halley, J. L., A. Mather, R. T. Wheelhouse, P. M. Cullis, J. A. Hartley, J. P. Bingham, and G. M. Cohen. Targeting of tumor cells and DNA by a chlorambucil-spermidine conjugate. *Cancer Res.* 52: 4190–4195, 1992.

20. Hold, Y., P. J. Schechter, and L. J. Marton. Phase I–II clinical trial with alpha-difluoromethylornithine—an inhibitor of polyamine biosynthesis. *Eur. J. Cancer Clin. Oncol.* 23: 1103–1107, 1987.

21. Huber, M., J. Pelletier, K. Torossian, P. Dionne, I. Gamache, R. Charest-Gaudreault, M. Audette, and R. Poulin. 2,2'-Dithiobis(N-ethyl-spermine-5-carboxamide) is a high affinity, membrane-impermeant antagonist of the mammalian polyamine transport system. *J. Biol. Chem.* 271: 27556–27563, 1996.

22. Huber, M., and R. Poulin. Antiproliferative efefct of spermine depletion by N-cyclohexyl-1,3-diaminopropane in human breast cancer cells. *Cancer Res.* 55: 934–943, 1995.

23. Huber, M., and R. Poulin. Permissive role of polyamines in the cooperative action of estrogens and insulin or insulin-like growth factor 1 on human breast cancer cell growth. *J. Clin. Endorcinol. Metab.* 81: 113–123, 1996.

24. Jänne, T., L. Alhonen, and P. Leinonen. Polyamines: from molecular biology to clinical applications. *Ann Med.* 23: 241–259, 1991.

25. Kakinuma, Y., K. Hoshino, and K. Igarashi. Characterization of the inducible polyamine transporter in bovine lymphocytes. *Eur. J. Biochem.* 176: 409–414, 1988.

26. Kanter, P. M., G. A. Bullard, and J. M. King. Preclinical toxicologic evaluation of DENSPM ($N^1,N^{11}$-diethylnorspermine) in rats and dogs. *Anti-Cancer Drugs* 5: 448–456, 1994.

27. Kohn, E. C., E. Reed, G. Sarosy, M. Christian, C. J. Link;, K. Cole, W. D. Figg, P. A. Davis, J. Jacob, B. Goldspiel, and L. A. Liotta. Clinical investigation of a cytostatic calcium influx inhibitor in patients with refractory cancers. *Cancer Res.* 56: 563–568, 1996.

28. Lakanen, J. R., J. K. Coward, and A. E. Pegg, α-Methyl polyamines: metabolically stable spermidine and spermine mimics capable of supporting growth in cells depleted of polyamines: *J. Med. Chem.* 35: 724–734, 1992.

29. Lessard, M., C. Zhao, S. M. Singh, and R. Poulin. Hormonal and feedback regulation of putrescine and spermidine transport in human breast cancer cells. *J. Biol. Chem.* 270: 1685–1694, 1995.

30. Love, R. R., P. P. Carbone, A. K. Verma, D. Gilmore, P. Carey, K. D. Tutsch, M. Pomplun, and G. Wilding. Randomized phase I chemoprevention dose-seeking study of α-difluoromethylornithine. *J. Natl. Cancer Inst.* 85: 732–737, 1993.

31. Marton, L. J., and A. E. Pegg. Polyamines as targets for therapeutic intervention. *Ann. Rev. Pharmacol. Toxicol.* 35: 55–91, 1995.

32. Mausumoto, T., and O. Suzuki. Polyamines as markers of malignancy. In: *The Physiology of Polyamines,* edited by U. Bachrach and Y. M. Heimer. Boca Raton, Fla.: CRC Press, 1989, p. 219–234.

33. McCann, P. P., and A. E. Pegg. Ornithine decarboxylase as an enzyme target for therapy. *Pharmac. Ther.* 54:195–212, 1992.

34. McCannn, P. P., and A. J. Bitonti. An overview of inhibition of polyamine metabolism and the consequent effects on cell proliferation in mammalian cells and parasitic protozoa. In: *Polyamines in the Gastrointestinal Tract,* edited by R. H. Dowling, U. R. Fölsch and C. Löser. Dordrecht: Klawer Academic Publ., 1992, p. 143–153.

35. McCormack, S. A., and L. R. Johnson. Putrescine uptake and release by colon cancer cells. *Am. J. Physiol.* 256: G868–G877, 1989.
36. Meyskens, F. L., Jr., and E. W. Gerner. Development of difluoromethylornithine as chemoprevention agent for the management of colon cancer. *J. Cell. Biochem.:* 126–131, 1995.
37. Minchin, R. F., R. L. Martin, L, A. Summers, and K. F. Ilett. Inhibition of putrescine uptake by polypyridinium quaternary salts in B16 melanoma cells treated with difluoromethylornithine. *Biochem. J.* 262: 391–395, 1989.
38. Mitchell, J. L. A., R. R. Diveley, Jr., and A. Bareyal-Leyser. Feedback repression of polyamine uptake into mammalian cells require active protein synthesis. *Biochem Biophys. Res. Commun.* 186: 81–88, 1992.
39. Mitchell, J. L. A., G. G. Judd, A. Bareyal-Leyser, and S. Y. Ling. Feedback repression of polyamine transport is mediated by antizyme in mammalian tissue-culture cells. *Biochem. J.,* 299. 19–22, 1994.
40. Morgan, D. M. L. Polyamine oxidases and oxidized polyamines. In: *The Physiology of Polyamines,* edited by U. Bachrach and Y. M. Heimer. Boca Raton, Fla.: CRC Press, 1989, p. 203–229.
41. Moulinoux; J.-P., V. Quemener, B. Cipolla, P. Guillé, R. Havouis, C. Martin, B. Lobel, and N. Seiler. The growth of MAT-LyLu rat prostatic adenocarcinoma can be prevented in vivo by polyamine deprivation. *J. Urol.* 146: 1408–1412, 1991.
42. Moulinoux, J.-P., V. Quemener, and N. A. Khan. Biological significance of circulating polyamines in oncology. *Cell. Mol. Biol.* 37: 773–783, 1991.
43. Nicolet:, T., J.-L. Scemama, L. Pradayrol, P. Berthélémy, C. Seva, and N. Vaysse. Putrescine and spermidine uptake is regulated by proliferation and dexamethasone treatment in AR4-2J cells. *Int. J. Cancer* 49: 577–581, 1991.
44. O'Sullivan, M. C., D. M. Dalrymple, and Q. B. Zhou. Inhibiting effects of spermidine derivatives on *Trypanosoma cruzi* trypanothione reductase. *J. Enzym. Inhib.* 11: 97–114, 1996.
45. Osborne, D. L., and E. R. Scidel. Gastrointestinal luminal polyamines: cellular accumulation and enterohepatic circulation. *Am. J. Physiol.* 258: G576–G584, 1990.
46. Parchment, R. E., A. Lewellyn, D. Swartzendruber, and G. B. Pierce. Serum amine oxidase activity contributes to crisis in mouse embryo cell lines. *Proc. Natl. Acad. Sci. USA* 87: 4340–4344, 1990.
47. Pegg, A. E., P. P. McCann, and A. Sjocrdsma. Inhibition of polyamine biosynthesis and function as an approach to drug design. In: *Enzymes as Targets for Drug Design,* edited by M. G. Palfreyman, P. P. McCann, P. P. Lovenberg, W. Temple, J. G. Temple and A. Sjoerdsma. Orlando: Academic Press, 1989, p. 159–183.
48. Pegg, A. E., R. Poulin, and J. K. Coward. Use of aminopropyltransferase inhibitors and of non-metabolizable analogs to study polyamine regulation and function. *Int. J. Biochem. Cell. Biol.* 27: 425–442, 1995.
49. Pegg, A. E., R. Wechter, R. Poulin, P. M. Woster, and J. K. Coward. Effect of S-adenosyl-1,12-diamino-3-thio-9-azadodecane, a multisubstrate adduct inhibitor of spermine synthase, on polyamine metabolism in mammalian cells. *Biochemistry* 28: 844t–8453, 1989.
50. Persson, L., I. Holm, A. Ask, and O. Heby. Curative effect of DL-2-difluoromethylornithine on mice bearing mutant L1210 leukemia cells deficient in polyamine uptake. *Cancer Res.* 48: 4087–4811, 1988.
51. Pohjanpelto, P. Putrescine transport is greatly increased in human fibroblasts initiated to proliferate. *J. Cell Biol.* 68: 512–520, 1976.
52. Porter, C. W., R. J. Bergeron, and N. J. Stolowich. Biological properties of $N^4$-spermidine derivatives and their potential in anticancer therapy. *Cancer Res.* 42: 4072–4078, 1982.
53. Porter, C. W., R. J. Benacki, J. Miller, and R. J. Bergeron. Antitumor activity of $N^1,N^{11}$-bis(ethyl)norspermine against human melanoma xenografts and possible biochemical correlates of drug action. *Cancer Res.* 53: 581–586, 1993.
54. Porter, C. W., P. F. Cavanaugh, Jr., N. Stolowich, B. Ganis, E. Kelly, and R. J. Bergeron. Biological properties of $N^4$- and $N^1,N^8$-spermidine derivatives in cultured L1210 leukemia cells. *Cancer Res.* 45: 2050–2057, 1985.
55. Porter, C. W., B. Ganis, Y. Rustum, C. Wrzosek, D. L. Kramer, and R. J. Bergeron. Collateral sensitivity of human melanoma multidrug-resistant variants to the polyamine analogue, $N^1,N^{11}$diethylnorspermine. *Cancer Res.* 54: 5917–5924, 1994.
56. Porter, C. W., J. Miller, and R. J. Bergeron. Aliphalic chain length specificity of the polyamine transport system in ascites L1210 leukemia cells. *Cancer Res.* 44: 126–128, 1984.
57. Porter, C. W., U. Regenass, and R. J. Bergeron. Polyamine inhibitors and analogues as potential anticancer agents. In: *Polyamines in the Gastrointestinal Tract,* edited by R. H. Dowling, U. R. Foëlsch and C. Löser. Dordrecht: Kluwer Academic Publ., 1992, p. 301–322.
58. Pusztai, A., S. W. B. Ewen, G. Grant, D. S. Brown, W. J. Peumans, E. J. M. Van Damme, and S. Bardocz. Stimulation of growth and polyamine accretion in the small intestine and pancreas by lectins and trypsin inhibitors. In: *Polyamines in the Gastrointestinal Tract,* edited by R. H. Dowling, U. R. Fölsch and C. Löser. Dordrecht: Kluwer Academic Publ., 1992, p. 473–483.
59. Quemener, V., Y. Blanchard, L. Chamaillard, L. Havouis, B. Cipolla, and J.-P. Moulinoux. Polyamine deprivation: a new tool in cancer treatment *Anticancer. Res.* 14: 443–448, 1994.
60. Quemener, V., J. P. Moulinoux, C. Bergeron, F. Darcel, B. Cipolla, A. Denais, R. Havouis, C. Martin, Ad N. Seiler. Tumour growth inhibition by polyamine deprivation. In: *Polyamines in the Gastrointestinal Tract,* edited by R. H. Dowling, U. R. Fölsch and C. Löser. Dordrecht: Kluwer Academic Publ., 1992, p. 375–385.
61. Rinehart, C. A., and K. Y. Chen. Characterization of the polyamine transport system in mouse neuroblastoma cells. Effects of sodium and system A amino acids. *J. Biol. Chem.* 259: 4750–4756, 1984.
62. Sarhan, S., B. Knödgen, and N. Seiler. The gastrointestinal tract as polyamine source for tumor growth. *Anticancer Res.* 9: 215–224, 1989.
63. Scalabrino, G., and M. E. Ferioli. Polyamines in mammalian tumors. II *Adv. Cancer Res.* 36: 1–102, 1981.
64. Scalabrino, G., and M. E. Feroli. Polyamines in mammalian tumors. I. *Adv. Cancer Res.* 35: 151–268, 1981.
65. Schechter, P. J., J. L. R. Barlow, and A. Sjoerdma. Clinical aspects of inhibition of ornithine decarboxylase with emphasis on therapeutic mals of eflornithine (DEMIO) in cancer and protozoan diseases: In: *Inhibition of Polyamine Metabolism. Biological Significance and Basis for New Therapies,* edited by P. P. McCann, A. E. Pegg and A. Sjoerdsma. Orlando, Fla.: Academic Press, 1987, p. 345–364.
66. Seiler, N. Acetylation and interconversion of the polyamines. In: *The Physiology of Polyamines,* edited by U. Bachrach and Y. M. Heimer, Boca Raton, Fla.: CRC Press, 1989, p. 159–176.

67. Seiler, N. Polyamine catabolism and elimination by the vertebrate organism. In: *Polyamines in the Gastrointestinal Tract,* edited by R. H. Dowling, U. R. Fölsch and C. Löser. Dordrecht: Kluwer Academic Publ., 1992, p. 65–85.
68. Seiler, N., J. G. Delcros, and J. P. Moulinoux. Polyamine transport in mammalian cells. An update. *Int. J. Biochem. Cell. Biol.* 28: 843–861, 1996.
69. Seiler, N., and F. Dezeure. Polyamine transport in mammalian cells. *Int. J. Biochem.* 22:211–218, 1990.
70. Seiler, N., S. Sarhan, C. Grauffel, R. Jones, B. Knödgen, and J.-P. Moulinoux. Endogenous and exogenous polyamines in support of tumor growth. *Cancer Res.* 50: 5077–5083, 1990.
71. Sjoerdsma, A. Suicide enzyme inhibitors as potential drugs. *Clin. Pharmacol. Therap.* 30: 3–22, 1981.
72. Sjoerdsma, A., J. A. Golden, P. J. Schechter, J. L. R. Barlow, and D. V. Santi. Successful treatment of lethal protozoal infections with the ornithine decarboxylase inhibitor, α-difluoromethylornithine. *Trans. Ass. Am. Physic.* 97: 70–79, 1984.
73. Sjoerdsma, A., and P. J. Schechter. Chemotherapeutic implications of polyamine biosynthesis inhibition. *Cli. Pharmacol. Therap.* 35: 287–300, 1984.
74. Steele, V. E., R. C. Moon, R. A. Lubet, C. J. Grubbs, B. S. Reddy, M. Wargovich, D. L. McCormick, M. A. Pereira, J. A. Crowell, D. Bagheri, C. C. Sigman, C. W. Boone, and G. I. Kelloff. Preclinical efficacy evaluation of potential chemopreventive agents in animal carcinogenesis: methods and results from the NCI Chemoprevention Drug Development Program. *J. Cell. Biochem. (suppl.)* 20: 32–54, 1994.
75. Sunkara, P. S., S. B. Baylin, and G. D. Luk. Inhibitors of polyamine biosynthesis: cellular and in vivo effects on tumor proliferation. In: *Inhibition of Polyamine Metabolism Biological Significance and Basis for New Therapies,* edited by P. P. McCann, A. E. Pegg and A. Sjoerdsma. Orlando: Academic Press, 1987, p. 121–138.
76. Talpaz, M., K. Nishioka, and J. Gutterman. Clinical studies of α-difluoromethylornithine and α-interferon combination in cancer patients. In: *The Physiology of Polyamines,* edited by U. Bachrach and Y. M. Heimer, Boca Raton, Fla.: CRC Press, 1989, p. 287–292.
77. Tanaka, T., T. Kojima, A. Hara, H. Sawada, and H. Mori. Chemoprevention of oral carcinogenesis by DL-α-difluoromethylornithine, an ornithine decarboxylase inhibitor: dose-dependent reduction in 4-nitroquinoline 1-oxide-induced tongue neoplasms in rats. *Cancer Res.* 53: 772–776, 1993.
78. Tempero, M. A., K. Nishioka, K. Knott, and R. K Zetterman. Chemoprevention of mouse colon tumors with difluoromethylornithine during and after carcinogen treatment. *Cancer Res.* 49: 5793–5797, 1989.
79. Tjandrawinata, R. R., and C. V. Byus. Regulation of the efflux of putrescine and cadaverine from rapidly growing cultured RAW 264 cells by extracellular putrescine. *Biochem. J.* 305: 291–299, 1995.
80. Tjandrawinata, R. R., L. Hawel, and C. V. Byus. Regulation of putreseine export in lipopolysaccharide or IFN-gamma-activated murine monocytic-leukemic RAW 264 Cells. *J. Immunol.* 152: 3039–3052, 1994.
81. Li, Y., MacKerell, A. D., Jr., Egorin, M. J., Ballesteros, M. F. Rosen, M. F., Rosen, M., Wu. Y.-Y., Blamble, D. A., and Callery, P. S. (1997) *Cancer Res.,* 57, 234–239.
82. Bergeron, R. J., Ludin, C., Muller, R., Smith, R. E., and Phanstiel, O., IV. (1997) *J. Org. Chem.* 62, 3285–3290.
83. Tobari, J., and Tchen, T. T. (1983) *Meth. Enzymol.* 94, 431–433.
84. Bergeron, R. J., and Garlich, J. R. (1984) *Synthesis* 782–784.
85. Bergeron, R. J., and Garlich, J. R., and Stolowich, N. J. (1984) *J. Org. Chem.* 49, 2997.
86. Itoh, M., Hagiwara, D., and Kamya, T. (1977) *Bull. Chem. Soc. Jpn.* 50, 718–721.
87. O'Sullivan, M. C., Dalrymple, D. M., and Zhou, Q. B., (1996) *J. Enzym. Inhib.* 11, 97–114.
88. Huber, M., J. Pelletier, K. Torossian, P. Dionne, I. Gamache, R. Charest-Gaudreault, M. Audette, and R. Poulin. (1996) *J. Biol. Chem.* 271, 27556–27563.
89. Stark, P. A., B. D. Thrall, G. G. Meadows, and M. M. Abdel-Monem. (1992) *J. Med. Chem.* 35, 4264–4269.
90. Lakanen, J. R., J. K. Coward, and A. E. Pegg (1992) *J. Med. Chem.* 35, 724–734.
91. U.S. Pat. No. 5,456,908—Aziz, et al.
92. Itoh, M., D. Hagiwara, and T. Kamiya (1997) *Bull. Chem. Soc. Jpn.* 50 718–721.
93. Felschow, D. M., J. MacDiarmid, T. Bardos, R. Wu, P. M. Woster, and C. W. Porter (1995) "Photoaffinity labeling of a cell surface polyamine inding protein." 270 48 28705–28711.
94. Bergeron, R. J. and H. W. Seligsohn (1986) Hexahydropyrimidines as masked spermidine vectors in drug delivery. *Bioinorg. Chem.* 14:345–355.
95. Brzezinska, E., and A. L. Ternay, Jr. (1994) Disulfides. 1. syntheses using 2,2'-dithiobis(benzothiazole). *J. Org. Chem.* 59:8239–8244.
96. Burns, J. A., J. C. Butler, J. Moran, and G. M. Whitesides (1991) Selective reduction of disulfides by tris(2-carboxyethyl)phosphine. *J. Org. Chem.* 56:2648–2650.
97. Cohen, G. M., P. M. Cullis, J. A. Hartley, A. Mather, M. C. R. Symons, and R. T. Wheelhouse (1992) Targeting of cytotoxic agents by polyamines: synthesis of a chlorambucil-spermidine conjugate. *J. Chem. Soc. Chem. Commun.* 293–300.
98. Komori, T., and Y. Ohsugi (1991) Norspermidine inhibits LPs-induced immunoglobulin production in an FCS-independent mechanism different from spermidine and spermine. *Int. J. Pharmacol.* 13:67–73.
99. Lessard, M., C. Zhao, S. M. Singh, and R. Poulin (1995) Hormonal and feedback regulation of putrescine and spermidine transport in human breast cancer cells. *J. Biol. Chem.* 270:1685–1694.
100. Porter, C. W., and R. J. Bergeron (1983) Spermidine requirement for cell proliferation in eukaryotic cells: structural specificity and quantitation. *Science* 219:1083–1085.
101. Poulin, R., C. Zhao, S. Verma, R. Charest-Gaudreault, and M. Audette (1998) Dependence of mammalian putrescine and spermidine transport on membrane potential: identification of an amiloride binding site on the putrescine carrier. *Biochem. J.* 330:1283–1291.
102. Zang, E., and P. J. Sadler (1997) Synthesis of hexamine ligands by using trityl as an N-blocking agent. *Synthetic Communications* 27:3145–3150.

What is claimed is:

1. A synthetic polyamine dimer formed of two polyamine units, each having at least three amino groups including an intermediate amino group, said units being attached to each other by alkylation through a linker which is a chemical entity that is covalently attached to both said intermediate amino groups said polyamine dimer having the following structure (3):

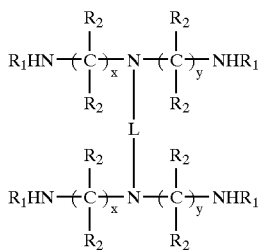

wherein $R_1$ is H, methyl, ethyl, n-propyl or isopropyl, $R_2$ is H or methyl, x is greater than two and less than five ($2<x<5$), y is greater than 2 and less than five ($2<y<5$) and L is the following chemical entity

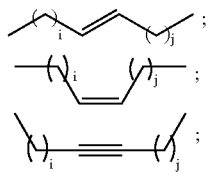

wherein $0<i<6$
$0<j<6$
$1 \leq i+j \leq 7$;
covalently connecting said first polyamine chain to said second polyamine chain.

2. The synthetic polyamine dimer as defined in claim 1, wherein x=3, $R_1$ is a hydrogen atom and $R_2$ is a methyl ($CH_3$) group.

3. A synthetic polyamine dimer formed of two polyamine units, each having at least three amino groups including an intermediate amino group, said units being attached to each other by alkylation through a linker which is a chemical entity that is covalently attached to both said intermediate amino groups said polyamine dimer having the following structure (3):

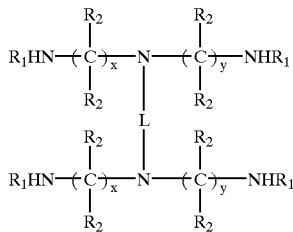

wherein $R_1$ and $R_2$ are as defined in claim 1, where x and y are greater than 2 and smaller than 5 ($2<x<5$, $2<y<5$), where the sum of x and y is greater than 5 and smaller than 9 ($5<(x+y)<9$) and where L is the linker as defined in claim 1.

4. The synthetic polyamine dimer as defined in claim 3, wherein $R_1$ is H, x is 3 or 4, y is 3 or 4.

* * * * *

UNITED STATES PATENT AND TRADEMARK OFFICE
CERTIFICATE OF CORRECTION

PATENT NO. : 6,949,679 B1
DATED : September 27, 2005
INVENTOR(S) : Patrice Preville It is certified that error appears in the above-identified patent and that said Letters Patent is hereby corrected as shown below:

<u>Title page,</u>
Item [75], Inventors, third inventor's name should read -- Rene Charest-Gaudreault --.

Signed and Sealed this

Twenty-fourth Day of January, 2006

JON W. DUDAS
*Director of the United States Patent and Trademark Office*